(12) United States Patent
Angert et al.

(10) Patent No.: US 8,986,355 B2
(45) Date of Patent: Mar. 24, 2015

(54) FACET FUSION IMPLANT

(75) Inventors: Nicholas Angert, West Chester, PA (US); Benjamin Barrall, West Chester, PA (US); David Chow, West Chester, PA (US); Justin Coppes, West Chester, PA (US); Lauren Pietruszynski, West Chester, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 335 days.

(21) Appl. No.: 13/180,422

(22) Filed: Jul. 11, 2011

(65) Prior Publication Data
US 2012/0010659 A1    Jan. 12, 2012

Related U.S. Application Data

(60) Provisional application No. 61/363,077, filed on Jul. 9, 2010.

(51) Int. Cl.
| | | |
|---|---|---|
| *A61B 17/04* | (2006.01) | |
| *A61B 17/84* | (2006.01) | |
| *A61B 17/17* | (2006.01) | |
| *A61B 17/70* | (2006.01) | |
| *A61B 17/86* | (2006.01) | |
| *A61B 17/88* | (2006.01) | |
| *A61B 17/92* | (2006.01) | |
| *A61B 17/34* | (2006.01) | |
| *A61B 17/16* | (2006.01) | |

(52) U.S. Cl.
CPC ......... *A61B 17/7064* (2013.01); *A61B 17/1757* (2013.01); *A61B 17/864* (2013.01); *A61B 17/8872* (2013.01); *A61B 17/92* (2013.01); *A61B 17/3472* (2013.01); *A61B 17/1671* (2013.01)
USPC ............................ 606/300; 606/301; 606/305

(58) Field of Classification Search
USPC .......................................... 606/301, 305, 308
See application file for complete search history.

(56) References Cited

U.S. PATENT DOCUMENTS

| | | |
|---|---|---|
| 4,344,190 A | 8/1982 | Lee et al. |
| 4,501,269 A | 2/1985 | Bagby |
| 4,754,749 A | 7/1988 | Tsou |
| 4,878,915 A | 11/1989 | Brantigan |
| 4,898,186 A | 2/1990 | Ikada et al. |
| 4,940,467 A | 7/1990 | Tronzo |
| 5,015,247 A | 5/1991 | Michelson |

(Continued)

FOREIGN PATENT DOCUMENTS

| | | |
|---|---|---|
| EP | 0 857 465 | 8/1998 |
| EP | 2249730 | 11/2010 |

(Continued)

OTHER PUBLICATIONS

International Patent Application No. PCT/US2009/036175: International Search Report dated Jul. 27, 2009, 18 pages.

(Continued)

*Primary Examiner* — Nicholas Woodall
(74) *Attorney, Agent, or Firm* — Baker & Hostetler LLP

(57) ABSTRACT

Facet fusion implants with various body geometries are provided. The bodies of the facet fusion implants can be configured to minimize migration of the implants when the implants are inserted into facet joints. Surgical methods and accompanying surgical instrumentation for inserting the facet fusion implants into facet joints are provided.

27 Claims, 45 Drawing Sheets

(56) References Cited

U.S. PATENT DOCUMENTS

| | | |
|---|---|---|
| 5,122,132 A | 6/1992 | Bremer |
| 5,334,204 A | 8/1994 | Clewett et al. |
| 5,527,312 A | 6/1996 | Ray |
| 5,571,191 A | 11/1996 | Fitz |
| 5,593,409 A | 1/1997 | Michelson |
| 5,669,909 A | 9/1997 | Zdeblick et al. |
| 5,709,687 A | 1/1998 | Pennig |
| 5,772,661 A | 6/1998 | Michelson |
| 5,928,284 A | 7/1999 | Mehdizadeh |
| 6,014,588 A | 1/2000 | Fitz |
| 6,039,762 A | 3/2000 | McKay |
| 6,045,534 A * | 4/2000 | Jacobsen et al. ............... 604/156 |
| 6,045,580 A | 4/2000 | Scarborough et al. |
| 6,056,192 A | 5/2000 | Cameron |
| RE36,758 E | 6/2000 | Fitz |
| 6,077,267 A | 6/2000 | Huene |
| 6,099,529 A | 8/2000 | Gertzman et al. |
| 6,117,162 A | 9/2000 | Schmieding et al. |
| 6,132,464 A | 10/2000 | Martin |
| 6,162,225 A | 12/2000 | Gertzman et al. |
| 6,200,347 B1 | 3/2001 | Anderson et al. |
| 6,210,412 B1 | 4/2001 | Michelson |
| 6,280,447 B1 | 8/2001 | Marino et al. |
| 6,368,322 B1 | 4/2002 | Luks et al. |
| 6,371,986 B1 | 4/2002 | Bagby |
| 6,419,703 B1 | 7/2002 | Fallin et al. |
| 6,419,706 B1 | 7/2002 | Graf |
| 6,485,518 B1 | 11/2002 | Cornwall et al. |
| 6,494,883 B1 | 12/2002 | Ferree |
| 6,506,192 B1 | 1/2003 | Gertzman et al. |
| 6,540,747 B1 | 4/2003 | Marino |
| 6,547,795 B2 | 4/2003 | Schneiderman |
| 6,565,605 B2 | 5/2003 | Goble et al. |
| 6,579,319 B2 | 6/2003 | Goble et al. |
| 6,610,091 B1 | 8/2003 | Reiley |
| 6,648,893 B2 | 11/2003 | Dudasik |
| 6,669,729 B2 | 12/2003 | Chin |
| 6,685,706 B2 | 2/2004 | Padget et al. |
| 6,740,093 B2 | 5/2004 | Hochschuler et al. |
| 6,811,567 B2 | 11/2004 | Reiley |
| 6,902,578 B1 | 6/2005 | Anderson et al. |
| 6,902,580 B2 | 6/2005 | Fallin et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,041,136 B2 | 5/2006 | Goble et al. |
| 7,051,451 B2 | 5/2006 | Augostino et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,074,237 B2 | 7/2006 | Goble et al. |
| 7,074,238 B2 | 7/2006 | Stinson et al. |
| 7,083,622 B2 | 8/2006 | Simonson |
| 7,087,084 B2 | 8/2006 | Reiley |
| 7,090,698 B2 | 8/2006 | Goble et al. |
| 7,094,239 B1 | 8/2006 | Michelson |
| 7,101,398 B2 | 9/2006 | Dooris et al. |
| 7,147,664 B2 | 12/2006 | Louis et al. |
| 7,220,262 B1 | 5/2007 | Hynes |
| 7,223,269 B2 | 5/2007 | Chappuis |
| 7,261,716 B2 | 8/2007 | Strobel et al. |
| 7,282,064 B2 | 10/2007 | Chin |
| 7,371,238 B2 | 5/2008 | Soboleski et al. |
| D574,495 S | 8/2008 | Petersen |
| 7,406,775 B2 | 8/2008 | Funk et al. |
| D581,538 S | 11/2008 | Horton |
| 7,445,635 B2 | 11/2008 | Fallin et al. |
| 7,452,369 B2 | 11/2008 | Barry |
| 7,491,236 B2 | 2/2009 | Cragg et al. |
| D589,626 S | 3/2009 | Petersen |
| D603,502 S | 11/2009 | Petersen |
| 7,699,878 B2 | 4/2010 | Pavlov et al. |
| 7,708,761 B2 | 5/2010 | Petersen |
| 7,708,766 B2 | 5/2010 | Anderson et al. |
| 7,837,713 B2 | 11/2010 | Petersen |
| 8,696,708 B2 | 4/2014 | Lechmann et al. |
| 2003/0088251 A1* | 5/2003 | Braun et al. .................... 606/73 |
| 2003/0208202 A1 | 11/2003 | Falahee |
| 2004/0006391 A1 | 1/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087948 A1 | 5/2004 | Suddaby |
| 2004/0127906 A1 | 7/2004 | Culbert et al. |
| 2004/0143268 A1 | 7/2004 | Falahee |
| 2004/0186475 A1 | 9/2004 | Falahee |
| 2004/0215344 A1 | 10/2004 | Hochschuler et al. |
| 2004/0230201 A1 | 11/2004 | Yuan et al. |
| 2004/0230304 A1 | 11/2004 | Yuan et al. |
| 2004/0254575 A1 | 12/2004 | Obenchain et al. |
| 2005/0015150 A1 | 1/2005 | Lee |
| 2005/0027361 A1 | 2/2005 | Reiley |
| 2005/0038438 A1 | 2/2005 | Anderson et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080486 A1 | 4/2005 | Fallin et al. |
| 2005/0085912 A1 | 4/2005 | Arnin et al. |
| 2005/0101953 A1 | 5/2005 | Simonson |
| 2005/0101954 A1 | 5/2005 | Simonson |
| 2005/0101956 A1 | 5/2005 | Simonson |
| 2005/0119748 A1 | 6/2005 | Reiley et al. |
| 2005/0124993 A1 | 6/2005 | Chappuis |
| 2005/0131405 A1 | 6/2005 | Molz, IV et al. |
| 2005/0131406 A1 | 6/2005 | Reiley et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149030 A1 | 7/2005 | Serhan et al. |
| 2005/0149190 A1 | 7/2005 | Reiley |
| 2005/0159746 A1 | 7/2005 | Grob et al. |
| 2005/0177240 A1 | 8/2005 | Blain |
| 2005/0197700 A1 | 9/2005 | Boehm, Jr. et al. |
| 2005/0203625 A1 | 9/2005 | Boehm et al. |
| 2005/0209694 A1 | 9/2005 | Loeb |
| 2005/0234552 A1 | 10/2005 | Reiley |
| 2005/0240188 A1 | 10/2005 | Chow et al. |
| 2005/0240264 A1 | 10/2005 | Tokish, Jr. et al. |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267480 A1 | 12/2005 | Suddaby |
| 2005/0267579 A1 | 12/2005 | Reiley et al. |
| 2005/0273167 A1 | 12/2005 | Triplett et al. |
| 2005/0277921 A1 | 12/2005 | Eisermann et al. |
| 2005/0277930 A1 | 12/2005 | Parsons |
| 2005/0277938 A1 | 12/2005 | Parsons |
| 2005/0283238 A1 | 12/2005 | Reiley |
| 2006/0004367 A1 | 1/2006 | Alamin et al. |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0009849 A1 | 1/2006 | Reiley |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1 | 3/2006 | Pavlov et al. |
| 2006/0079896 A1 | 4/2006 | Kwak et al. |
| 2006/0084976 A1 | 4/2006 | Borgstrom et al. |
| 2006/0085075 A1 | 4/2006 | McLeer |
| 2006/0100707 A1 | 5/2006 | Stinson et al. |

(56) References Cited

U.S. PATENT DOCUMENTS

| | | |
|---|---|---|
| 2006/0100709 A1 | 5/2006 | Reiley |
| 2006/0111779 A1 | 5/2006 | Petersen |
| 2006/0111780 A1 | 5/2006 | Petersen |
| 2006/0111781 A1 | 5/2006 | Petersen |
| 2006/0111782 A1 | 5/2006 | Petersen |
| 2006/0122612 A1* | 6/2006 | Justin et al. ............ 606/73 |
| 2006/0129239 A1 | 6/2006 | Kwak |
| 2006/0149229 A1 | 7/2006 | Kwak et al. |
| 2006/0149230 A1 | 7/2006 | Kwak et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0184180 A1 | 8/2006 | Augostino et al. |
| 2006/0190081 A1 | 8/2006 | Kraus et al. |
| 2006/0200137 A1 | 9/2006 | Soboleski et al. |
| 2006/0200149 A1 | 9/2006 | Hoy et al. |
| 2006/0212034 A1 | 9/2006 | Triplett et al. |
| 2006/0217718 A1 | 9/2006 | Chervitz et al. |
| 2006/0235391 A1 | 10/2006 | Sutterlin, III |
| 2006/0235414 A1 | 10/2006 | Lim et al. |
| 2006/0241597 A1 | 10/2006 | Mitchell et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247769 A1 | 11/2006 | Molz et al. |
| 2006/0259142 A1 | 11/2006 | Dooris et al. |
| 2006/0264954 A1 | 11/2006 | Sweeney, II et al. |
| 2006/0265069 A1 | 11/2006 | Goble et al. |
| 2006/0265070 A1 | 11/2006 | Stinson et al. |
| 2006/0271046 A1 | 11/2006 | Kwak et al. |
| 2006/0271195 A1 | 11/2006 | Thramann |
| 2006/0276790 A1 | 12/2006 | Dawson et al. |
| 2006/0282080 A1 | 12/2006 | Albert et al. |
| 2007/0005137 A1 | 1/2007 | Kwak |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0016296 A1 | 1/2007 | Triplett et al. |
| 2007/0016297 A1 | 1/2007 | Johnson |
| 2007/0030221 A1 | 2/2007 | Pak et al. |
| 2007/0035795 A1 | 2/2007 | Hubbard |
| 2007/0055236 A1 | 3/2007 | Hudgins et al. |
| 2007/0055245 A1 | 3/2007 | Sasso et al. |
| 2007/0055257 A1 | 3/2007 | Vaccaro et al. |
| 2007/0055373 A1 | 3/2007 | Hudgins et al. |
| 2007/0073290 A1 | 3/2007 | Boehm, Jr. |
| 2007/0073396 A1 | 3/2007 | Arnin |
| 2007/0079517 A1 | 4/2007 | Augostino et al. |
| 2007/0083266 A1 | 4/2007 | Lang |
| 2007/0088358 A1 | 4/2007 | Yuan et al. |
| 2007/0088440 A1 | 4/2007 | Eisermann et al. |
| 2007/0093833 A1 | 4/2007 | Kuiper et al. |
| 2007/0112428 A1 | 5/2007 | Lancial |
| 2007/0118218 A1 | 5/2007 | Hooper |
| 2007/0118224 A1 | 5/2007 | Shah et al. |
| 2007/0123863 A1 | 5/2007 | Winslow et al. |
| 2007/0123891 A1 | 5/2007 | Ries et al. |
| 2007/0123892 A1 | 5/2007 | Ries et al. |
| 2007/0135814 A1 | 6/2007 | Farris |
| 2007/0149976 A1 | 6/2007 | Hale et al. |
| 2007/0149983 A1 | 6/2007 | Link |
| 2007/0156237 A1 | 7/2007 | Kwak |
| 2007/0167946 A1 | 7/2007 | Triplett et al. |
| 2007/0168029 A1 | 7/2007 | Yuan et al. |
| 2007/0168035 A1 | 7/2007 | Koske |
| 2007/0179617 A1 | 8/2007 | Brown et al. |
| 2007/0179619 A1 | 8/2007 | Grob et al. |
| 2007/0185492 A1 | 8/2007 | Chervitz et al. |
| 2007/0185576 A1 | 8/2007 | Goble et al. |
| 2007/0198091 A1 | 8/2007 | Boyer et al. |
| 2007/0227547 A1 | 10/2007 | Trieu |
| 2007/0233092 A1 | 10/2007 | Falahee |
| 2007/0233093 A1 | 10/2007 | Falahee |
| 2007/0233256 A1 | 10/2007 | Ohrt et al. |
| 2007/0244483 A9 | 10/2007 | Winslow et al. |
| 2007/0250166 A1 | 10/2007 | McKay |
| 2007/0255224 A1 | 11/2007 | Ahern et al. |
| 2007/0255411 A1 | 11/2007 | Reiley |
| 2007/0265706 A1 | 11/2007 | Reiley |
| 2007/0270967 A1 | 11/2007 | Fallin et al. |
| 2007/0276374 A1 | 11/2007 | Broman et al. |
| 2007/0282445 A1 | 12/2007 | Reiley |
| 2008/0015583 A1 | 1/2008 | Reiley |
| 2008/0015585 A1 | 1/2008 | Berg et al. |
| 2008/0015696 A1 | 1/2008 | Reiley |
| 2008/0021457 A1 | 1/2008 | Anderson et al. |
| 2008/0027543 A1 | 1/2008 | Eisermann et al. |
| 2008/0045954 A1 | 2/2008 | Reiley et al. |
| 2008/0065076 A1 | 3/2008 | Cragg et al. |
| 2008/0125855 A1 | 5/2008 | Henkes et al. |
| 2008/0200953 A1 | 8/2008 | Reiley et al. |
| 2008/0208249 A1 | 8/2008 | Blain et al. |
| 2008/0208341 A1 | 8/2008 | McCormack et al. |
| 2008/0221622 A1 | 9/2008 | Triplett et al. |
| 2008/0221692 A1 | 9/2008 | Zucherman et al. |
| 2008/0234735 A1 | 9/2008 | Joshi |
| 2008/0234758 A1 | 9/2008 | Fisher et al. |
| 2008/0249568 A1 | 10/2008 | Kuiper et al. |
| 2008/0249571 A1 | 10/2008 | Sasso et al. |
| 2008/0255618 A1 | 10/2008 | Fisher et al. |
| 2008/0255619 A1 | 10/2008 | Schneiderman et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0262545 A1 | 10/2008 | Simonson |
| 2008/0262555 A1 | 10/2008 | Assell et al. |
| 2008/0269897 A1 | 10/2008 | Joshi |
| 2008/0275505 A1 | 11/2008 | Yuan et al. |
| 2008/0275507 A1 | 11/2008 | Triplett et al. |
| 2008/0287959 A1 | 11/2008 | Quest et al. |
| 2008/0287996 A1 | 11/2008 | Soboleski et al. |
| 2008/0292161 A1 | 11/2008 | Funk et al. |
| 2008/0306537 A1 | 12/2008 | Culbert |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0005818 A1 | 1/2009 | Chin et al. |
| 2009/0012566 A1 | 1/2009 | Fauth |
| 2009/0018585 A1 | 1/2009 | Reiley |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0024219 A1 | 1/2009 | McLeer |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036927 A1 | 2/2009 | Vestgaarden |
| 2009/0076551 A1 | 3/2009 | Petersen |
| 2009/0082868 A1 | 3/2009 | Cordaro et al. |
| 2009/0105819 A1 | 4/2009 | Barry |
| 2009/0234397 A1 | 9/2009 | Petersen |
| 2009/0270929 A1 | 10/2009 | Suddaby |
| 2011/0004247 A1 | 1/2011 | Lechmann |

FOREIGN PATENT DOCUMENTS

| | | |
|---|---|---|
| WO | WO 00/04851 | 2/2000 |
| WO | WO 2004/043278 | 5/2004 |
| WO | WO 2006/023683 | 3/2006 |
| WO | WO 2007/120903 | 10/2007 |
| WO | WO 2008/106240 | 9/2008 |

(56) References Cited

FOREIGN PATENT DOCUMENTS

| | | |
|---|---|---|
| WO | WO 2009/111632 | 9/2009 |
| WO | WO 2009/148619 | 12/2009 |
| WO | WO 2012/006627 | 1/2012 |

OTHER PUBLICATIONS

International Patent Application No. PCT/US2011/043579: International Search Report dated Oct. 25, 2011, 5 pages.

U.S. Appl. No. 61/363,077, filed Jul. 9, 2010, Angert et al.

* cited by examiner

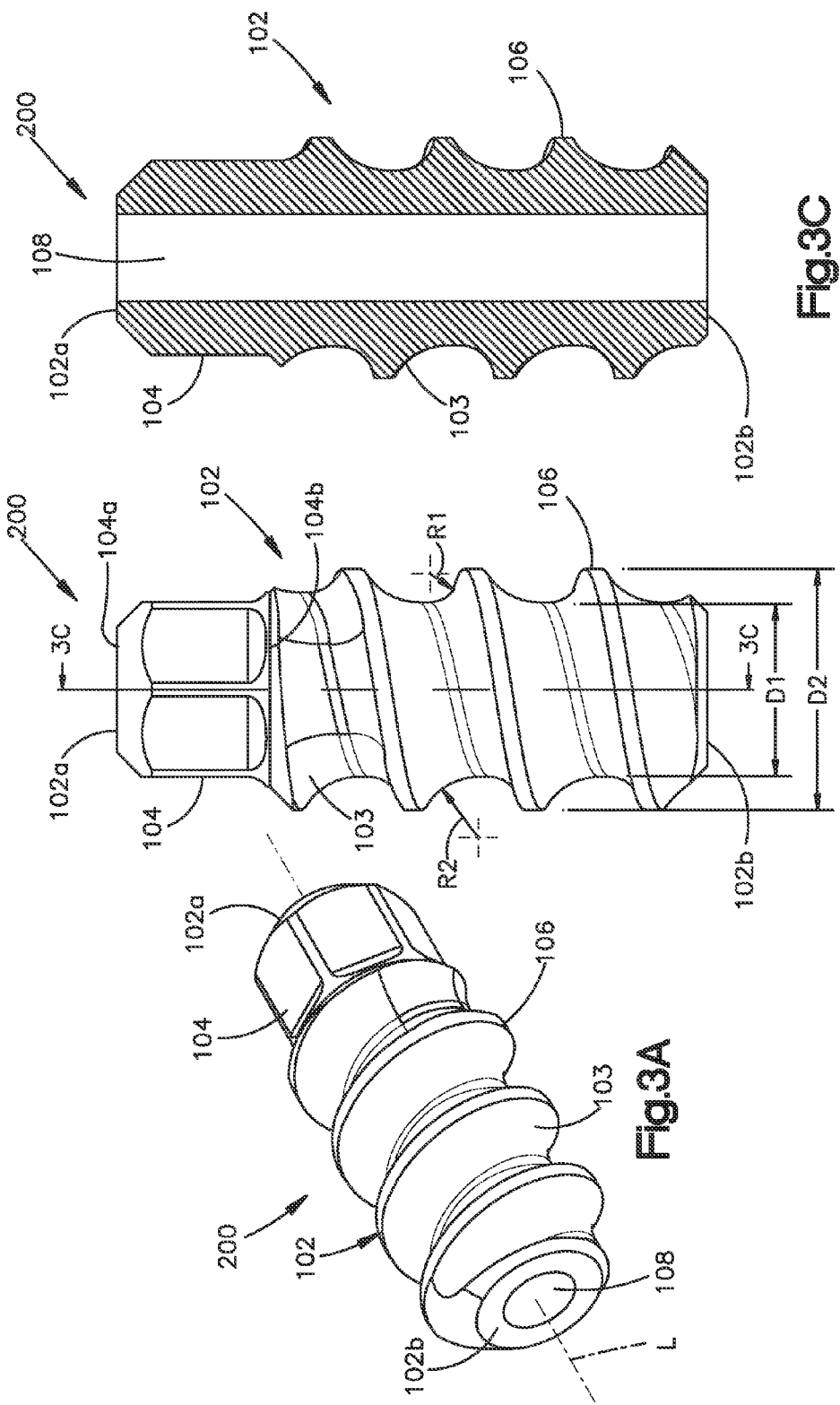

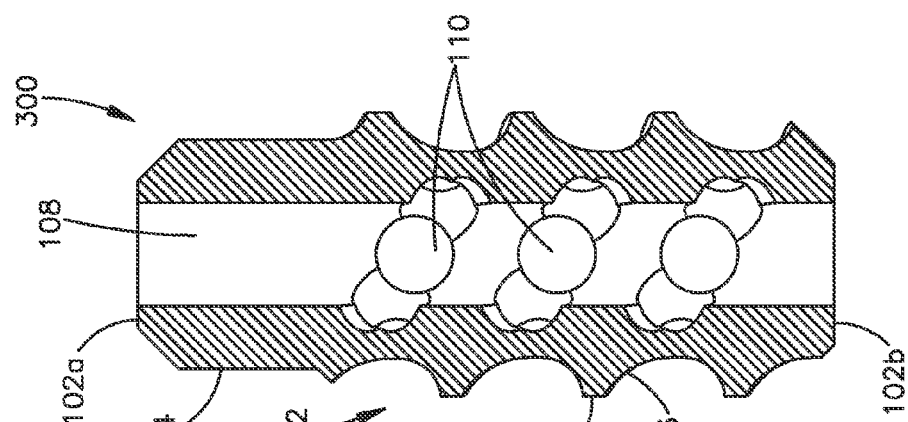
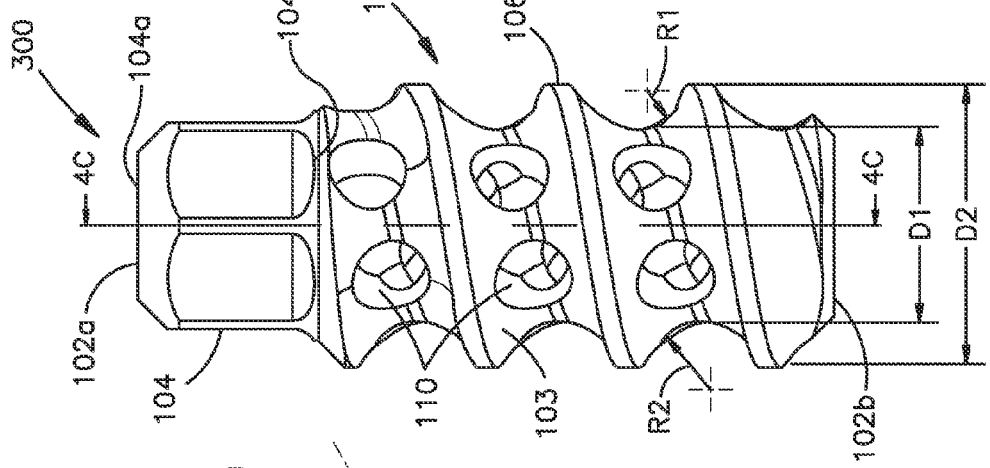
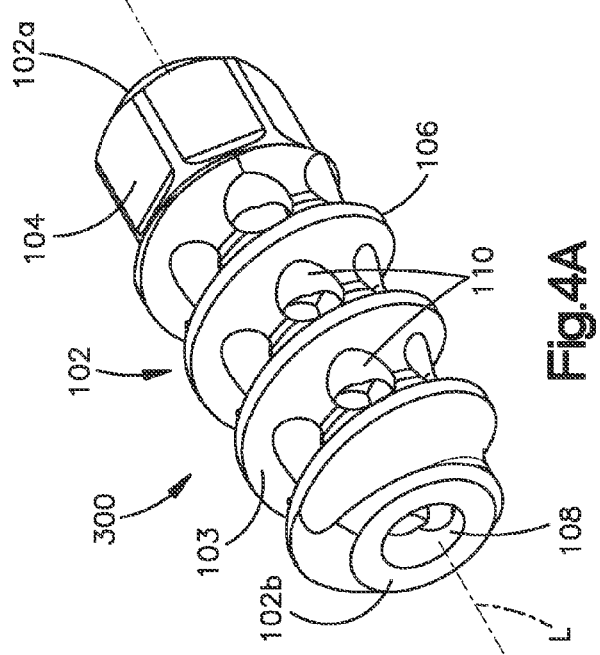
Fig.4C
Fig.4B
Fig.4A

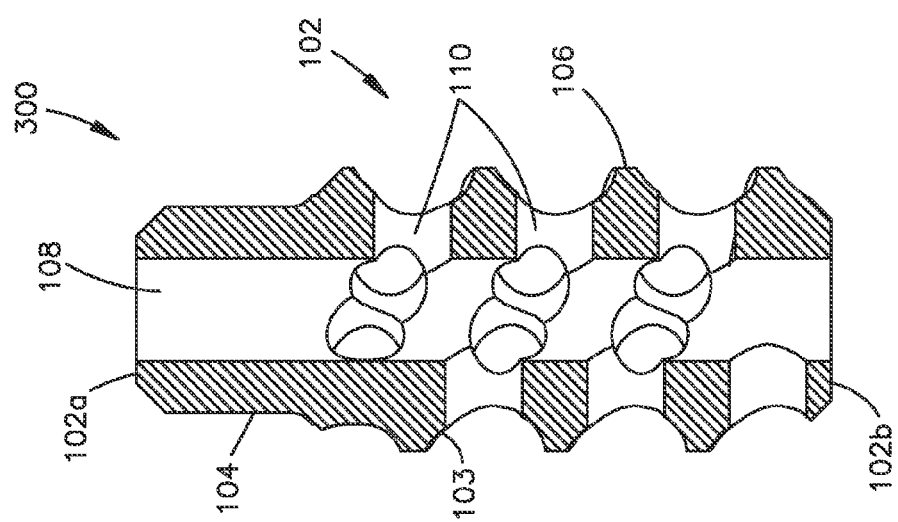
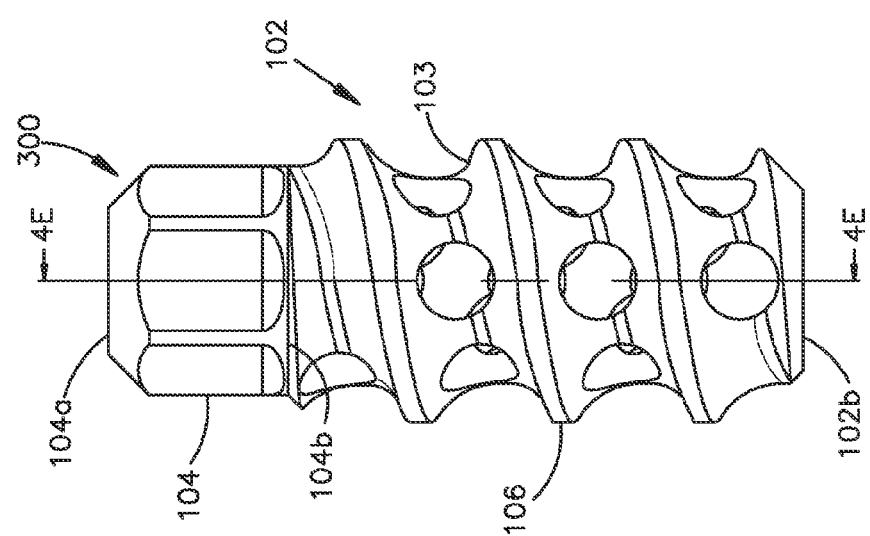
Fig. 4D
Fig. 4E

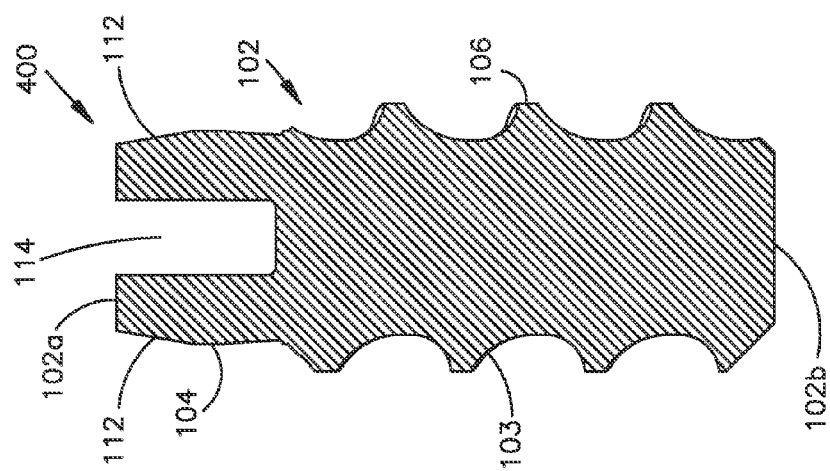
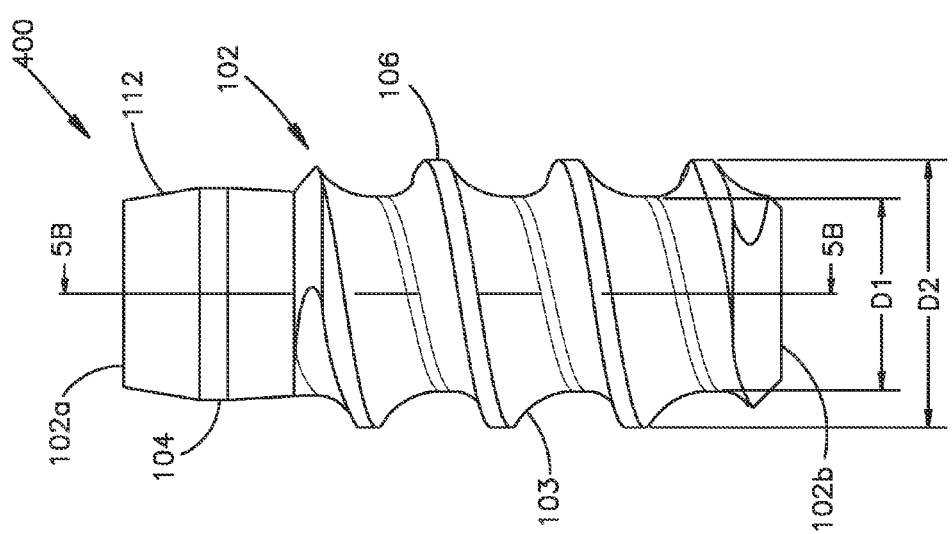

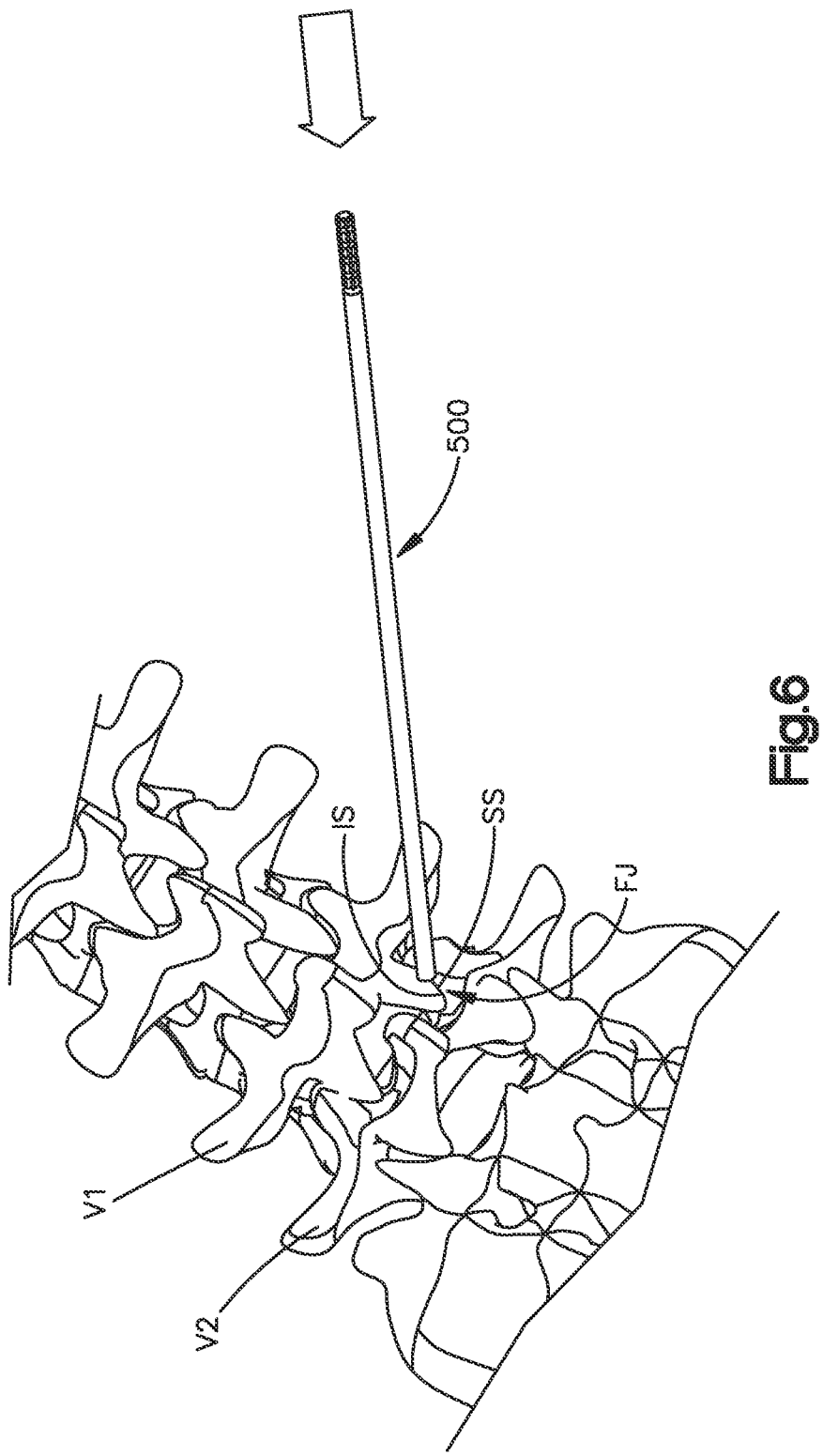

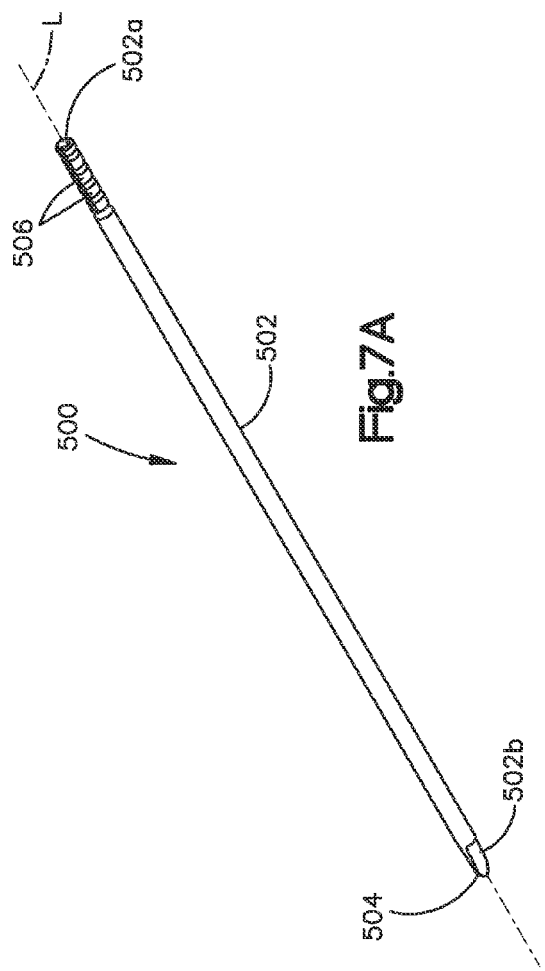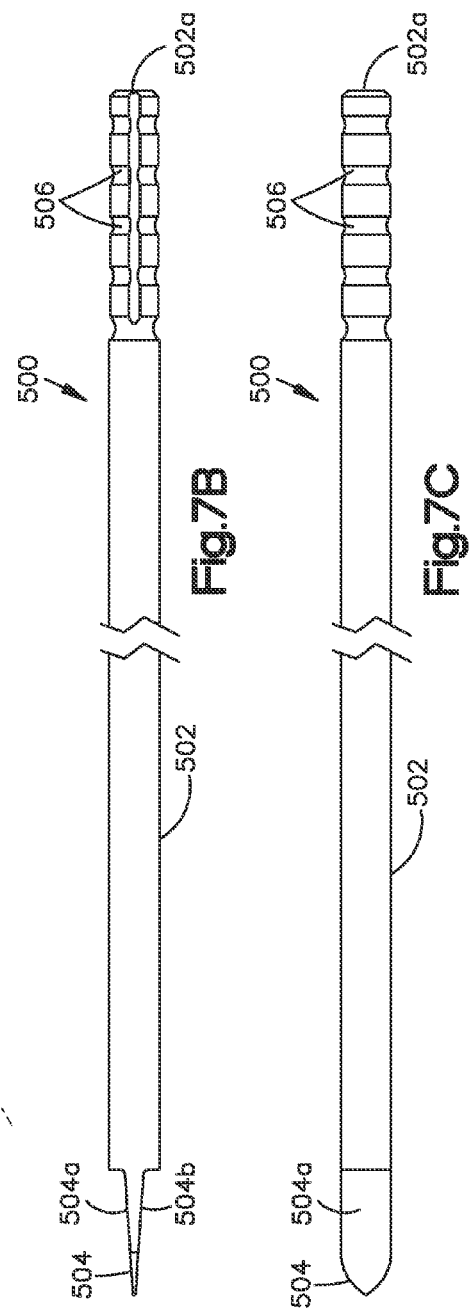

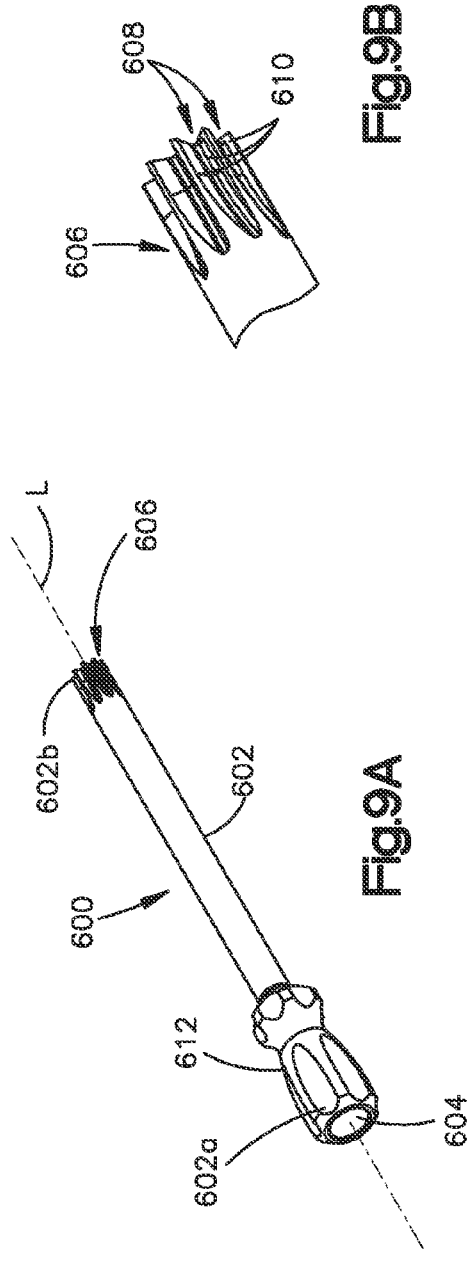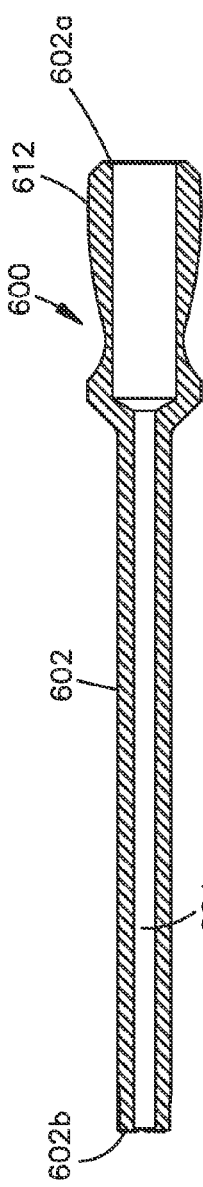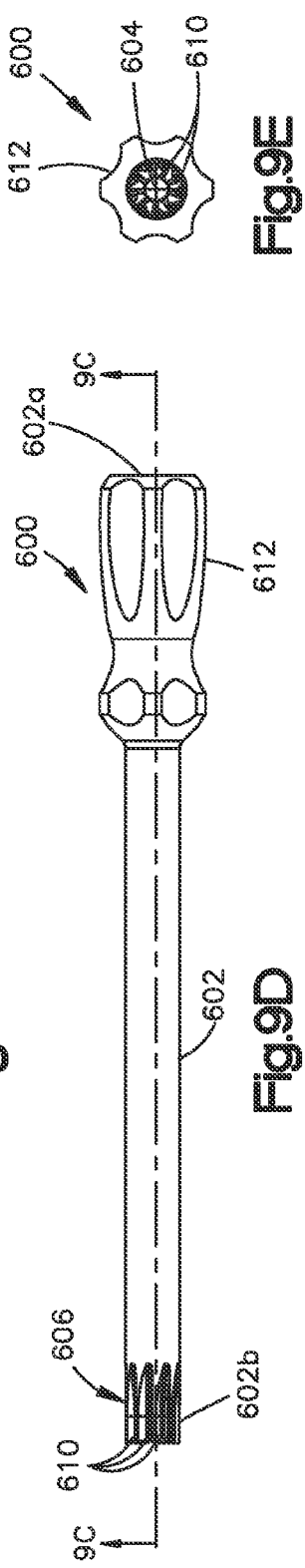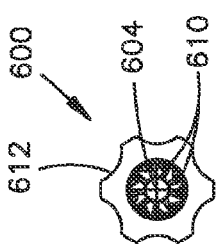

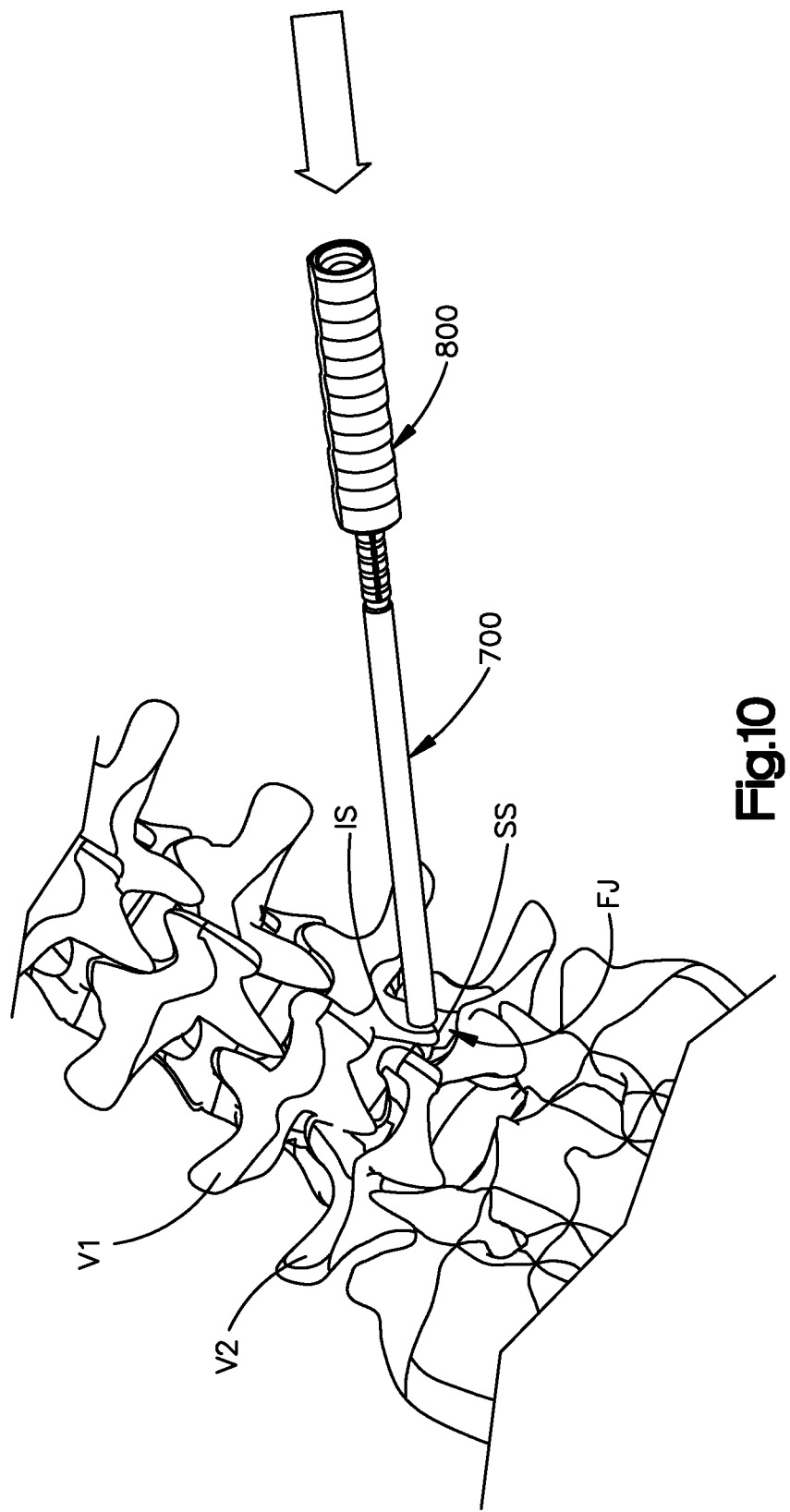

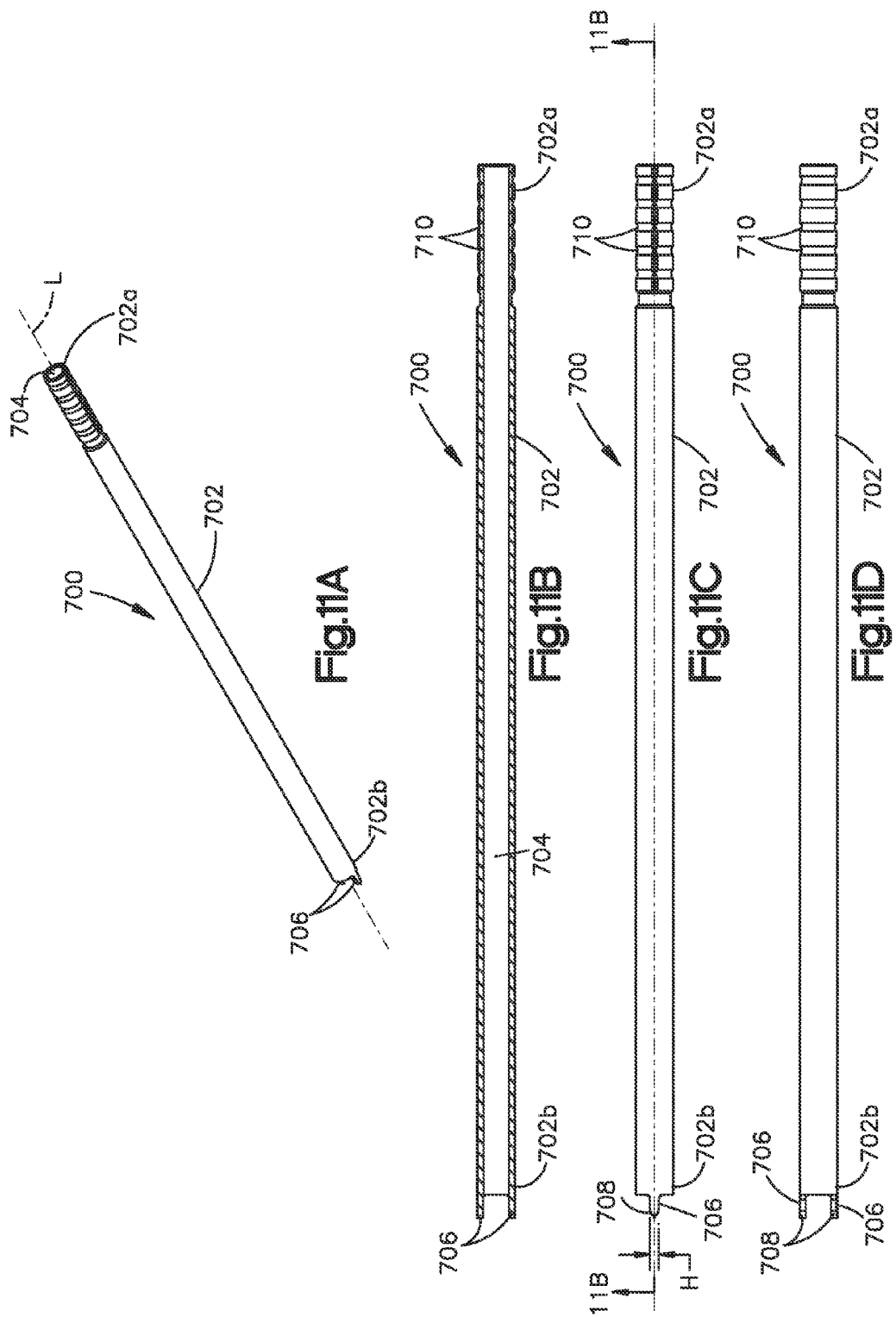

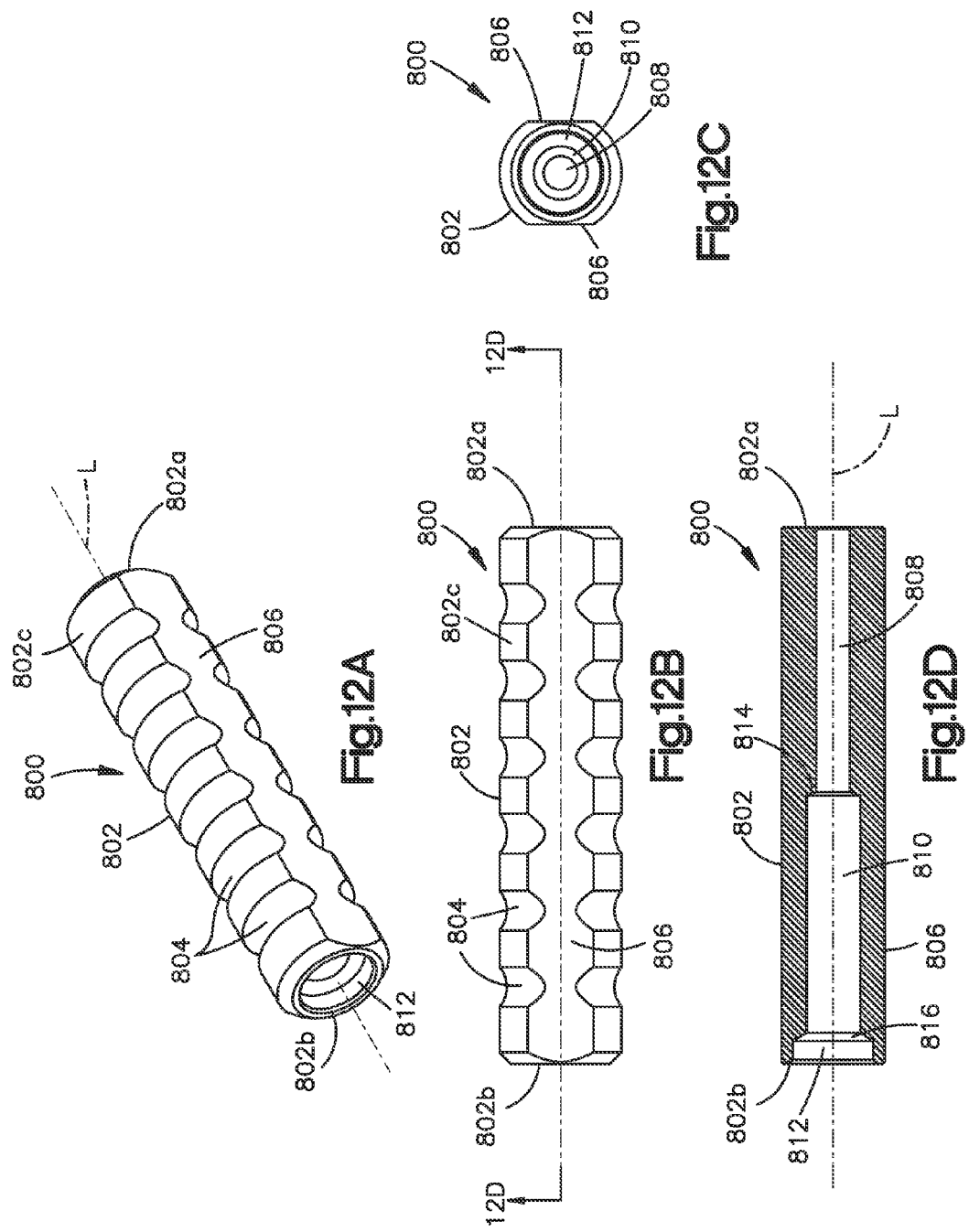

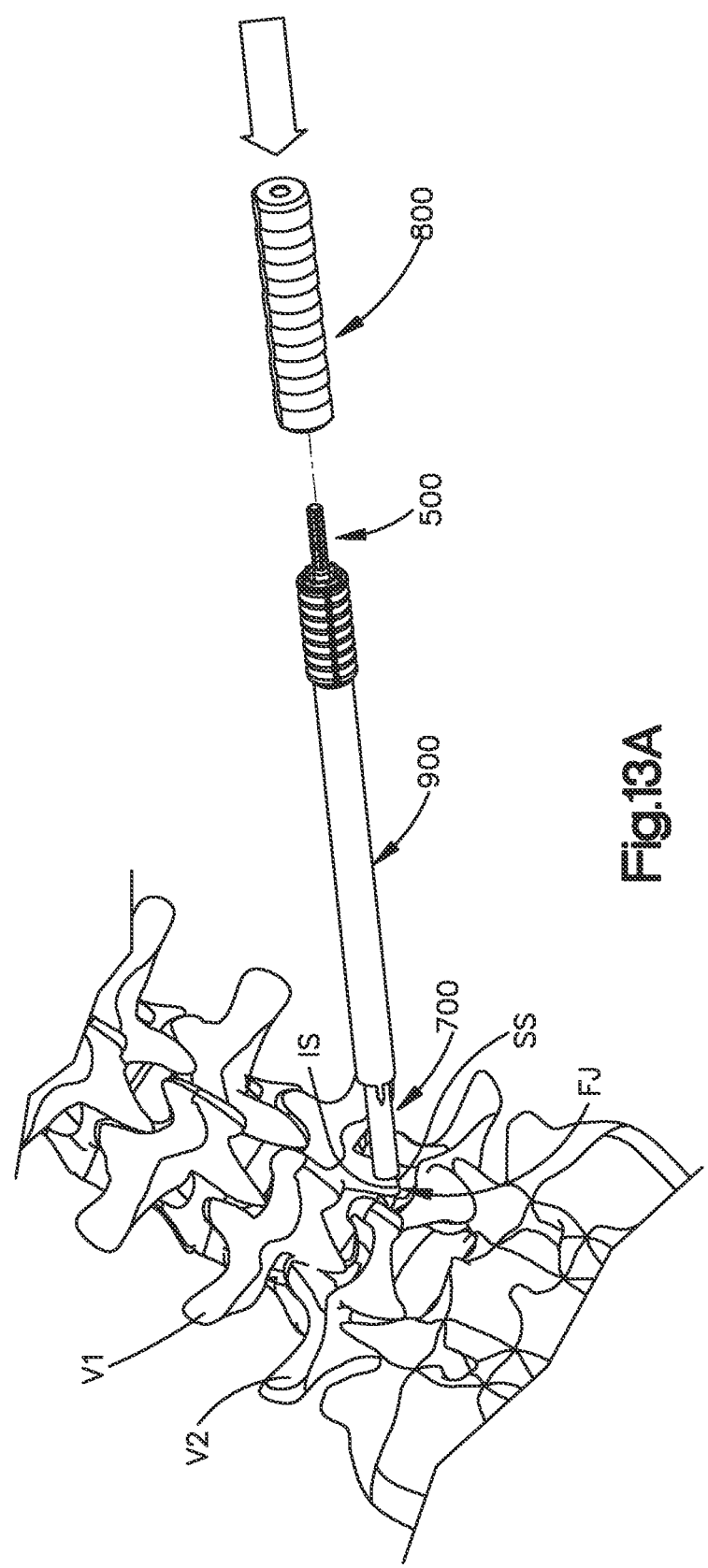

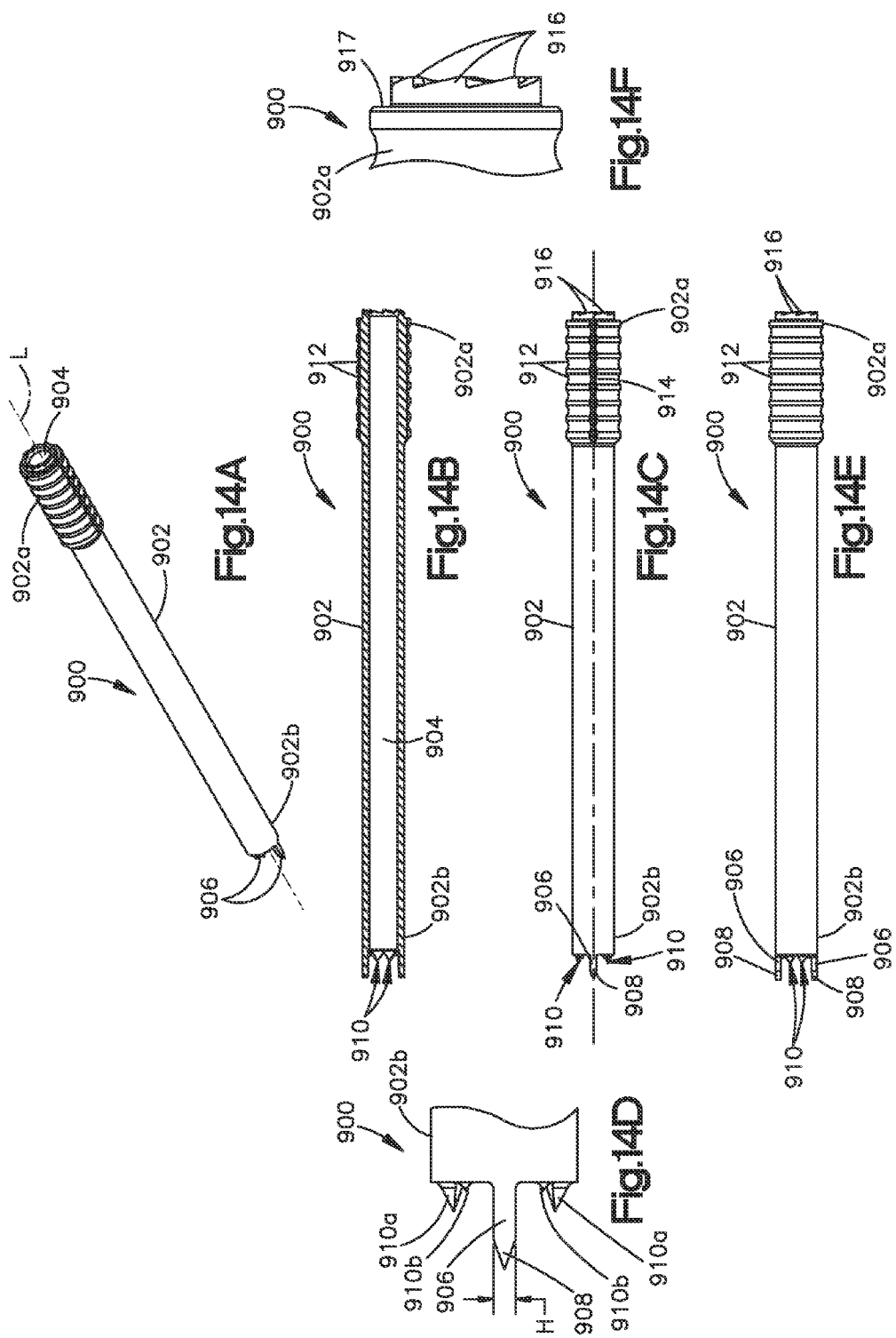

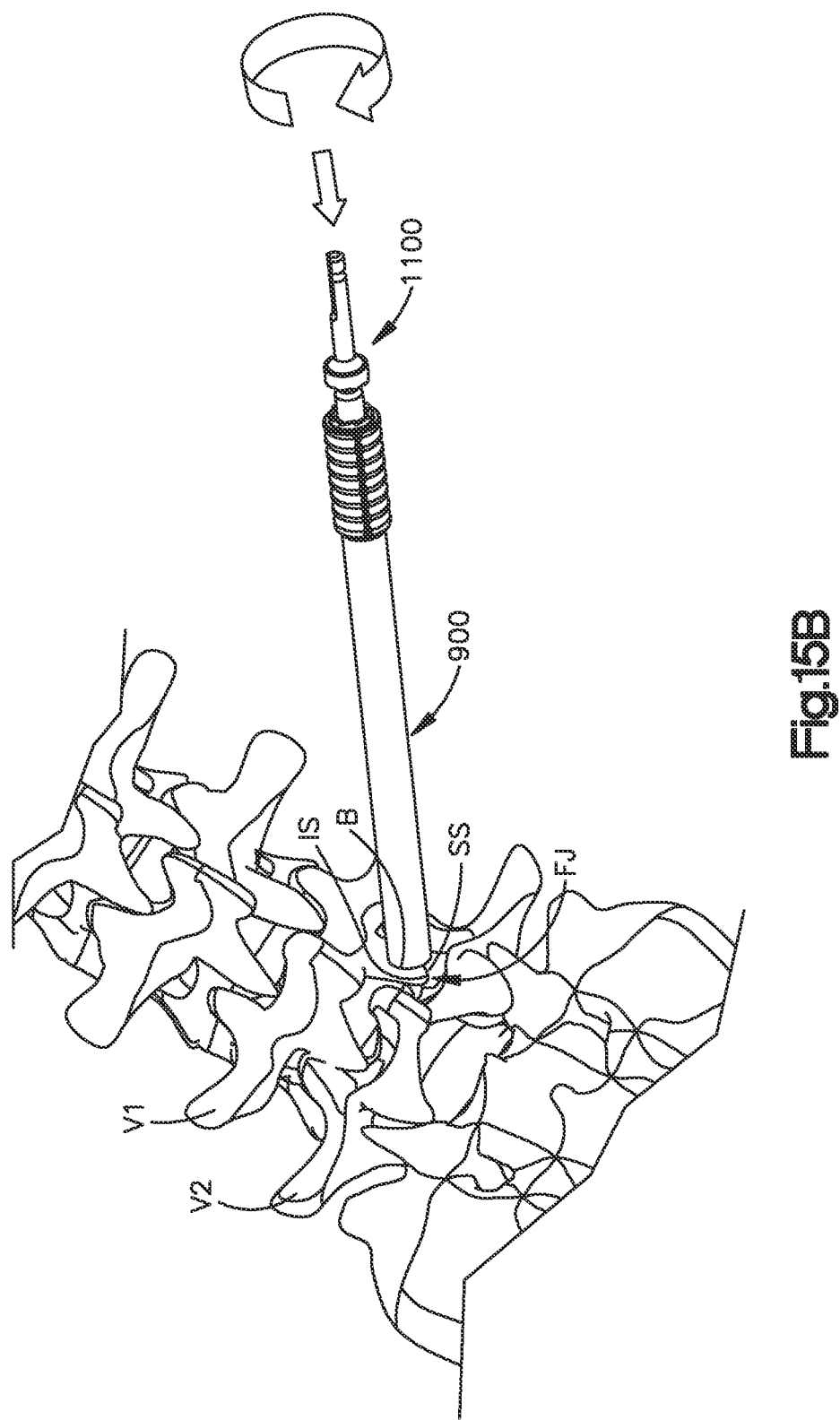

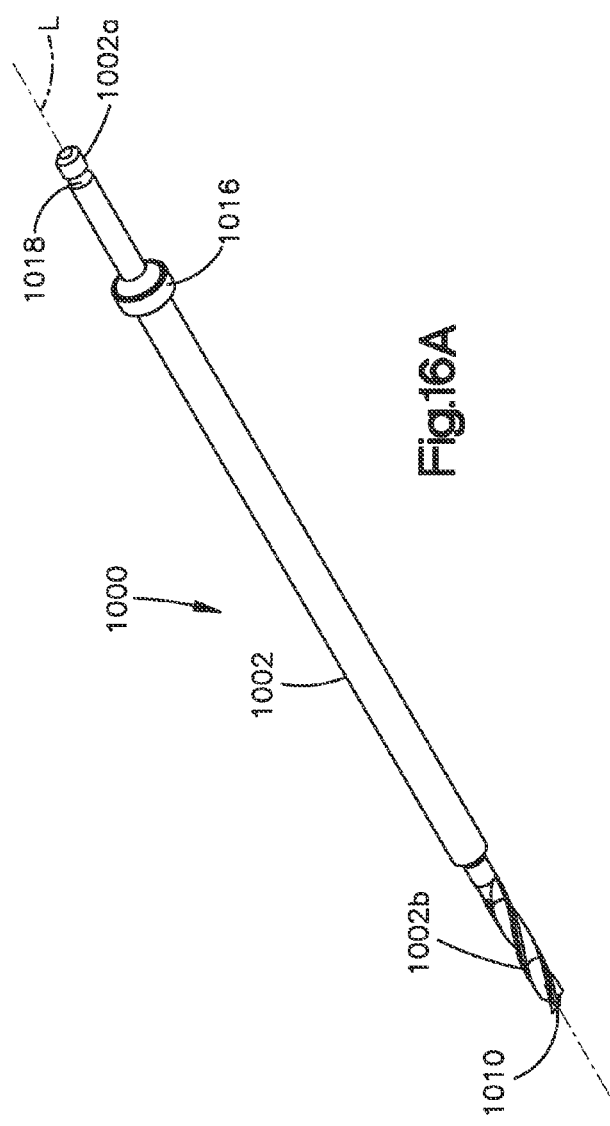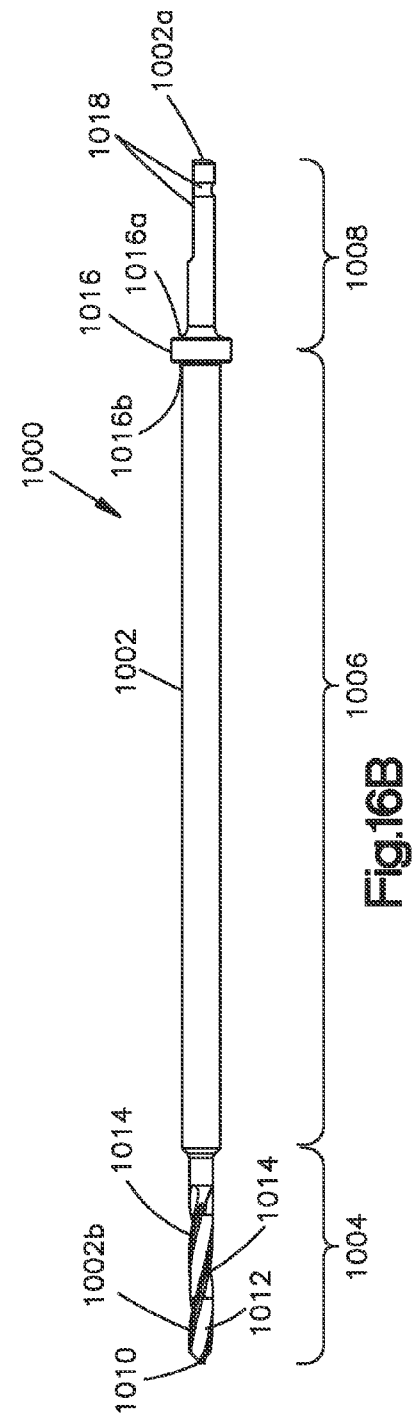

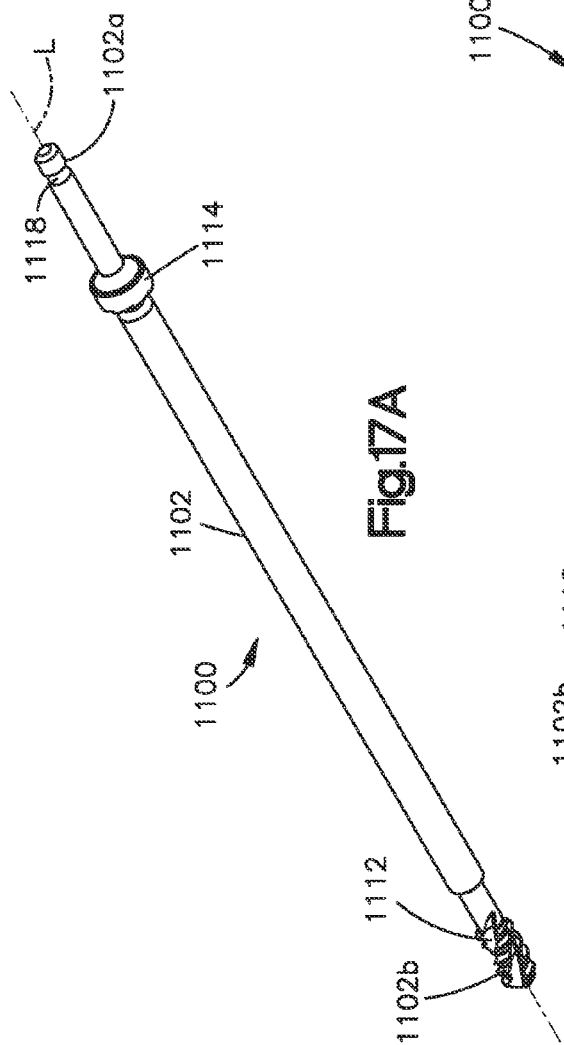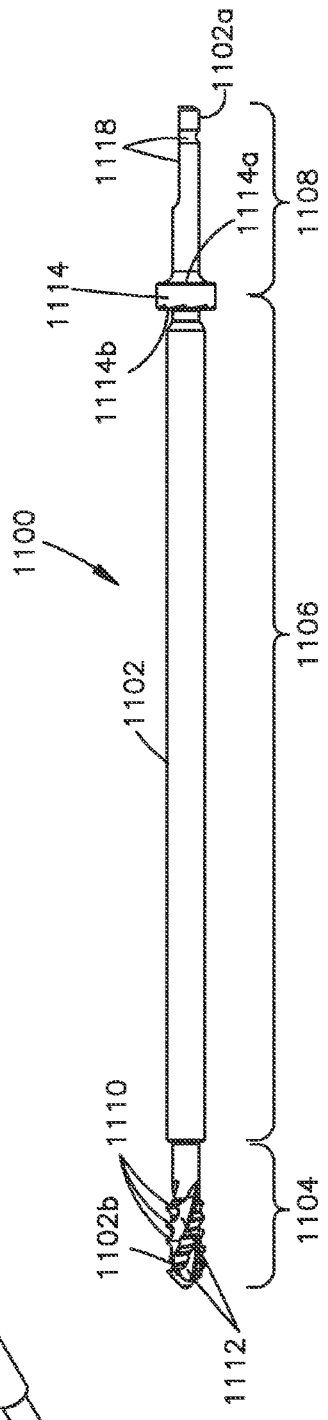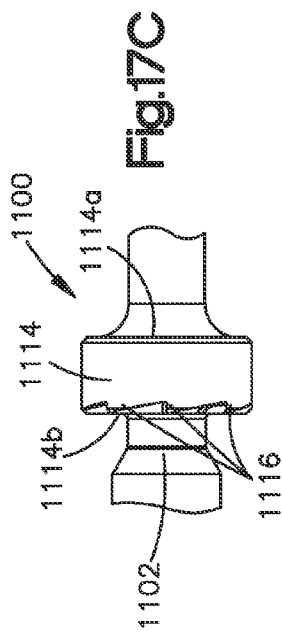

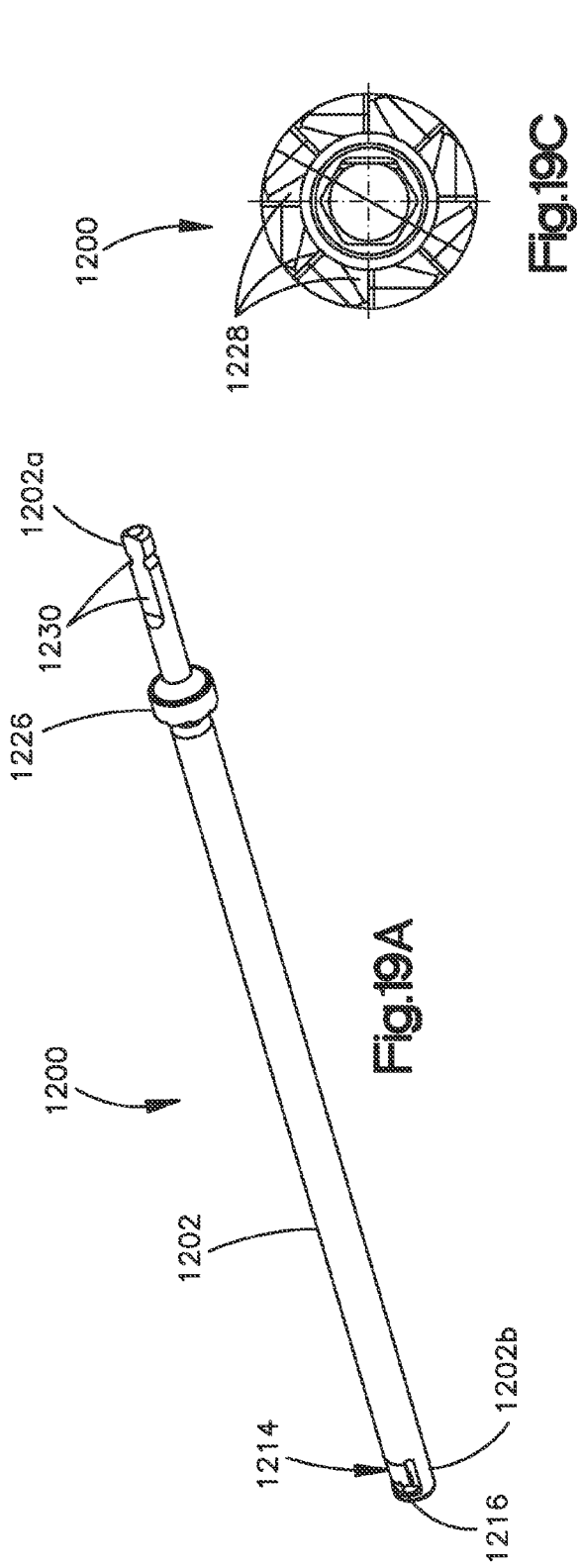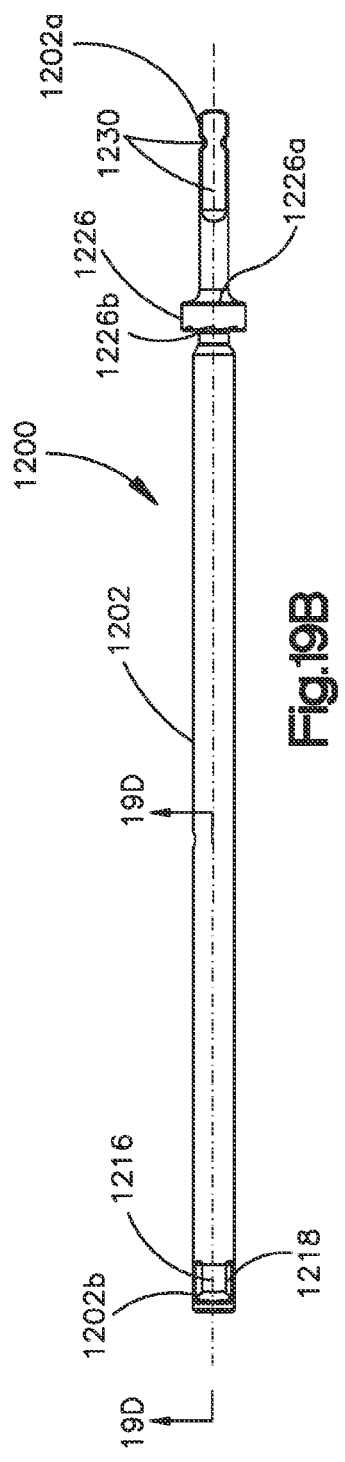

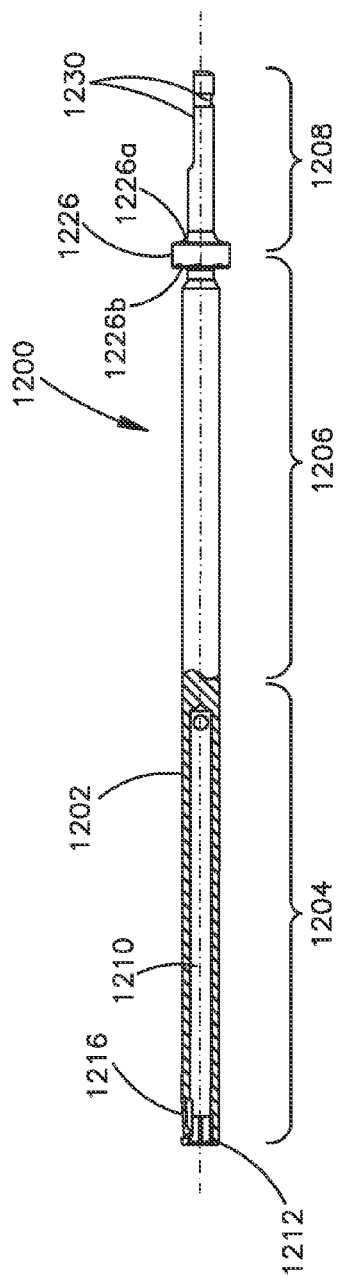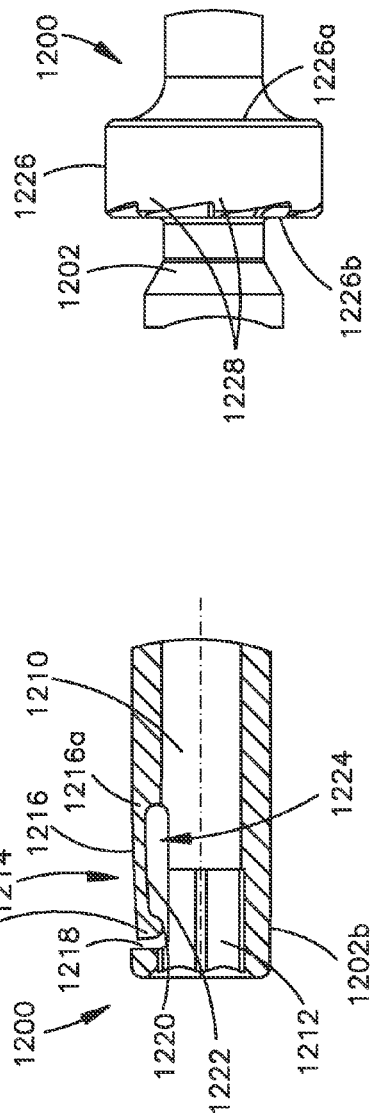

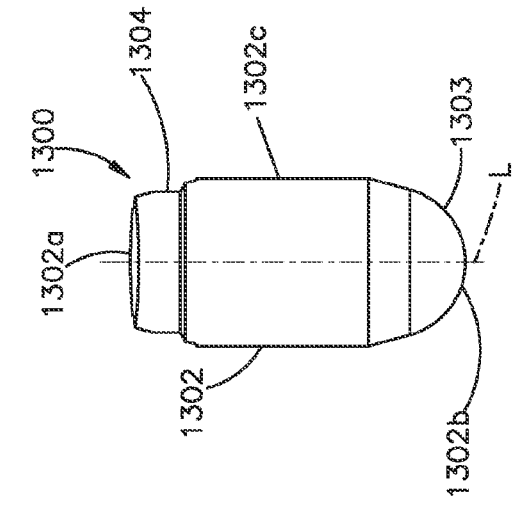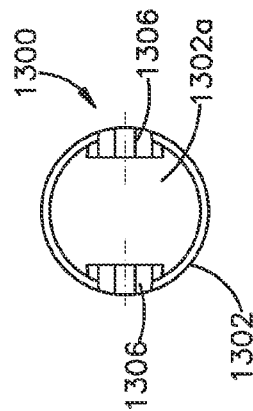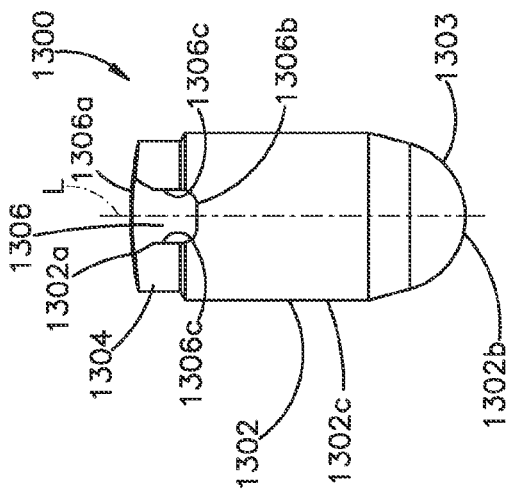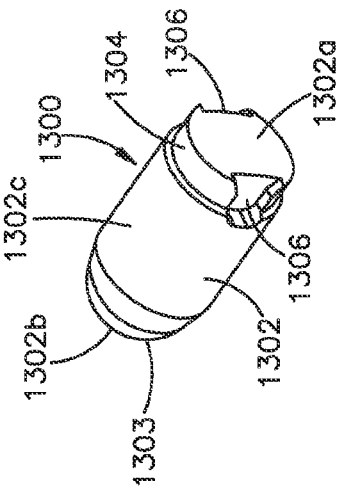

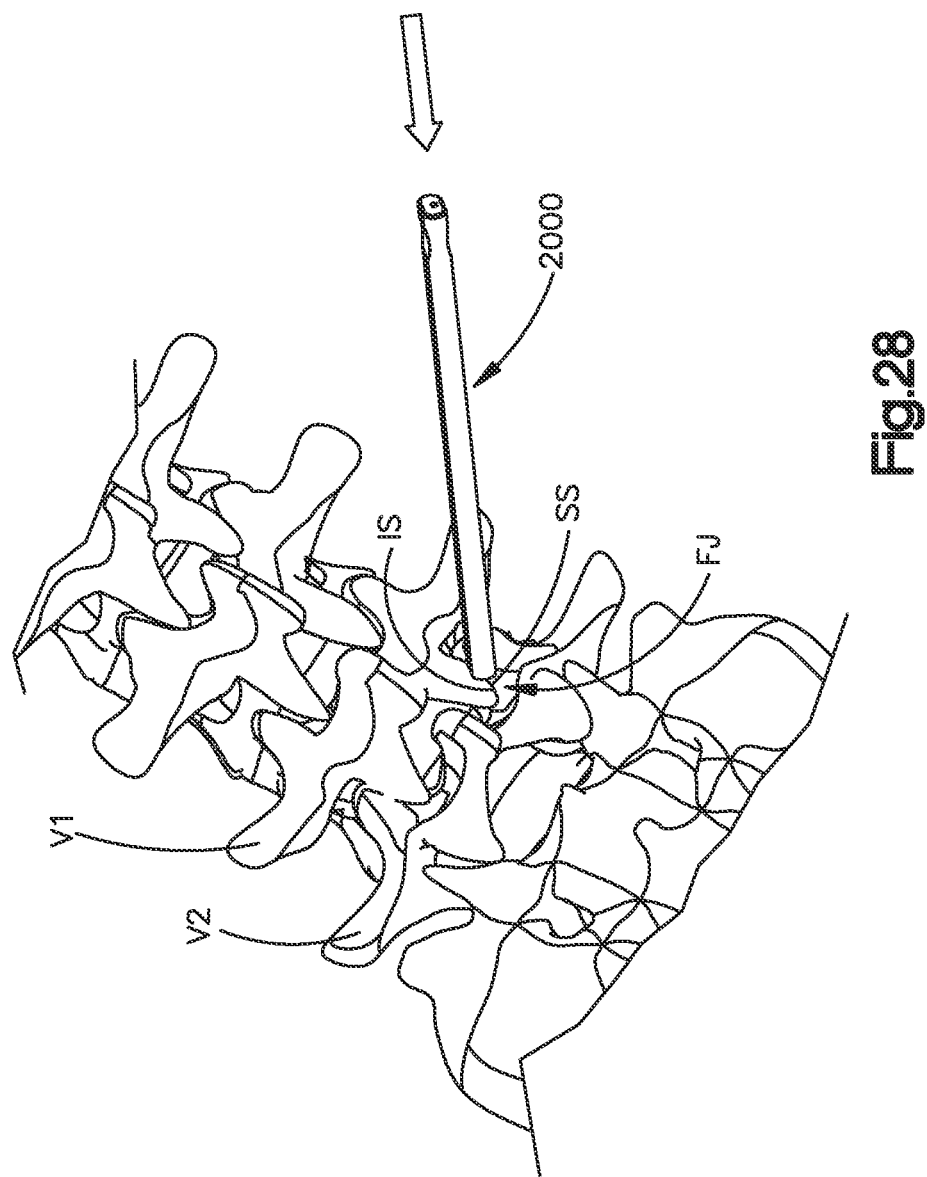

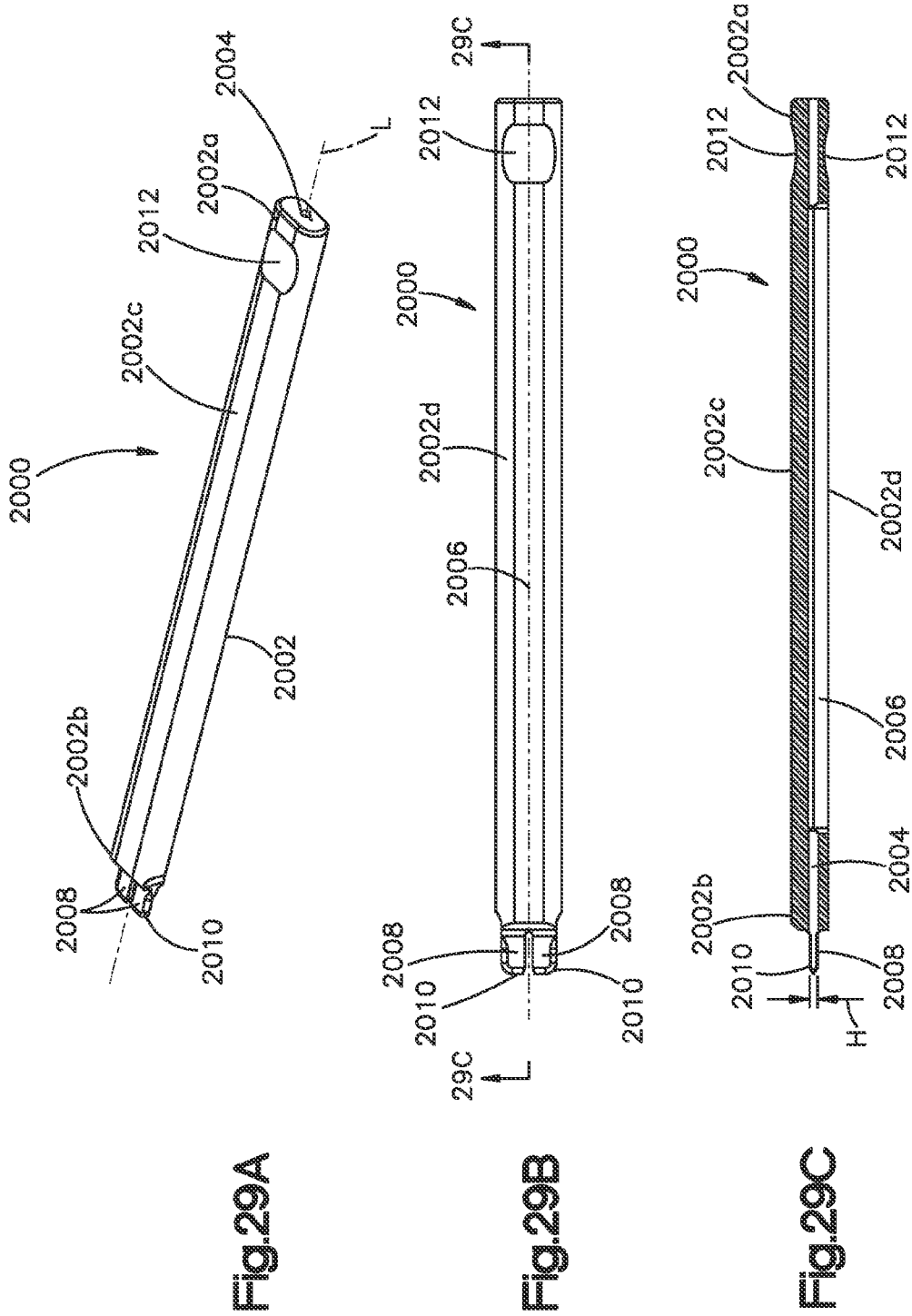

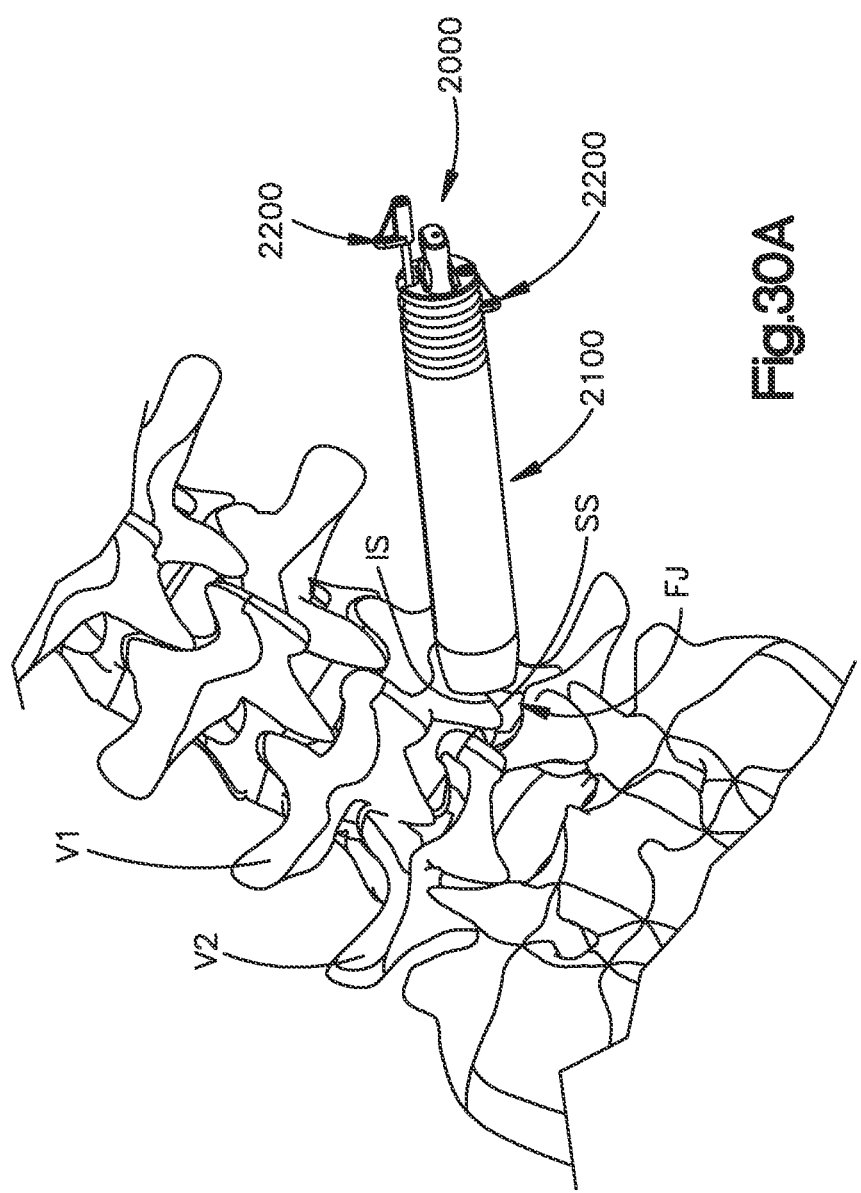

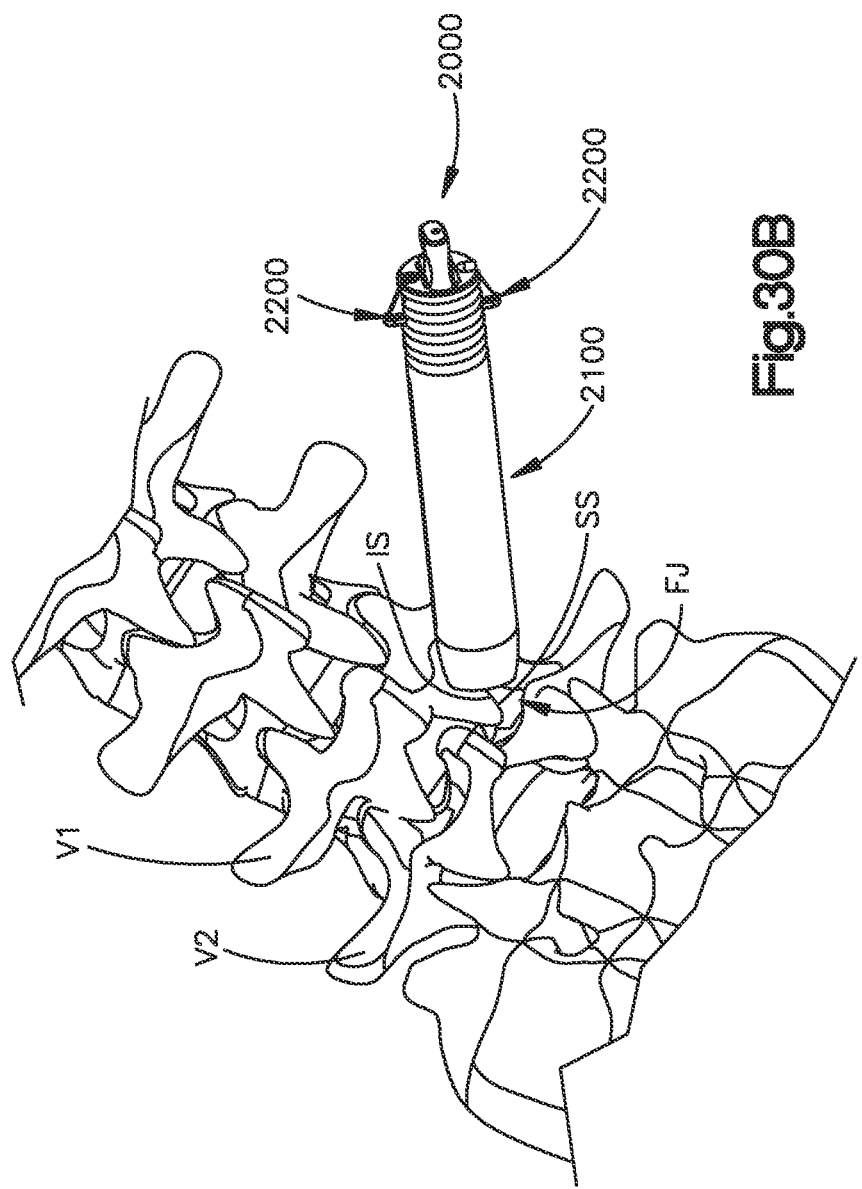

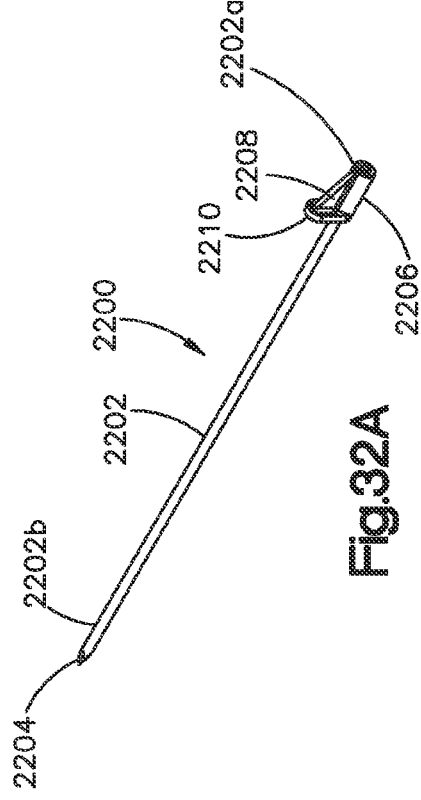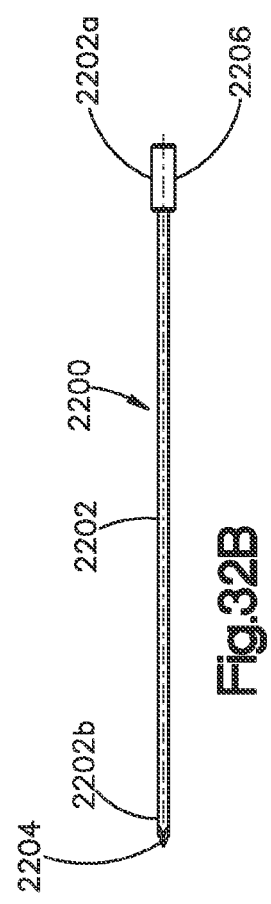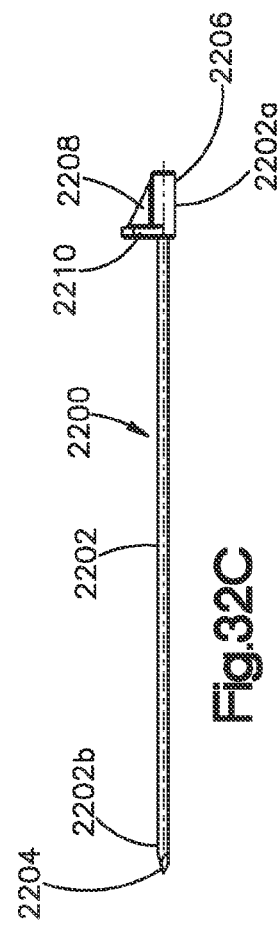

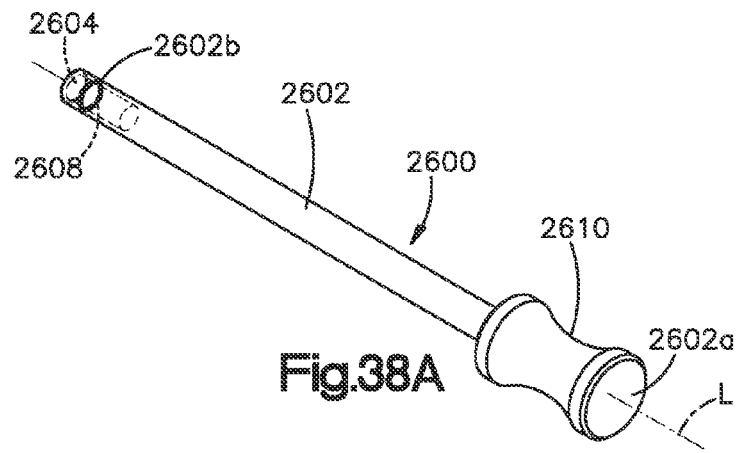
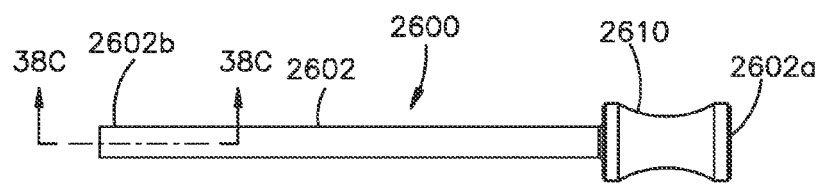
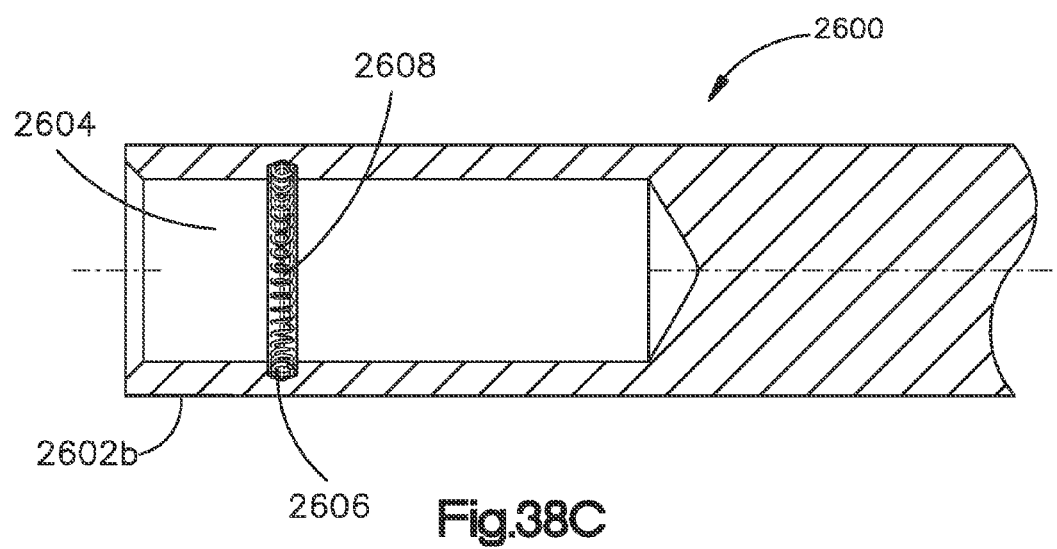

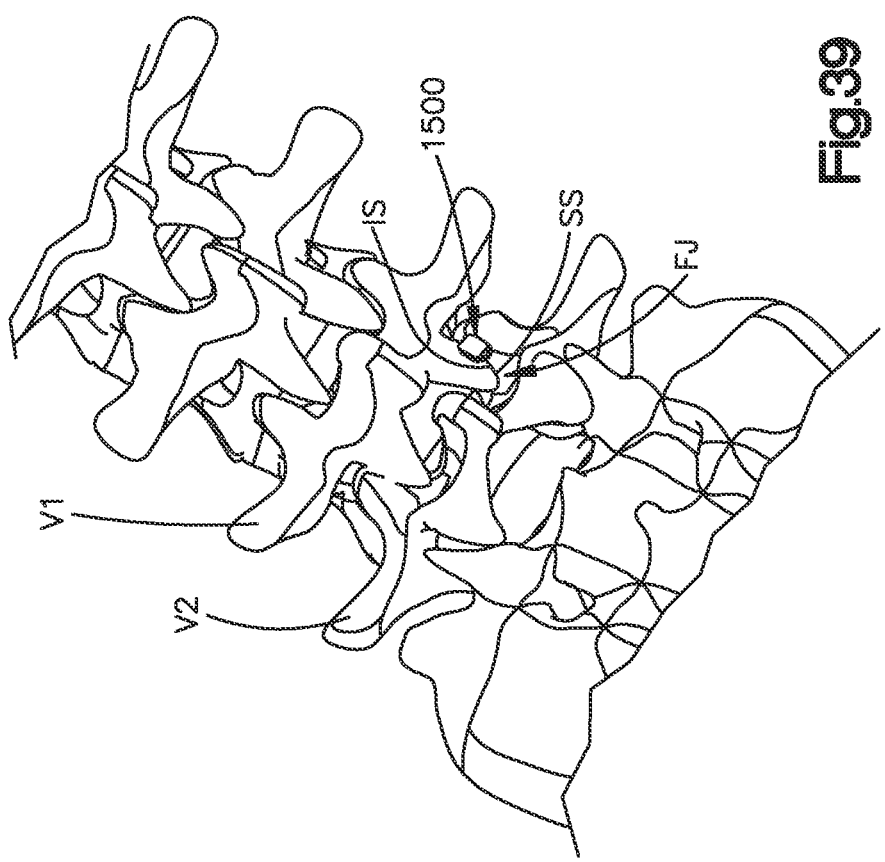

US 8,986,355 B2

FACET FUSION IMPLANT

CROSS-REFERENCE TO RELATED APPLICATIONS

This patent application claims priority to U.S. patent application No. 61/363,077, filed Jul. 9, 2010, which is incorporated herein by reference in its entirety.

BACKGROUND

The vertebrae in a patient's spinal column are linked to one another by the intervertebral disc and the facet joints. This three joint complex controls the movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebrae form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to reduce pain coming from the three joint complex. In the lumbar spine, for example, one form of treatment to stabilize the spine and to relieve pain involves the fusion of the facet joint.

One known technique for stabilizing and treating the facet joint involves a trans-facet fusion in which pins, screws or bolts penetrate the lamina to fuse the joint. Such a technique has associated with it the risk of further injury to the patient as such translaminar facet instrumentation can be difficult to place in such a way that it does not violate the spinal canal and/or contact the dura of the spinal cord or the nerve root ganglia. Further, trans-facet instrumentation has been known to create a rotational distortion, lateral offset, hyper-lordosis, and/or intervertebral foraminal stenosis as the screws tend to compress the facet joint together.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances these implants can result in some degree of foraminal stenosis as the screws tend to compress the facet joints together.

SUMMARY

In accordance with one embodiment, a facet fusion implant includes an implant body elongate along a central axis. The implant body includes a head portion disposed at a proximal end of the implant body and a shaft portion that extends distally from the head portion toward a distal end of the implant body. The head portion defines a first cross-sectional dimension that does not exceed a second cross-sectional dimension of the shaft portion. The first and second cross-sectional dimensions substantially perpendicular to the central axis. The shaft portion of the implant body is configured to simultaneously engage opposed first and second vertebral articulation surfaces of a facet joint. The facet fusion implant further includes an engaging element carried by the head portion. The engaging element is configured to engage with a complementary insertion instrument configured to insert the facet fusion implant into the facet joint between the first and second vertebral articulation surfaces.

In accordance with a second embodiment, a method for inserting an implant into a facet joint includes the step of locating a facet joint defined by a superior articulation surface of a first vertebra and an inferior articulation surface of a second vertebra. The method further includes the step of preparing an insertion path between the superior and inferior articulation surfaces. The insertion path is configured to receive the implant therein. The method further includes the step of inserting the implant into an inserted position in the facet joint by transmitting a rotational force to the implant.

BRIEF DESCRIPTION OF THE DRAWINGS

The foregoing summary, as well as the following detailed description of the preferred embodiments of the application, will be better understood when read in conjunction with the appended drawings. For the purposes of illustrating the facet fusion implant, there are shown in the drawings preferred embodiments. It should be understood, however, that the instant application is not limited to the precise arrangements and/or instrumentalities illustrated in the drawings, in which:

FIG. 3A is a perspective view of a facet fusion implant constructed in accordance with an alternative embodiment;

FIG. 3B is a side elevation view of the implant illustrated in FIG. 3A;

FIG. 3C is a side section view of the implant illustrated in FIG. 3A;

FIG. 4A is a perspective view of a facet fusion implant constructed in accordance with another alternative embodiment;

FIG. 4B is a side elevation view of the implant illustrated in FIG. 4A from a first perspective;

FIG. 4C is a side section view of the implant illustrated in FIG. 4A from the first perspective of FIG. 4B;

FIG. 4D is a side elevation view of the implant illustrated in FIG. 4A from a second perspective;

FIG. 4E is a side section view of the implant illustrated in FIG. 4A from the second perspective of FIG. 4D;

FIG. 5A is a side elevation view of a facet fusion implant constructed in accordance with yet another alternative embodiment;

FIG. 5B is a side section view of the implant illustrated in FIG. 5A;

FIG. 6 is a perspective view of a guide pin inserted into a facet joint;

FIG. 7A is a perspective view of the guide pin illustrated in FIG. 6;

FIG. 7B is a side elevation view of the guide pin illustrated in FIG. 6;

FIG. 7C is a top elevation view of the guide pin illustrated in FIG. 6;

FIG. 9A is a perspective view of the reamer illustrated in FIG. 8;

FIG. 9B is a zoomed in perspective view of a portion of the reamer illustrated in FIG. 9A;

FIG. 9C is a side section view of the reamer illustrated in FIG. 9A;

FIG. 9D is a side elevation view of the reamer illustrated in FIG. 9A;

FIG. 9E is a front elevation view of the reamer illustrated in FIG. 9A;

FIG. 10 is a perspective view of a joint finder and an impaction cap inserted over the guide pin illustrated in FIG. 6;

FIG. 11A is a perspective view of the joint finder illustrated in FIG. 10;

FIG. 11B is a top section view of the joint finder illustrated in FIG. 11A;

FIG. 11C is a side elevation view of the joint finder illustrated in FIG. 11A;

FIG. 11D is a top elevation view of the joint finder illustrated in FIG. 11A;

FIG. 12A is a perspective view of the impaction cap illustrated in FIG. 10;

FIG. 12B is a top elevation view of the impaction cap illustrated in FIG. 12A;

FIG. 12C is a rear elevation view of the impaction cap illustrated in FIG. 12A;

FIG. 12D is a side section view of the impaction cap illustrated in FIG. 12A;

FIG. 14A is a perspective view of the guide tube illustrated in FIG. 13;

FIG. 14B is a top section view of the guide tube illustrated in FIG. 14A;

FIG. 14C is a side elevation view of the guide tube illustrated in FIG. 14A;

FIG. 14D is a zoomed in side elevation view of a portion of the guide tube illustrated in FIG. 14A;

FIG. 14E is a top elevation view of the guide tube illustrated in FIG. 14A;

FIG. 14F is a zoomed in side elevation view of a portion of the guide tube illustrated in FIG. 14A;

FIG. 15B is a perspective view of a tap inserted through the guide tube illustrated in FIG. 14A and into the facet joint;

FIG. 16A is a perspective view of the drill bit illustrated in FIG. 15A;

FIG. 16B is a side elevation view of the drill bit illustrated in FIG. 16A;

FIG. 17A is a perspective view of the tap illustrated in FIG. 15B;

FIG. 17B is a side elevation view of the tap illustrated in FIG. 17A;

FIG. 17C is a zoomed in side elevation view of a portion of the tap illustrated in FIG. 17A;

FIG. 19A is a perspective view of the driver shaft illustrated in FIG. 18;

FIG. 19B is a top elevation view of the driver shaft illustrated in FIG. 19A;

FIG. 19C is a front elevation view of the driver shaft illustrated in FIG. 19A;

FIG. 19D is a partial side section view of driver shaft illustrated in FIG. 19A;

FIG. 19E is a zoomed in side section view of a portion of the driver shaft illustrated in FIG. 19A;

FIG. 19F is a zoomed in side elevation view of a portion of the driver shaft illustrated in FIG. 19A;

FIG. 21A is a side elevation view of a facet fusion implant constructed in accordance with yet another alternative embodiment;

FIG. 21B is a top elevation view of the implant illustrated in FIG. 21A;

FIG. 21C is a perspective view of the implant illustrated in FIG. 21A;

FIG. 21D is a rear elevation view of the implant illustrated in FIG. 21A;

FIG. 28 is a perspective view of a facet finder inserted into a facet joint;

FIG. 29A is a perspective view of the facet finder illustrated in FIG. 28;

FIG. 29B is a bottom elevation view of the facet finder illustrated in FIG. 29A;

FIG. 29C is a side section view of the facet finder illustrated in FIG. 29A;

FIG. 30A is a perspective view of a guide tube inserted over the facet finder illustrated in FIG. 28, with a pair of fixation pins partially inserted into the guide tube;

FIG. 30B is a perspective view of the guide tube inserted over the facet finder illustrated in FIG. 30A, with the fixation pins fully inserted into the guide tube;

FIG. 32A is a perspective view of the fixation pin illustrated in FIG. 30A;

FIG. 32B is a bottom elevation view of the fixation pin illustrated in FIG. 32A;

FIG. 32C is a side elevation view of the fixation pin illustrated in FIG. 32A;

FIG. 38A is a perspective view of the tamping inserter illustrated in FIG. 36A;

FIG. 38B is a side elevation view of the tamping inserter illustrated in FIG. 38A;

FIG. 38C is a zoomed in side section view of a portion of the tamping inserter illustrated in FIG. 38A;

FIG. 39 is a perspective view of the implant illustrated in FIGS. 23A-D inserted into the facet joint;

DETAILED DESCRIPTION

Figure 1:
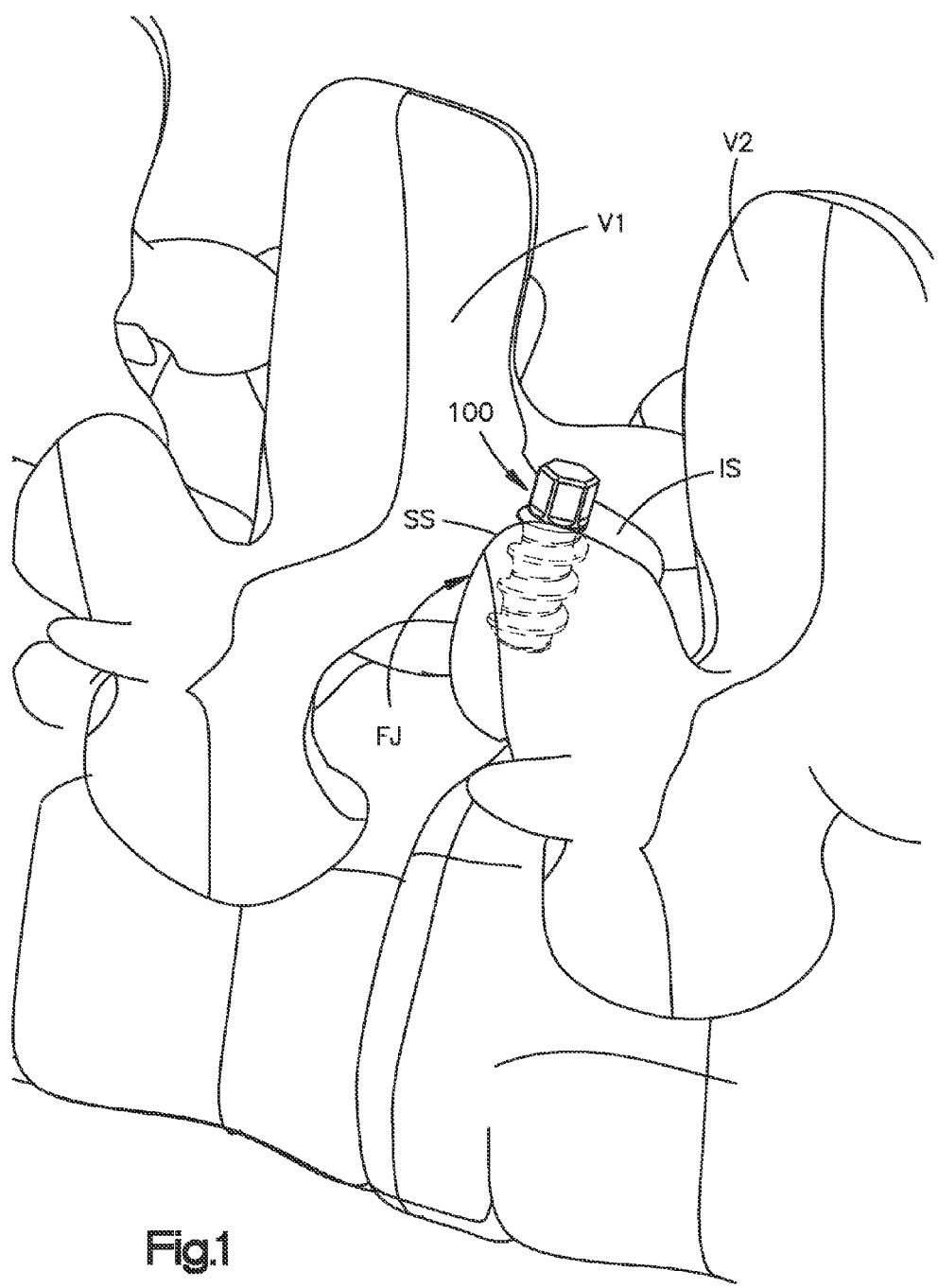
FIG. 1 is a perspective view of a facet fusion implant constructed in accordance with an embodiment inserted into a facet joint.

For convenience, the same or equivalent elements in the various embodiments illustrated in the drawings have been identified with the same reference numerals. Certain terminology is used in the following description for convenience only and is not limiting. The words "right," "left," "upper," and "lower" designate directions in the drawings to which reference is made. The words "inner," "inward," "inwardly," "outer," "outward," "outwardly," "upward," "upwardly," "downward," and "downwardly" refer to directions toward and away from, respectively, the geometric center of the object referred to and designated parts thereof. The words "anterior," "posterior," "superior," and "inferior" designate preferred positions and/or orientations in the human body to which reference is made. The terminology intended to be non-limiting includes the above-listed words, derivatives thereof and words of similar import.

Referring initially to FIG. 1, a facet fusion implant 100 inserted into a facet joint FJ is illustrated. The facet fusion implant 100 is configured to be inserted into the facet joint FJ by application of a rotational force to the implant 100 (i.e., the implant 100 is driven, or screwed into the facet joint FJ). When inserted into the facet joint FJ, the implant 100 can promote fusion across the facet joint FJ. The facet joint FJ can be defined as the gap between the inferior articulation surface IS on one side of a first vertebra V1 and the superior articulation surface SS on the same side of a second vertebra V2. The implant 100 can be inserted into the facet joint FJ such that the implant 100 engages the bony surfaces of the inferior and superior articulation surface IS, SS, respectively, so as to immobilize movement of the first and second vertebrae V1, V2 with respect to each other about the facet joint FJ, thereby facilitating the promotion of localized facet joint fusion between the first and second vertebrae V1, V2. It should be appreciated that while FIG. 1 illustrates a single facet fusion implant 100 inserted into the facet joint FJ on the left side of a patient's spine, that a second implant 100 could be inserted into the facet joint between the first and second vertebrae V1, V2 on the right side of the patient's spine, if desired.

The implant 100 is preferably constructed of allograft tissue, such as allograft bone. The allograft bone can be at least partially demineralized in order to enhance the osteoinductive potential of the implant 100, thereby enhancing its fusion promoting characteristics. For example, in accordance with the illustrated embodiment, the implant 100 can be surface demineralized. It should be appreciated that the implant 100 is not limited to being constructed of allograft bone, and that the implant 100 can alternatively be constructed using any other biocompatible, implantable material as desired, including metals such as titanium, titanium alloy such as Ti-6Al-7Nb, or stainless steel, polymers such as polyetheretherketone (PEEK), reinforced plastics, and the like.

Figure 2C:
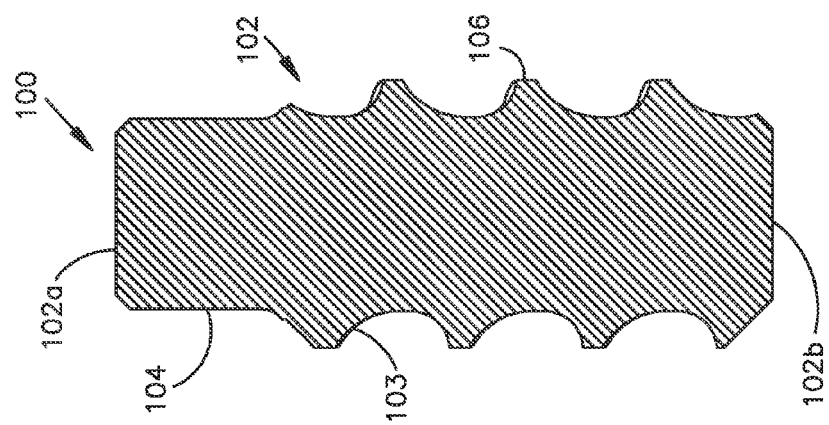
FIG. 2C is a side section view of the implant illustrated in FIG. 1.
Figure 2B:
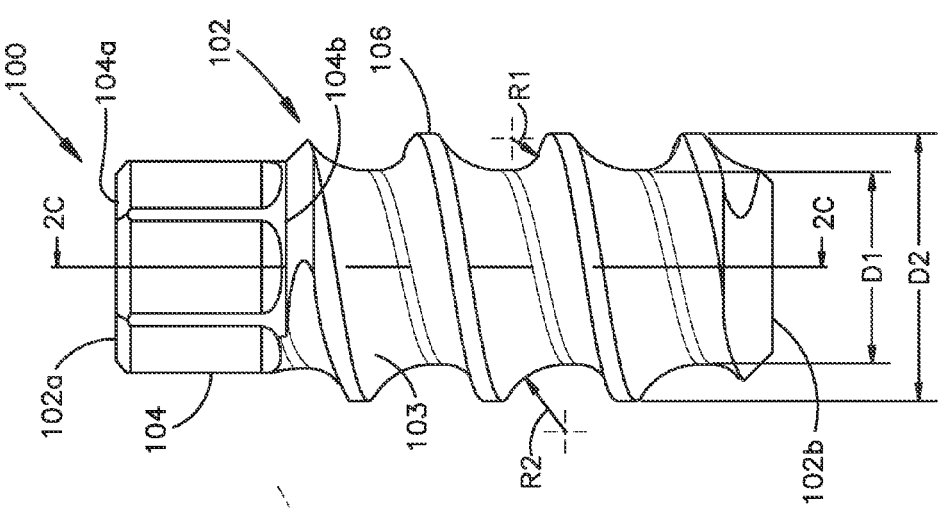
FIG. 2B is a side elevation view of the implant illustrated in FIG. 1.
Figure 2A:
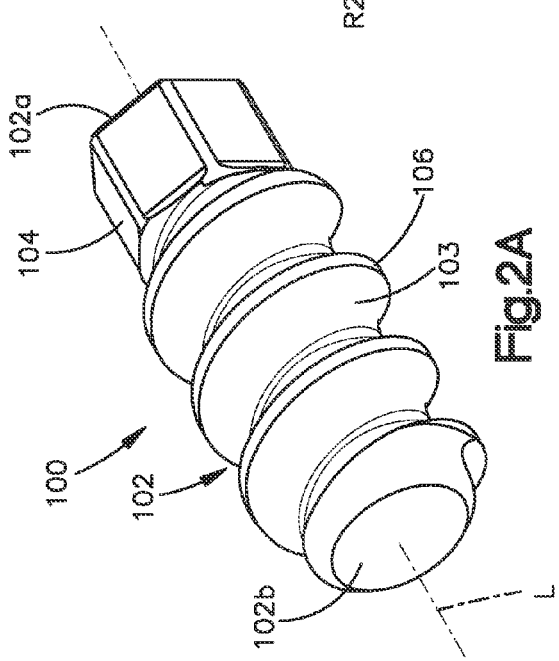
FIG. 2A is a perspective view of the implant illustrated in FIG. 1.

Referring now to FIGS. 2A-C, the facet fusion implant 100 includes an implant body 102 having a proximal end 102a and an opposed distal end 102b. The body 102 of the implant 100 is sized to be received in a facet joint, and in particular in the gap between the inferior and superior facet articulation surfaces of a pair of adjacent vertebrae. In accordance with the illustrated embodiment, the implant body 102 is elongate between the proximal and distal ends 102a, 102b, respectively, along a longitudinal, or central axis L, and has a substantially cylindrical shape. That is, the body 102 has a substantially circular cross section in a plane substantially perpendicular to the central axis L. However, it should be appreciated that the implant 100 is not limited to the illustrated cylindrically shaped body 102, and that the body 102 of the implant 100 can alternatively be constructed with any other geometry as desired.

The body 102 of the illustrated implant 100 includes head portion 104 disposed at the proximal end 102a and a shaft portion 103 that extends distally from the head portion 104 toward the distal end 102b. The head portion 104 defines a proximal head portion end 104a and a distal head portion end 104b opposite the proximal head portion end 104a. The head portion 104 can be integral with the body 102 or can be affixed thereto.

The head portion 104 of the body 102 can define, or carry an instrument engaging element configured to releasably engage with a complimentary engaging element of an insertion instrument, such that a rotational force applied to the insertion instrument is transmitted to the engaging element of the head portion 104 and thus to the shaft portion 103, thereby causing the implant 100 to be advanced into or backed out of a facet joint. In accordance with the illustrated embodiment, the engaging element can be constructed as a plurality of flats defining a "hex" style head portion 104. That is, the head portion 104 can have a substantially hex-shaped cross section in a plane that is substantially perpendicular to the central axis L. It should be appreciated that the facet fusion implant 100 is not limited to the illustrated hex style engaging element. For example, the head portion 104 can be alternatively constructed with any other internal and/or external engaging element as desired. Alternatively, the head portion 104 of the implant 100 can be minimized such that the engaging element is substantially defined by the shaft portion 103 of the implant body 102. For instance the engaging element could be defined as an internal drive feature extending into the shaft portion 103 of the implant body 102 at the proximal end 102a thereof.

The head portion 104 can be constructed such that it defines a cross-sectional dimension that does not exceed a cross-sectional dimension of the shaft portion 103, the cross-sectional dimensions measured in respective planes that are substantially perpendicular to the central axis L. For example, in accordance with the illustrated embodiment the head portion 104 is constructed such that its cross-sectional dimension does not exceed the major diameter D2 of threads 106 defined by the shaft portion 103, regardless of where the cross-sectional dimension of the head portion 104 is measured. In other words, the head portion 104 does not define a cross-sectional dimension that exceeds the outermost cross-sectional dimension of the shaft portion 103, as defined by the major diameter D2 of the threads 106. Constructing the head portion 104 such that its cross-sectional dimension does not exceed the major diameter D2 of the threads 106 of the shaft portion 103 can be advantageous to a surgeon inserting the implant 100. For example, because the cross-sectional dimension of the head portion 104 of the illustrated implant 100, and thus the corresponding engaging element, do not exceed the major diameter D2 of the threads 106 of the shaft portion 103, the head portion 104 does not interfere with the depth to which the implant 100 can be rotationally driven into the facet joint FJ. Additionally, constructing the head portion 104 such that it does not define a cross-sectional dimension that exceeds that of the shaft portion 103 allows the cross-sectional dimension of the cannulation 904 of the guide tube 900 (see FIGS. 13A-14F) through which the implant 100 is delivered the to the facet joint FJ, and thus the overall cross-sectional footprint of the guide tube 900 itself, to be minimized.

The body 102 of the implant can be constructed so as to minimize and/or prevent migration of the implant 100 within the facet joint, thereby keeping the implant 100 properly positioned within the facet joint FJ. For example, in accordance with the illustrated embodiment, the shaft portion 103 of the body 102 can define a plurality of helical threads 106 extending radially outward from the shaft portion 103, the threads 106 configured to engage with the articulation surfaces of the facet joint FJ when the implant 100 is driven into the facet joint FJ. The threads 106 can be defined along a portion of the length of the body 102, for example along the shaft portion 103. In accordance with the illustrated embodiment, the threads 106 originate from the distal end 102b of the body 102, extending in a helical path around the circumference of the shaft portion 103 of the body 102 in a direction toward the proximal end 102a of the body 102, the threads 106 terminating at the distal head portion end 104b of the head portion 104. It should be appreciated that the threads 106 are not limited to the illustrated originating and terminating locations, and that the threads 106 can alternatively be constructed with any other originating and terminating locations along the body 102 as desired.

The threads 106 of the illustrated implant 100 are constructed as asymmetric threads, and in particular buttress style threads. That is, the opposed faces of the threads are not symmetrical with respect to a plane that is substantially perpendicular to the longitudinal axis L. In particular, the thread faces facing the proximal end 102a of the body 102 are constructed using a radius of curvature R1, while the thread faces facing the distal end 102b of the body are constructed using a radius of curvature R2 that is longer than that of R1. Thus, the thread faces facing the proximal end 102a of the body 102 form a steeper angle with respect to a plane that is substantially perpendicular to the longitudinal axis L than that of the thread faces facing the distal end 102b of the body 102.

The threads 106 can be constructed with a major diameter D2 that defines the peaks of the threads 106 and a minor diameter D1 that defines the valleys of the threads 106. In accordance with the illustrated embodiment, the major diameter D2 is longer than the minor diameter D1, and the minor diameter D1 is sized to be longer than the gap between the opposed articulation surfaces of a facet joint into which the implant is to be inserted, for example the gap between the inferior and superior articulation surfaces IS, SS of the facet joint FJ depicted in FIG. 1. For example, in accordance with the illustrated embodiment, the implant 100 can be constructed with a major diameter D2 in the range of about 5.0 mm to 7.0 mm, and a corresponding minor diameter D1 in the range of about 3.5 mm to about 5.5 mm. Preferably, the implant 100 can be constructed in a first implant size having a major diameter D2 of about 5.5 mm and a minor diameter D1 of about 4.0 mm, and/or in a second implant size having a major diameter D2 of about 6.5 mm and a minor diameter D1 of about 5.0 mm. However, it should be appreciated that the implant 100 is not limited to the major and minor diameters D2, D1 illustrated and/or described herein, and that the geometry of the threads 106 of the implant 100 can be alternatively constructed as desired. The major and minor diameters D2, D1 of the threads 106 of the illustrated implant 100 define constant lengths, respectively, between the distal end 102b of the body 102 and the distal head portion end 104b of the head portion 104, but it should be appreciated that the threads 106 can be alternatively constructed such that the major diameter D2 and/or the minor diameter D1 vary in length between the distal end 102b of the body 102 and the distal head portion end 104b of the head portion 104, for instance to define tapered threads.

Referring now to FIGS. 3A-C, a facet fusion implant 200 constructed in accordance with an alternative embodiment is illustrated. The implant 200 can be constructed similarly to the implant 100, but with the body 102 defining a cannulation 108 that extends through the body 102 along the longitudinal axis L. The diameter of the cannulation 108 can be sized to fit over a guide pin during insertion of the implant 200 into a facet joint, as described in more detail below. The implant 200 is preferably constructed of a biocompatible, implantable metal, for instance titanium, titanium alloy such as TAN, stainless steel, or the like. Although the illustrated implant 200 is constructed for use with the drilling and tapping steps of the below-described surgical procedure, it should be appreciated that the implant 200 can alternatively be constructed as a self-drilling and/or self-tapping facet fusion implant 200. It should further be appreciated that the implant 200 is not limited to being constructed of metal, and that the implant 200 can alternatively be constructed using any other biocompatible, implantable material as desired, including polymers such as polyetheretherketone (PEEK), reinforced plastics, allograft bone, autograft bone, and the like.

Referring now to FIGS. 4A-E, a facet fusion implant 300 constructed in accordance with still another alternative embodiment is illustrated. The implant 300 can be constructed similarly to the implant 200, but with the body 102 further defining at least one, such as a plurality of apertures 110 that extend into the body 102 and are open to the cannulation 108. In accordance with the illustrated embodiment, the body 102 defines a plurality of apertures 110 that extend radially into the body along respective axes that are substantially perpendicular to the longitudinal axis L. The apertures 110 can be defined in a spaced helical pattern that follows the valley of the threads 106. In use, the apertures 110 can be packed with a bone growth inducing substance, for instance a bone morphogenic protein (BMP), so as to enhance the fusion process across the facet joint into which the implant 300 is inserted. For example, the bone growth inducing substance can promote bony ingrowth from one or both of the respective articulation surfaces of the facet joint into the apertures 110, thereby enhancing characteristics of the fused facet joint, for example by lending additional strength to the fused facet joint. It should be appreciated that the implant 300 is not limited to the illustrated apertures 110, and that the body 102 of the implant 300 can alternatively be constructed with any other number and/or pattern of apertures, the apertures having the same or different geometries, as desired.

Referring now to FIGS. 5A-B, a facet fusion implant 400 constructed in accordance with still another alternative embodiment is illustrated. The implant 400 can be constructed similarly to the implant 100, but with a differently constructed head portion 104 and engaging element. For example, in accordance with the illustrated embodiment, the head portion 104 of the body 102 is constructed with an engaging element that includes a pair of tapered projections 112 disposed at the proximal end 102a of the body 102. The projections 112 can be spaced apart from each other, defining a slot 114, the slot 114 configured to receive a complimentary engaging element of an insertion instrument, such that a rotational force applied to the insertion instrument is transmitted to the head portion 104, and thus to the shaft portion 103 of implant body 102, thereby causing the implant 400 to be rotationally advanced into or backed out of a facet joint. Additionally, the threads 106 defined by the implant 400 are symmetric threads, in contrast to the asymmetric threads of the implant 100. It should be appreciated that one or more of the features that differentiate the implant 400 from the implant 100, can be implemented in the construction of any of the above-described implants 100, 200, or 300.

Referring generally to FIGS. 6-20, an example surgical method for inserting a facet fusion implant, such as the above-described implants 100-400, is illustrated. For the sake of simplicity, the surgical method is illustrated and described herein with reference to the insertion of a single one of the above-described facet fusion implant 100, but it should be appreciated that any number of the implants 100-400 can be similarly inserted utilizing the surgical method described herein. The surgical method can be performed as an open procedure, a minimally invasive procedure, for instance using tubular retractors or percutaneous techniques and/or instrumentation, or any combination thereof. It should be appreciated that the implants 100-400 and the method of surgically inserting the implants 100-400 are not limited to the lumbar region of the spine as illustrated, and that the facet fusion implants 100-400 and associated surgical insertion method and instrumentation can be utilized to insert the implants 100-400 into any other suitable region of the spine as desired.

At the outset of the minimally invasive facet fusion implant insertion procedure, a degenerated or otherwise unhealthy facet joint, such as the facet joint FJ defined by the first and second vertebrae V1, V2 is identified within the patient. The facet joint FJ can be identified by fluoroscopy, x-ray imaging, magnetic resonance imaging (MRI), or the like. Once the affected facet joint FJ is identified and located within the patient, a small incision is made to permit the insertion of implant insertion instrumentation into the facet joint FJ.

Referring now to FIGS. 6-7B, a guide pin 500 can be placed through the incision and inserted into position within the facet joint FJ. The guide pin 500 can be impacted into place in the facet joint FJ, for example between the inferior and superior articulation surface IS, SS, respectively, of the first and second vertebrae V1, V2. In its inserted position, the guide pin 500 can define an insertion trajectory to the surgical site along which the implant 100 and implant insertion instruments used in subsequent steps of the surgical insertion method can be delivered to the facet joint FJ, as described in more detail below. Preferably, the guide pin 500 is inserted into substantially the center of the facet joint FJ, as depicted in FIG. 6. The guide pin 500, and the other implant insertion instruments described below for use in the facet fusion implant surgical insertion method are preferably constructed of biocompatible metals such as titanium, titanium alloy such as TAN, and/or stainless steel. Of course the individual insertion instruments can be made of the same or different metals, in any combination. Furthermore, it should be appreciated that the implant insertion instruments are not limited to construction with metal, and can alternatively be constructed of any other suitable biocompatible material as desired.

In accordance with the illustrated embodiment, the guide pin 500 includes a substantially cylindrically shaped pin body 502 defining a proximal end 502a and an opposed distal end 502b. The distal end 502b of the pin body 502 can be constructed with a tapered and/or narrowed cross section, defining a blade-like tip 504 with opposed upper and lower surfaces 504a, 504b, the tip 504 configured to be inserted into the gap between the inferior and superior articulation surface IS, SS, respectively, of the facet joint FJ. The tip 504 can aid the surgeon in identifying characteristics of the facet joint FJ. For instance, the upper and lower surfaces 504a, 504b of the tip can be disposed between the inferior and superior articulation surfaces IS, SS, respectively, of the facet joint, thereby locating a plane of the facet joint FJ. It should be appreciated that the guide pin 500 is not limited to the geometry of the illustrated tip 504, and that the tip 504 can be alternatively constructed with any other geometry as desired. For example, in an alternative embodiment the distal end of the pin body can define at least one, such as a plurality of flats that are tapered from a point proximal of the distal end, and converge at the distal end to form a sharp point, or trocar-like tip.

The pin body 502 can be sized to match one or more characteristic dimensions of the implant 100 in order to facilitate selecting an appropriately sized implant 100. For example, the pin body 502 can be constructed with a cross-sectional dimension, in a plane substantially perpendicular to the central axis L, that is substantially equal to the minor diameter D1 of a selected implant 100. If upon insertion of the guide pin 500 into the face joint FJ, the pin body 502 enters the facet joint beyond the tip 504, it may indicate that an implant 100 with a larger minor diameter D1 may be required in order to provide a desired degree of fixation within the facet joint FJ. The proximal end 502a of the pin body 502 can define at least one, such as a plurality of gripping elements 506, the gripping elements 506 configured to facilitate gripping and maneuvering the guide pin 500 as it is inserted into the facet joint FJ.

Figure 8:
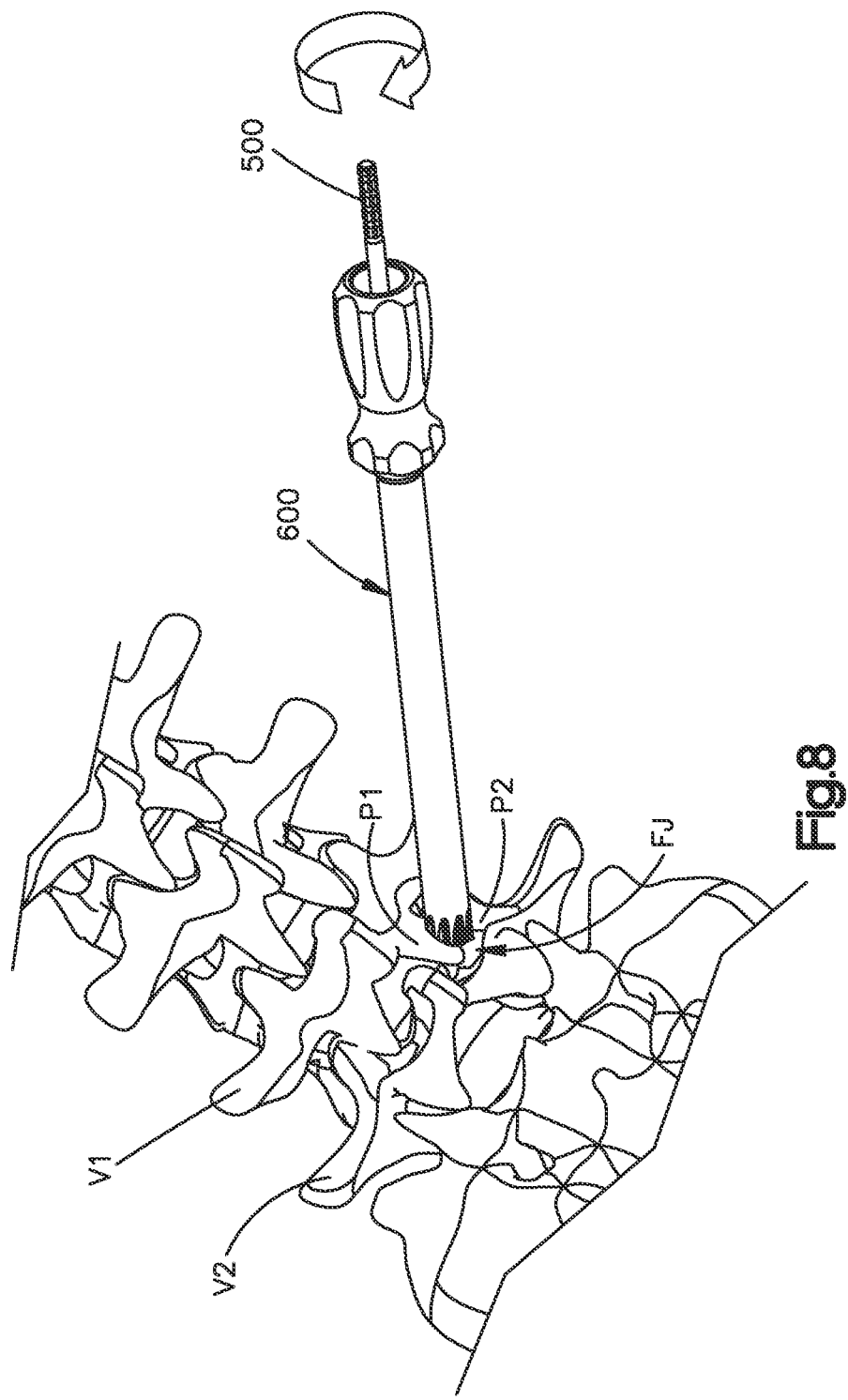
FIG. 8 is a perspective view of a reamer inserted over the guide pin illustrated in FIG. 6.

Referring now to FIGS. 8-9E, with the guide pin 500 inserted into the facet joint FJ, a first step in preparing the facet joint for insertion of the implant 100, in particular reaming the bony surfaces adjacent to the facet joint FJ, can be carried out. The steps of preparing the facet joint FJ for insertion of the implant 100 can further include drilling a bore B (see FIGS. 15A-17C) into the facet joint FJ and/or tapping threads into the bore B, as described in more detail below. The bore B can operate as an insertion path between the bony surfaces of the inferior and superior articulation surface IS, SS, of the first and second vertebrae V1, V2, along which the implant 100 can be driven into the facet joint FJ. In accordance with the illustrated embodiment, a cannulated reamer 600 can be fitted over the guide pin 500 and slidably advanced along the guide pin 500 to the facet joint FJ. The reamer 600 can be utilized to prepare the articular surfaces adjacent the facet joint FJ for insertion of the implant 100. In particular, the reamer 600 can be abutted against the outer surface of the inferior articular process P1 of the first vertebra V1 and/or the outer surface of the superior articular process P2 of the second vertebra V2. The reamer 600 can then be operated by biasing the reamer into the articular processes P1, P2 while a rotational force is applied to the reamer 600.

In operation, the reamer grinds along the surfaces of the articular processes P1, P2, removing osteophytes and wearing away the facet synovial-fluid-filled capsule surrounding the facet joint FJ. The use of the reamer 600 to wear away the synovial capsule and remove osteophytes from the articular processes P1, P2 can aid the surgeon in establishing the true orientation of the facet joint FJ, can create "bleeding bone" surfaces on the articular processes P1, P2 so as to enhance fusion potential between the articular processes P1, P2 and the implant 100 across the facet joint FJ, and can create a uniform surface at the facet joint FJ into which subsequently utilized implant insertion instruments can be seated, as described in more detail below. The proximal end 502a of the guide pin 500 can be stabilized during operation of the reamer 600, for example by the gripping elements 506, in order to promote uniform preparation of the surfaces of the articular processes P1, P2.

In accordance with the illustrated embodiment, the reamer 600 includes a substantially cylindrically shaped reamer body 602 defining a proximal end 602a and an opposed distal end 602b. The reamer body 602 defines a cannulation 604 therethrough along the longitudinal axis L, the diameter of the cannulation 604 sized such that the guide pin 500 is slidably received in the cannulation 604 when the reamer 600 is inserted over the guide pin 500. The distal end 602b of the reamer body 602 defines a reaming head 606 having at least one, such as a plurality of reaming members defined thereon. The reaming head 606 of the illustrated embodiment has a plurality of longitudinal slots 608 defined therein, the slots 608 defining a corresponding plurality of reaming members in the form of blades 610. The blades 610 are configured to cut into the bony surfaces of the articular processes of the facet joint FJ when the reamer 600 is inserted over the guide pin 500 such that the reaming head 606 comes into contact with the articular processes P1, P2 and operated by rotating the reamer 600 about the guide pin 500. It should be appreciated that the reaming members of the reamer 600 are not limited to the illustrated blades 610, and that the reaming head 606 of the reamer 600 can be alternatively constructed with any other suitable reaming member geometry as desired. The proximal end 602a of the reamer body 602 defines a handle 612, the handle configured for gripping by a surgeon during insertion, operation, and/or removal of the reamer 600. The handle 612 can be integrally formed with the body 602 or constructed separately and affixed thereto. It should be appreciated that handles can similarly be integrally formed or affixed to any of the remainder of the surgical instruments described below that are suitable for use with a handle, as desired.

Referring now to FIGS. 10-11D, once the surfaces of the articular processes P1, P2 have been prepared utilizing the reamer 600, the reamer 600 can be removed from the guide pin 500 and a joint finder 700 can be inserted over the guide pin 500 and slidably advanced to the facet joint FJ. Alternatively, if the step of preparing the articular processes P1, P2 with the reamer 600 was omitted, the joint finder 700 can be inserted over the guide pin 500 and slidably advanced to the facet joint FJ. The joint finder 700 can be utilized to further aid the surgeon in identifying characteristics of the facet joint FJ, for instance by locating a plane of the facet joint FJ as defined between the inferior and superior articulation surfaces IS, SS, respectively.

In accordance with the illustrated embodiment, the joint finder 700 includes a substantially cylindrically shaped finder body 702 defining a proximal end 702a and an opposed distal end 702b. The finder body 702 defines a cannulation 704 therethrough along the longitudinal axis L, the diameter of the cannulation 704 sized such that the guide pin 500 is slidably received in the cannulation 704 when the joint finder 700 is inserted over the guide pin 500. The distal end 702b of the finder body 702 can be constructed for insertion into the plane of the facet joint FJ. For instance, the distal end 702b of the finder body 702 of the illustrated joint finder 700 can include a pair of legs 706 that extend from the distal end 702b along a direction that is substantially parallel to the longitudinal axis L.

The legs 706 can be located on opposed sides of the distal end 702b of the finder body 702, and can have a height H that is substantially equal to the width of the gap defined between the inferior and superior articulation surfaces IS, SS of the facet joint FJ. The upper and lower surfaces of the legs 706 can be tapered at the distal ends thereof to form tips 708, the tips 708 configured to ease insertion of the legs 706 into the gap in the facet joint FJ. The finder body 702 can be sized to match one or more characteristic dimensions of the implant 100 in order to facilitate selecting an appropriately sized implant 100. For example, the finder body 702 can be constructed with an outer cross-sectional dimension, in a plane substantially perpendicular to the central axis L, that is substantially equal to the major diameter D2 of a selected implant 100. If upon insertion of the joint finder 700 into the face joint FJ, an excessive amount of the bony surfaces of the first and second vertebrae V1, V2 on one or both sides of the facet joint FJ is obscured by the finder body 702, it may indicate that an implant 100 with a smaller major diameter D2 may be required in order to provide a desired degree of fixation within the facet joint FJ.

The proximal end 702a of the finder body 702 can define at least one, such as a plurality of gripping elements, the gripping elements configured to facilitate the gripping and maneuvering of the joint finder 700 as it is inserted over the guide pin 500 and into the facet joint FJ. For example, the proximal end 702a of the finder body 702 of the illustrated joint finder 700 defines a plurality of annular gripping grooves 710 spaced inwardly from the proximal end 702a of the finder body 702. It should be appreciated that the joint finder 700 is not limited to the gripping elements of the illustrated grooves 710, and that the finder body 702 can be alternatively constructed with any other type of suitable gripping elements as desired. The proximal end 702a of the finder body 702 can further define first and second pluralities of longitudinal grooves 712 on opposed sides of the finder body 702, each of the pluralities of grooves 712 aligned with a respective one of the legs 706. Because the grooves 712 are aligned with the legs 706, the grooves 712 can facilitate identification of the plane of the facet joint FJ by the surgeon after the joint finder 700 is inserted into the facet join FJ.

In operation, the joint finder 700 can be inserted over the guide pin 500 and slidably advanced to the facet joint FJ. As the legs 706 approach the facet joint FJ, the joint finder 700 can be rotated about the guide pin 500 until the legs 706 are aligned with the plane of the facet joint FJ (i.e., aligned with the gap between the inferior and superior articulation surfaces IS, SS). With the legs 706 properly aligned, the joint finder 700 can be inserted into the facet joint FJ until the joint finder 700 is seated on the surfaces of the articular processes P1, P2. If necessary, the joint finder 700 can be advanced into the facet joint FJ with the use of an impaction cap 800 designed to be inserted over the joint finder and to transmit one or more impaction forces applied to the impaction cap 800 to the joint finder 700 without disturbing the guide pin 500.

Referring now to FIGS. 12A-D, in accordance with the illustrated embodiment, the impaction cap 800 includes a substantially cylindrically shaped cap body 802 defining a proximal end 802a, an opposed distal end 802b, and an outer circumferential surface defined about a longitudinal axis L extending between the proximal and distal ends 802a, 802b. The outer surface 802c can define at least one, such as a plurality of gripping elements, the gripping elements configured to enhance a surgeon's ability to grip the impaction cap 800. For example, the outer surface 802c of the illustrated impaction cap 800 defines a plurality of annular gripping grooves 804 spaced along the length of the cap body 802 between the proximal and distal ends 802a, 802b. Additionally, the cap body 802 of the illustrated impaction cap 800 defines a pair of flat sides 806 on opposed sides of the cap body 802, the flat sides 806 extending along the entirety of the length of the cap body 802 between the proximal and distal ends 802a, 802b. It should be appreciated that the impaction cap 800 is not limited to the gripping elements of the illustrated grooves 804 and flat side 806, and that the cap body 802 can be alternatively constructed with any other type of suitable gripping elements as desired.

The cap body 802 has a plurality of bores of varying diameters formed therethrough about the longitudinal axis L, such that the cap body 802 is cannulated. A first bore 808 extend into the cap body 802 from the proximal end 802a and opens to a second bore 810 at an intermediate location between the proximal and distal ends 802a, 802b. The second bore 810 extends from the intermediate location towards the distal end 802b of the cap body 802, where it opens to a third bore 812 that extends into the cap body 802 from the distal end 802b.

The first bore 808 has a diameter that is sized to be substantially equal to, but slightly larger than the outside diameter of the guide pin 500, such that the impaction cap 800 can be slidably inserted over the guide pin 500. A first tapered edge 814 is defined where the diameter of the first bore 808 opens to the second bore 810. The second bore 810 has a diameter that is larger than the diameter of the first bore 808 and sized to be substantially equal to, but slightly larger than the outside diameter of the joint finder 700, such that the impaction cap 800 can be slidably inserted over the guide pin 500 and the joint finder 700. A second tapered edge 816 is defined where the second bore 810 opens to the third bore 812. The third bore 812 has a diameter that is larger than the diameters of the first bore 808 and the second bore 810 and sized to be substantially equal to, but slightly larger than the outside diameter of a guide tube 900 (see FIGS. 14A-F), such that the impaction cap 800 can be slidably inserted over the guide pin 500, the joint finder 700, and the guide tube 900, as described in more detail below.

In operation, to transmit impaction forces to the joint finder 700, the proximal end 802a of the body 802 of the impaction cap 800 is inserted over the guide pin 500 until the proximal end 802a abuts the proximal end 702a of the body 702 of the joint finder 700. With the proximal end 802a of the impaction cap 800 abutting the proximal end 702a of the joint finder 700, the distal end 802b of the impaction cap 800 will extend beyond the proximal end 502a of the guide pin 500 so that the guide pin 500 is recessed within the joint finder 700 and the impaction cap 800, such that the guide pin 500 will not be further advanced within the facet joint FJ when impaction forces are applied to the distal end 802b of the impaction cap 800. One or more impaction forces can be applied to the distal end 802b of the body 802 of the impaction cap 800. A surgeon can apply the impaction forces to the impaction cap 800 by utilizing a mallet, the surgeon's hand, a mechanical impaction device, or the like, or any combination thereof, as desired. When the joint finder 700 is fully inserted, or seated in the facet joint FJ, the impaction cap 800 can be removed from the guide pin 500.

Figure 13B:
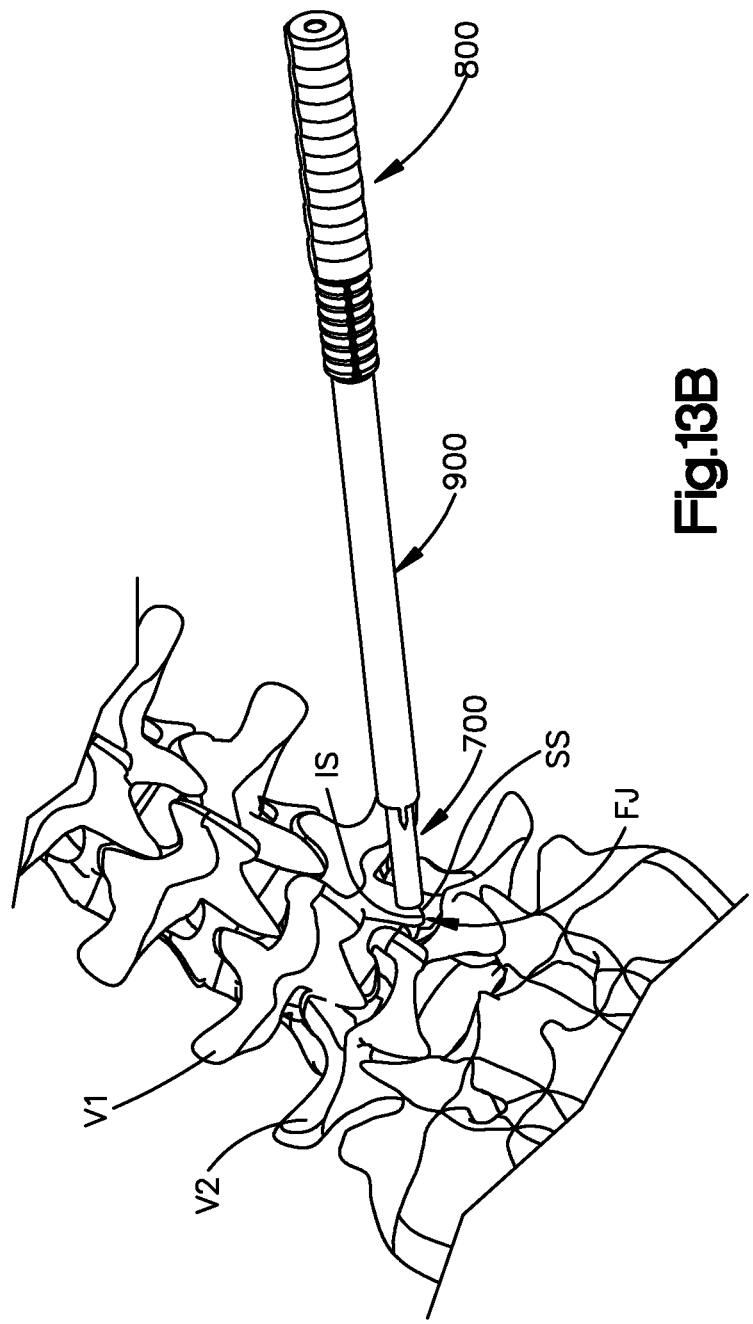
FIG. 13 is a perspective view of a guide tube inserted over the joint finder illustrated in FIG. 11A.
Figure 15A:
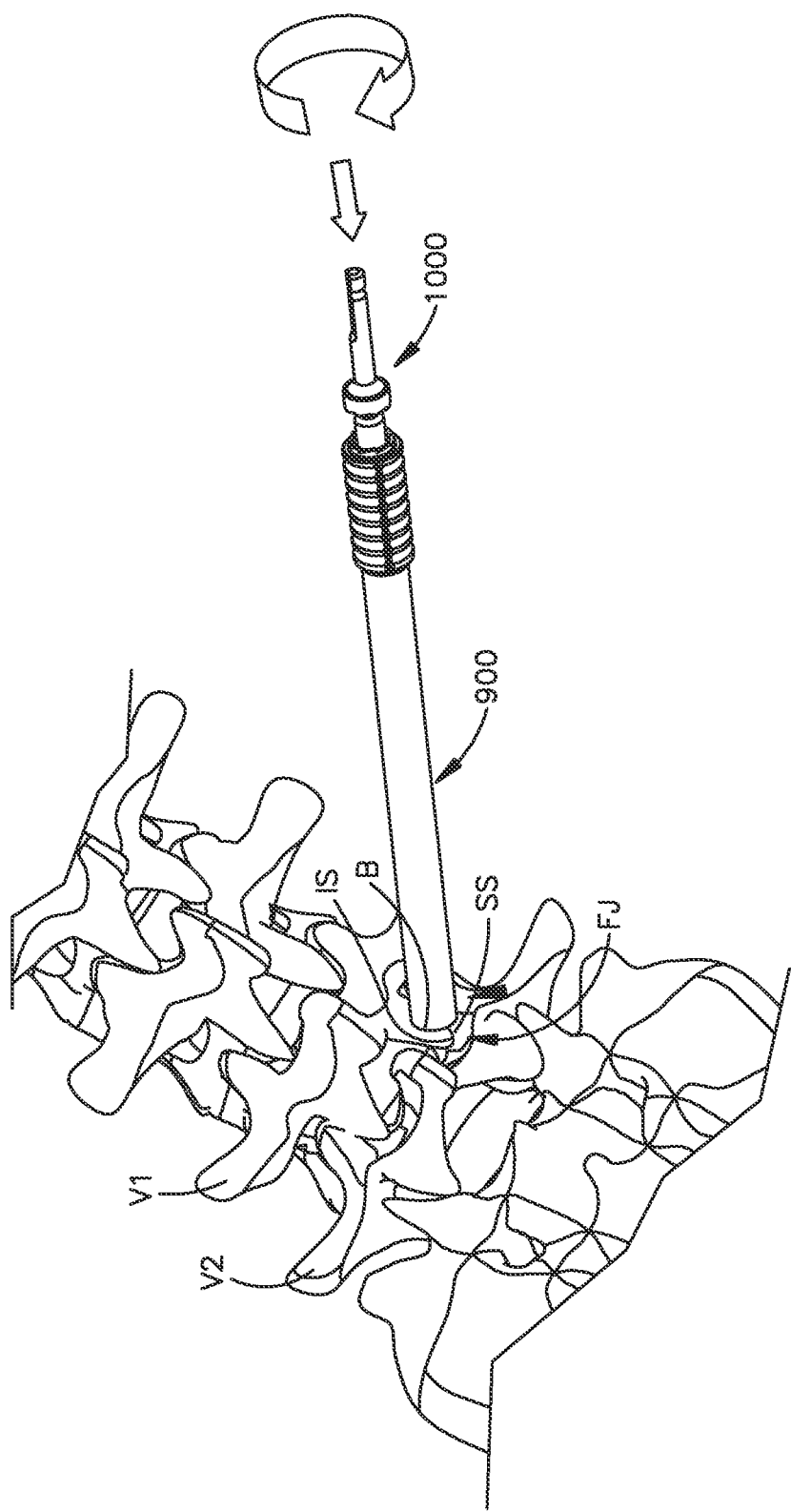
FIG. 15A is a perspective view of a drill bit inserted through the guide tube illustrated in FIG. 14A and into the facet joint.

Referring now to FIGS. 13-14F, once the joint finder 700 is inserted into the facet joint FJ and seated against the surfaces of the articular processes P1, P2, a guide tube 900 can be inserted over the joint finder 700 and guide pin 500 and slidably advanced to the facet joint FJ. When inserted into the facet joint FJ, the guide tube 900 can be utilized as a portal through which facet joint preparation and/or implant insertion instruments can be inserted in order to bore and tap the facet joint FJ, and/or to insert the implant 100 into the facet joint FJ, as described in more detail below.

In accordance with the illustrated embodiment, the guide tube 900 includes a substantially cylindrically shaped tube body 902 defining a proximal end 902a and an opposed distal end 902b. The tube body 902 defines a cannulation 904 therethrough along the longitudinal axis L, the diameter of the cannulation 904 sized such that the joint finder 700 is slidably received in the cannulation 904 when the guide tube 900 is inserted over the joint finder 700. The distal end 902b of the tube body 902 can be constructed for insertion into the plane of the facet joint FJ. For instance, the distal end 902b of the tube body 902 of the illustrated guide tube 900 can include a pair of legs 906 that extend from the distal end 902b along a direction that is substantially parallel to the longitudinal axis L. The legs 906 can be located on opposed sides of the distal end 902b of the tube body 902, and can have a height H that is substantially equal to that of the height H of the legs 706 of the joint finder 700. The upper and lower surfaces of the legs 906 can be tapered at the distal ends thereof to form tips 908, the tips 908 configured to ease insertion of the legs 906 into the gap in the facet joint FJ.

The distal end 902b of the tube body 902 can further include at least one, such as a plurality of anchoring elements configured to anchor the guide tube 900 to the surfaces of the articular processes P1, P2. For example, the distal end 902b of the illustrated guide tube 900 defines a plurality of anchoring elements in the form of teeth 910 along the peripheral edges of the distal end 902b of the tube body 902 between the legs 906, the teeth 910 configured to cut into the bony surfaces of the articular processes P1, P2. In accordance with the illustrated embodiment, two teeth 910a of a first size extend distally from each of the upper and lower arc shaped portions of the distal end 902b of the tube body 902 between the legs 906, each large tooth 910a flanked by a tooth 910b of a second size that is smaller that of the teeth 910a, the teeth 910b disposed between the teeth 910a and the respective legs 906. Of course the tube body 902 can alternatively define more or fewer teeth 910, sized the same or differently and/or oriented the same or differently as the illustrated teeth 910, as desired. When the legs 906 of the guide tube 900 are inserted into the gap in the facet joint FJ and the guide tube 900 is advanced into a seated position, the teeth 910 cut into the surfaces of the articular processes P1, P2, thereby lending additional stability to the guide tube 900 when it is in a fully inserted and seated position in the facet joint FJ. It should be appreciated that the anchoring elements of the guide tube 900 are not limited to the illustrated teeth 910, and that the tube body 902 can be alternatively constructed using any other suitable anchoring elements as desired.

The proximal end 902a of the tube body 902 can define at least one, such as a plurality of gripping elements, the gripping elements configured to facilitate the gripping and maneuvering of the guide tube 900 as it is inserted over the joint finder 700 and into the facet joint FJ. For example, the proximal end 902a of the tube body 902 of the illustrated guide tube 900 defines a plurality of annular gripping grooves 912 spaced inwardly from the proximal end 902a of the tube body 902. It should be appreciated that the guide tube 900 is not limited to the gripping elements of the illustrated grooves 912, and that the tube body 902 can be alternatively constructed with any other type of suitable gripping elements as desired. The proximal end 902a of the tube body 902 can further define first and second pluralities of longitudinal grooves 914 on opposed sides of the tube body 902, each of the pluralities of grooves 914 aligned with a respective one of the legs 906. Because the grooves 914 are aligned with the legs 906, the grooves 914 can facilitate identification of the plane of the facet joint FJ by the surgeon after the guide tube 900 is inserted into the facet join FJ.

The proximal end 902a of the tube body 902 can further define at least one, such as a plurality of locking elements configured to engage with complementary locking elements of another implant insertion tool, as described in more detail below. The proximal end 902a of the illustrated guide tube 900 defines a plurality of locking teeth 916 spaced annularly along the perimeter of the proximal end 902a of the tube body 902, the locking teeth 916 offset from the outer perimeter of the tube body 902 so as to define an impaction ledge 917 configured to abut with the impaction cap 800, as described below. It should be appreciated that the guide tube 900 is not limited to the locking elements of the illustrated locking teeth 916, and that the tube body 902 can be alternatively constructed with any other type of suitable locking elements as desired.

In operation, the guide tube 900 can be inserted over the joint finder 700 and the guide pin 500 and slidably advanced to the facet joint FJ. As the legs 906 approach the facet joint FJ, the guide tube 900 can be rotated about the joint finder 700 until the grooves 914 on the proximal end 902a of the tube body 902 align with the grooves 712 on the proximal end 702a of the joint finder 700. Aligning the grooves 914 with the grooves 712 in turn aligns the legs 906 of the guide tube 900 with the legs 706 of the joint finder 700, such that the legs 906 of the guide tube 900 are properly aligned with the plane of the facet joint FJ (i.e., aligned with the gap between the inferior and superior articulation surfaces IS, SS). With the legs 906 properly aligned, the guide tube 900 can be inserted into the facet joint FJ until the guide tube 900 is seated on the articular processes P1, P2.

If necessary, the guide tube 900 can be advanced into the facet joint FJ with the use of the impaction cap 800. For instance, in order to transmit impaction forces to the guide tube 900, the distal end 802b of the body 802 of the impaction cap 800 is inserted over the joint finder 700 and the guide pin 500 until the impaction ledge 917 of the tube body 902 abuts the distal end 802b of the body 802 of the impaction cap 800. With the impaction ledge 917 abutting the second tapered edges 816, the proximal end 702a of the joint finder 700 and the proximal end 502a of the guide pin will be recessed within the second bore 810 and the first bore 808 of the impaction cap 800 respectively, such that the joint finder 700 and the guide pin 500 will not be further advanced within the facet joint FJ when impaction forces are applied to the proximal end 802a of the impaction cap 800. One or more impaction forces can be applied to the proximal end 802a of the body 802 of the impaction cap 800. A surgeon can apply the impaction forces to the impaction cap 800 by utilizing a mallet, the surgeon's hand, a mechanical impaction device, or the like, or any combination thereof, as desired. When the guide tube 900 is fully inserted into the facet joint FJ, the impaction cap 800 can be removed from joint finder 700 and the guide pin 500.

With the guide tube 900 fully inserted into the facet joint FJ, the joint finder 700 and the guide pin 500 can be removed from the facet joint FJ and slid out of the guide tube 900, while leaving the guide tube 900 in its inserted position. The cannulation 904 of the guide tube 900 can be used as a surgical access portal for the remaining steps of the implant insertion method, as described in more detail below.

Referring now to FIGS. 15A-17C, the facet joint FJ can be further prepared for insertion of the implant 100. A drill bit 1000 can be used to cut a bore B into the facet joint FJ, the bore B sized to receive the implant 100. A tap 1100 can be used to cut threads into the inner surfaces of the bore B, the threads in the bore B configured to receive the threads 106 of the implant 100 when the implant 100 is inserted into the bore B. Tapping the inner surfaces of the bore B can also create "bleeding bone" surfaces on the inferior and superior articulation surfaces IS, SS, respectively, so as to enhance fusion potential between the articulation surfaces IS, SS and the implant 100 across the facet joint FJ.

The drill bit 1000 and the tap 1100 can be constructed to be operable within the cannulation 904 of the guide tube 900. For example, the drill bit 1000 can be inserted into the cannulation 904 of the guide tube 900 and slidably advanced through the cannulation 904 to the facet joint FJ. In accordance with the illustrated embodiment, the drill bit 1000 includes a substantially cylindrically shaped bit body 1002 defining a proximal end 1002a and an opposed distal end 1002b. The bit body 1002 can define a cutting portion 1004 near the distal end 1002b, a shank portion 1008 near the proximal end 1002a, and an intermediate portion 1006 that extends between the cutting and shank portions 1004, 1008, respectively.

The cutting portion 1004 can be configured to drill into the facet joint FJ, so as to cut a bore B into the facet joint FJ between the inferior and superior surfaces IS, SS of the facet joint FJ. The cutting portion 1004 can define a cutting tip 1010 defined at the distal end 1002b of the bit body 1002, and at least one, such as a plurality of helical flutes 1012 extending from the distal end 1002b along the bit body 1002 in a direction toward the proximal end 1002a, the flutes 1012 defining respective opposed cutting edges 1014 along their respective lengths. In accordance with the illustrated embodiment, the cutting portion 1004 can define an outer diameter that is substantially equal to the minor diameter D1 of the implant 100. However, the cutting portion 1004 can be alternatively constructed with an outer diameter that is shorter than the minor diameter D1 of the implant 100, for instance to enhance interference between the implant 100 and the bore B within the facet joint FJ, thereby enhancing fixation between the implant 100 and the facet joint FJ and/or reducing the likelihood that the implant 100 will migrate within the facet joint FJ subsequent to insertion. Of course if a plurality of implants 100 with different major and minor diameters D2, D1 are constructed, a corresponding plurality of drill bits 1000 can be constructed, each drill bit 1000 of the plurality having a cutting portion 1004 with an outer diameter sized to match a respective one of the plurality of implants 100.

The intermediate portion 1006 can define an outer diameter that is sized to be approximately that of the cannulation 904 of the guide tube 900, but slightly narrower such that the drill bit 1000 can be received in, and slidably translatable and rotatable in, the cannulation 904. The bit body 1002 can define a raised annular collar 1016 at the intersection of the proximal end of the intermediate portion 1006 and the distal end of the shank portion 1008, the collar 1016 defining opposed proximal and distal surfaces 1016a, 1016b, respectively. The collar 1016 can be located on the bit body 1002 at a particular distance from the distal end 1002b, such that as the drill bit 1000 is rotatably advanced into the facet joint FJ, the distal surface 1016b of the collar 1016 will abut the locking teeth 916 of the guide tube 900, operating as a depth stop when the cutting portion 1004 has drilled the bore B to a desired depth in the facet joint FJ. It should be appreciated that the drill bit 1000 is not limited to the illustrated location of the collar 1016, and that the collar 1016 can alternatively be located at any other position along the length of the bit body 1002, so as to define the depth of the bore B created by the drill bit 1000 as desired.

The shank portion 1008 of the bit body 1002 can define at least one, such as a plurality of drive engaging elements 1018, the drive engaging elements 1018 configured to engage with complementary drive engaging elements of a driving instrument and/or device configured to apply torque to the drill bit 1000, such as a motorized drill, a handle, or the like.

In use, the drill bit 1000 can be coupled to a driving instrument and/or device before or after the drill bit 1000 is inserted into the guide tube 900 and slidably advanced to the facet joint FJ. The driving instrument can be operated to apply torque to the drill bit 1000 such that the cutting portion 1004 advances into the facet joint FJ, defining the bore B in the facet joint by cutting and removing bone from the inferior and/or superior articulation surfaces IS, SS of the facet joint FJ. The drill bit 1000 can be rotatably advanced into the facet joint FJ until the distal surface 1016b of the collar 1016 abuts the locking teeth 916 of the guide tube 900, at which point the bore B has been cut to the desired depth, and the drill bit 1000 can be removed from the facet joint FJ and the guide tube 900.

Once the bore B has been created by the drill bit 1000, the bore B can be tapped using a tap 1100. Similarly to the drill bit 1000, the tap 1100 can be inserted into the cannulation 904 of the guide tube 900 and slidably advanced through the cannulation 904 to the facet joint FJ. In accordance with the illustrated embodiment, the tap 1100 includes a substantially cylindrically shaped tap body 1102 defining a proximal end 1102a and an opposed distal end 1102b. The tap body 1102 can define a tapping portion 1104 near the distal end 1102b, a shank portion 1108 near the proximal end 1102a, and an intermediate portion 1106 that extends between the tapping and shank portions 1104, 1108, respectively.

The tapping portion 1104 can be configured to cut threads into the inner surface of the bore B, the threads sized to receive the threads 106 of the implant 100 when the implant 100 is inserted into the facet joint FJ and driven into an inserted position. The outer surface of the tapping portion 1104 can define a plurality of helical cutting threads 1110 that extend from the distal end 1102b of the tap body 1102 along a direction toward the proximal end 1102a, the cutting threads 1110 configured to cut threads into the inner surface of the bore B. The tapping portion 1104 can further define at least one, such as a plurality of flutes 1112 extending from the distal end 1102b along the tap body 1102 in a direction toward the proximal end 1102a.

In accordance with the illustrated embodiment, the flutes extend helically along the tapping portion 1104, but alternatively could extend longitudinally along the tap body 1102. The helical flutes 1112 of the illustrated embodiment were found to minimize changes in the spacing of the facet joint FJ during the tapping process, which likely produces a more consistent thread while minimizing potential trauma to the facet joint. The tapping portion 1104 can define an outer diameter that is narrower than that of the intermediate portion 1106, and the threads of the tapping portion 1104 can define major and minor diameters that are substantially equal to the major and minor diameters D2, D1 of the threads 106 of the implant 100. Alternatively, the threads of the tapping portion 1104 can define major and minor diameters that are shorter than the major and minor diameters D2, D1 of the threads 106 of the implant 100, respectively, for instance to enhance interference between the implant 100 and the bore B within the facet joint FJ, thereby enhancing fixation between the implant 100 and the facet joint FJ and/or reducing the likelihood that the implant 100 will migrate within the facet joint FJ subsequent to insertion.

Of course if a plurality of implants 100 with different major and minor diameters D2, D1 are constructed, a corresponding plurality of taps 1100 can be constructed, each tap 1100 of the plurality having a tapping portion 1104 sized to match a respective one of the plurality of implants 100, for instance each tap 1100 of the plurality can be constructed with a tapping portion 1104 having threads that define major and minor diameters that are substantially equal to those of the major and minor diameters D2, D1 of the threads 106 of a respective one of the plurality of implants 100.

The intermediate portion 1106 can define an outer diameter that is sized to be approximately that of the cannulation 904 of the guide tube 900, but slightly narrower such that the tap 1100 can be received in, and slidably translatable and rotatable in, the cannulation 904. The tap body 1102 can define a raised annular collar 1114 at the intersection of the proximal end of the intermediate portion 1106 and the distal end of the shank portion 1108, the collar 1114 defining opposed proximal and distal surfaces 1114a, 1114b, respectively. The distal surface 1114b of the collar 1114 can define at least one, such as a plurality of locking elements configured to engage with the locking elements 916 of the guide tube 900. The distal surface 1114b of the illustrated tap 1100 defines a plurality of locking teeth 1116 spaced around the distal surface 1114b.

The collar 1114 can be located on the tap body 1102 at a particular distance from the distal end 1102b, such that as the tap 1100 is rotatably advanced into the facet joint FJ, the distal surface 1114b of the collar 1114 will abut the proximal end 902a of the guide tube 900, causing the locking teeth 1116 to engage with the locking teeth 916 of the guide tube 900, thereby stopping the tap 1100 from rotating further within the bore B in order to prevent stripping of the threads formed within the bore B by the tap 1100. It should be appreciated that the tap 1100 is not limited to the locking elements of the illustrated locking teeth 1116, and that the tap body 1102 can be alternatively constructed with any other type of suitable locking elements as desired. It should further be appreciated that the tap 1100 is not limited to the illustrated location of the collar 1114, and that the collar 1114 can alternatively be located at any other position along the length of the tap body 1102.

The shank portion 1108 of the tap body 1102 can define at least one, such as a plurality of drive engaging elements 1118, the drive engaging elements 1118 configured to engage with complementary drive engaging elements of a driving instrument and/or device configured to apply torque to the tap 1100, such as a handle, a motorized drill, or the like.

In use, the tap 1100 can be coupled to a driving instrument and/or device, such as a manually operated handle, before or after the tap 1100 is inserted into the guide tube 900 and slidably advanced to the facet joint FJ. The driving instrument can be operated to apply torque to the tap 1100 such that the tapping portion 1104 advances into the facet joint FJ, cutting threads into the inner surface of the bore B by cutting and removing bone from inner surface of the bore B. The tap 1100 can be rotatably advanced into the facet joint FJ until the locking teeth 1116 of the tap 1100 engage the locking teeth 916 of the proximal end 902a of the guide tube 900, at which point the bore B has been tapped to the desired depth, and the tap 1100 can be removed from the facet joint FJ and the guide tube 900 by reversing the direction of rotational force applied to the tap.

Figure 18:
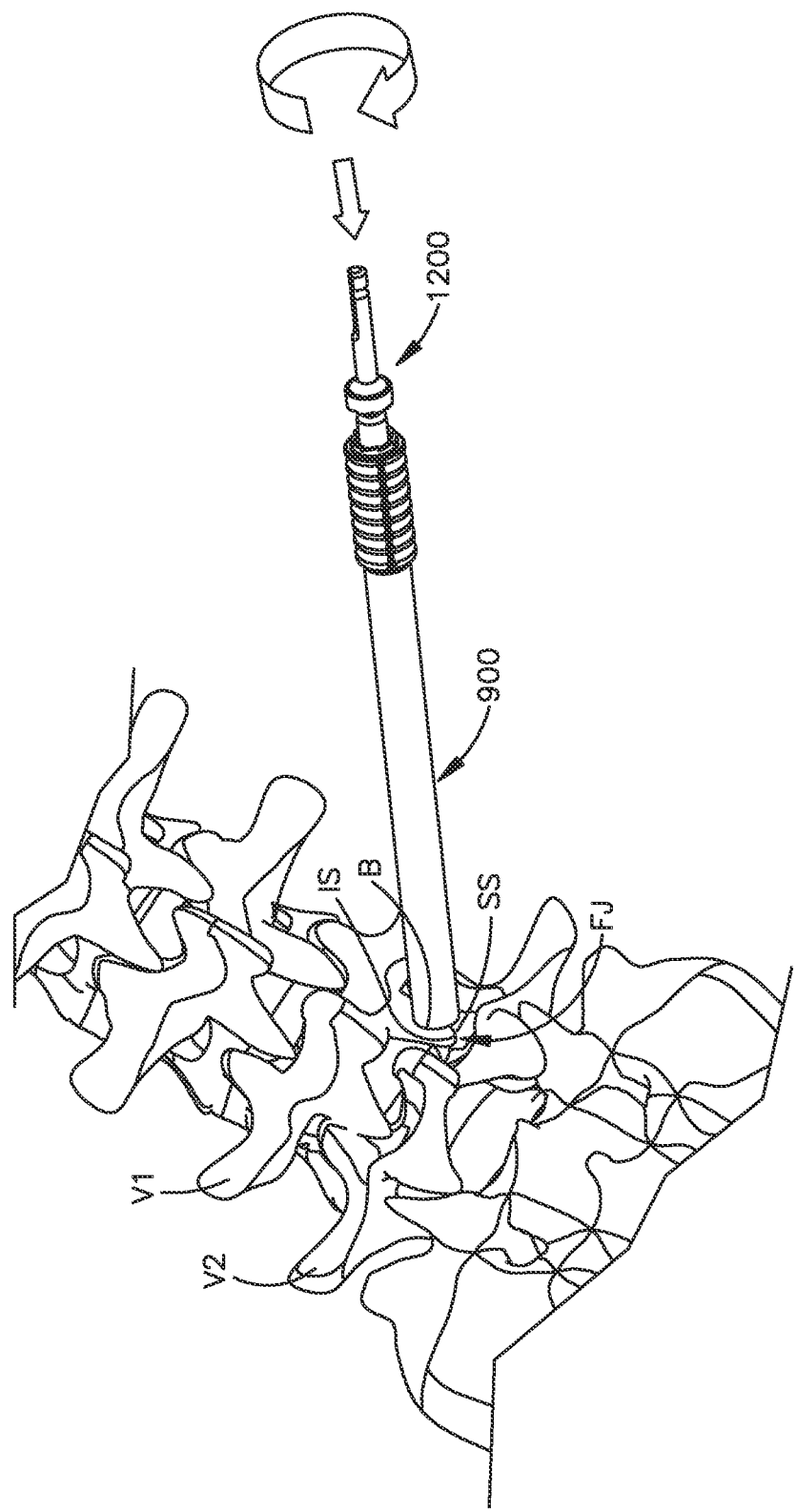
FIG. 18 is a perspective view of a driver shaft carrying a facet fusion implant inserted through the guide tube illustrated in FIG. 14A and into the facet joint.
Figure 20:
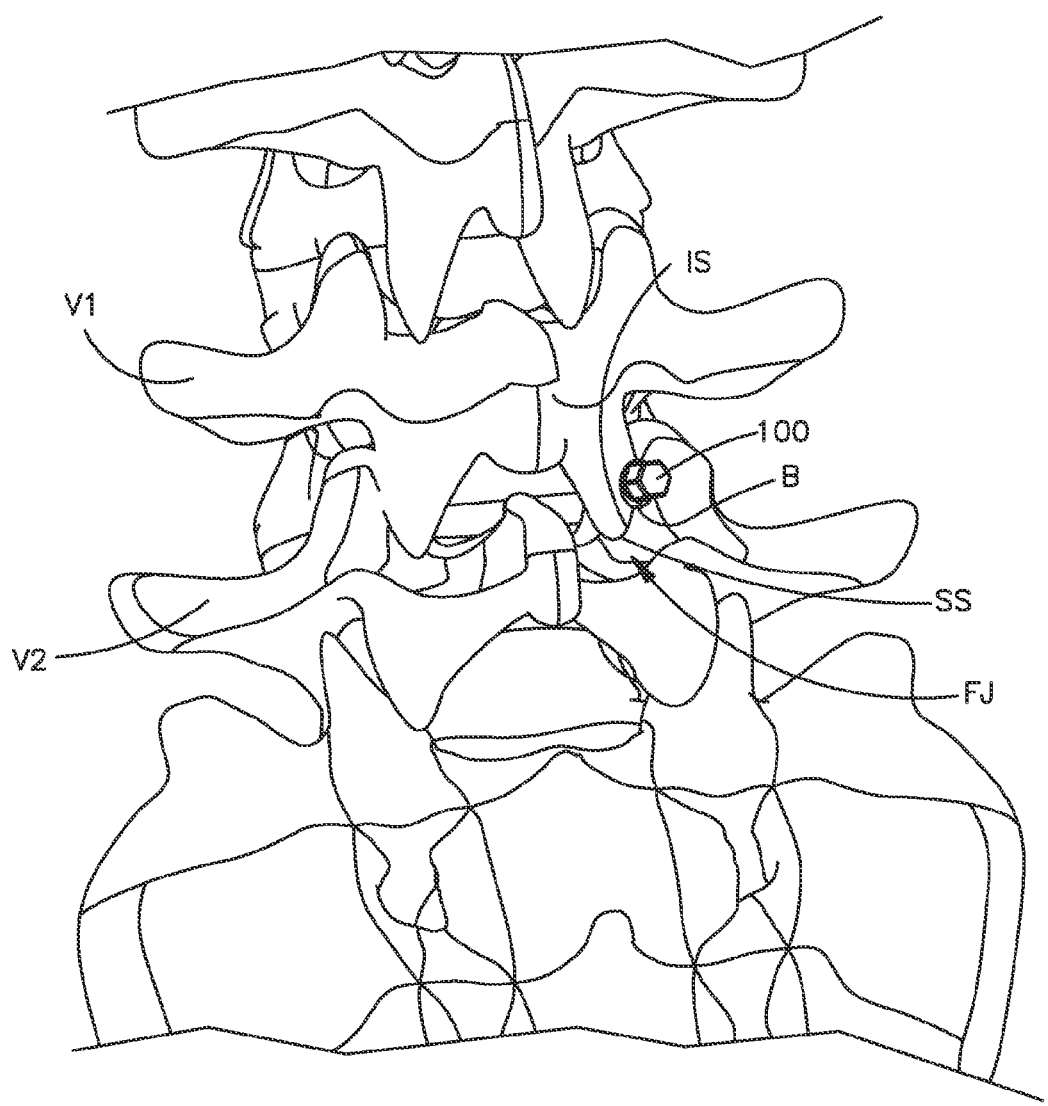
FIG. 20 is a perspective view of the implant illustrated in FIGS. 2A-C inserted into the facet joint.
Figure 22B:
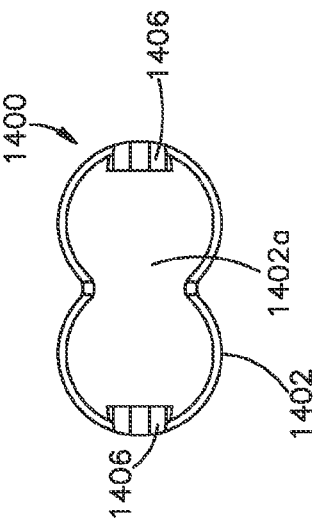
FIG. 22B is a top elevation view of the implant illustrated in FIG. 22A.
Figure 22D:
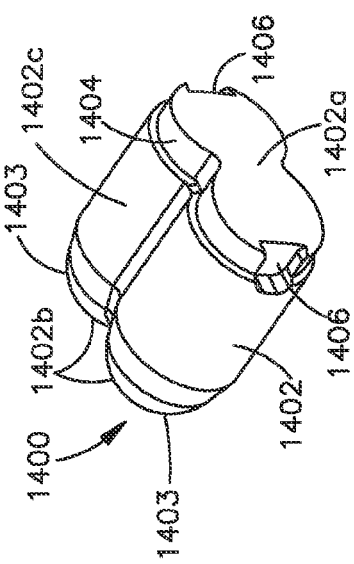
FIG. 22D is a rear elevation view of the implant illustrated in FIG. 22A.
Figure 22A:
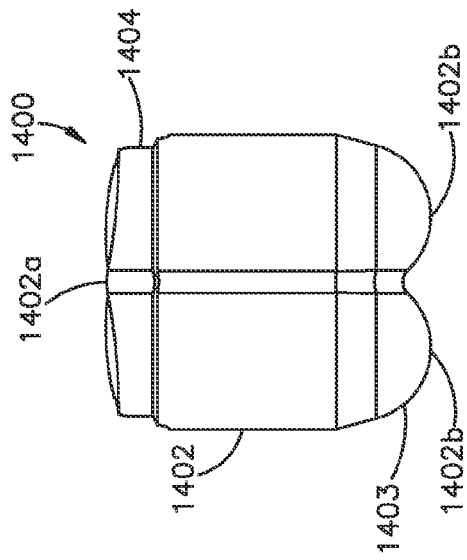
FIG. 22A is a side elevation view of a facet fusion implant constructed in accordance with yet another alternative embodiment.
Figure 22C:
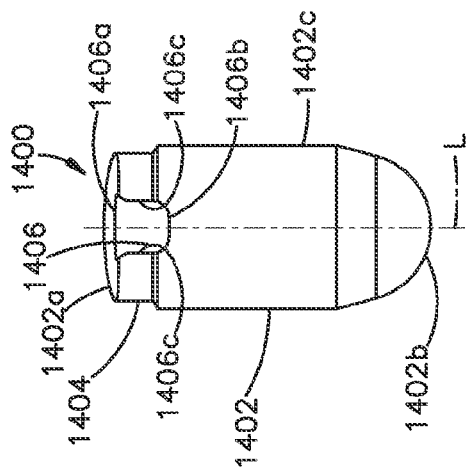
FIG. 22C is a perspective view of the implant illustrated in FIG. 22A.
Figure 23A:
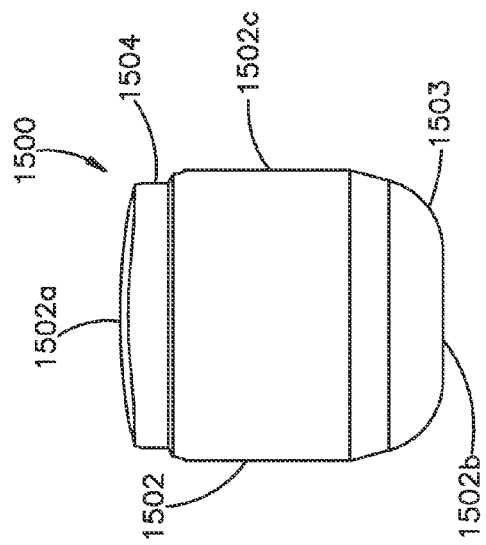
FIG. 23A is a side elevation view of a facet fusion implant constructed in accordance with yet another alternative embodiment.
Figure 23B:
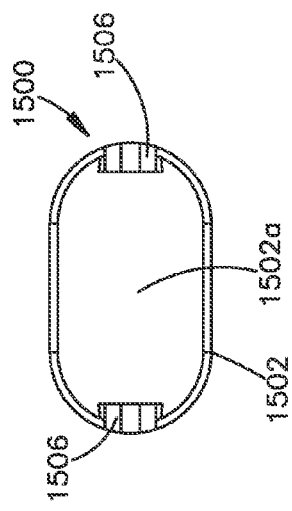
FIG. 23B is a top elevation view of the implant illustrated in FIG. 23A.
Figure 23C:
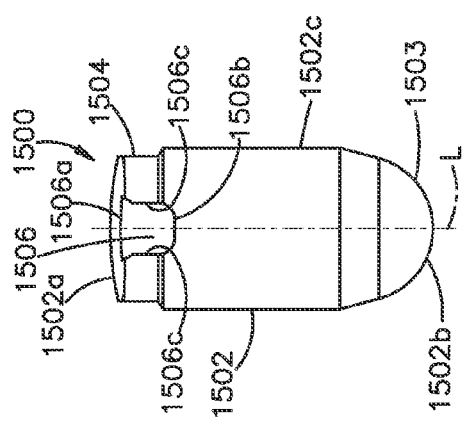
FIG. 23C is a perspective view of the implant illustrated in FIG. 23A.
Figure 23D:
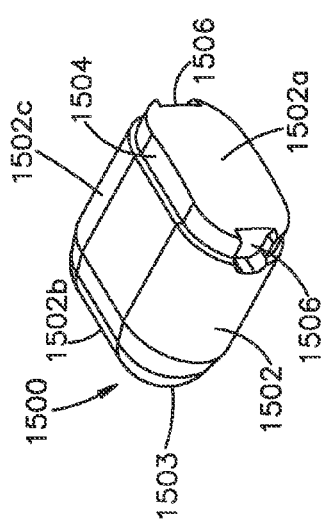
FIG. 23D is a rear elevation view of the implant illustrated in FIG. 23A.

Referring now to FIGS. 18-20, with the bore B in the facet joint FJ drilled and tapped, the implant 100 can be deployed into the facet joint FJ and inserted into position. The implant 100 can be deployed into the facet joint FJ using a driver shaft 1200. The implant 100 can be releasably coupled to the driver shaft 1200, and the driver shaft 1200 inserted into the cannulation 904 of the guide tube 900 and slidably advanced through the cannulation 904, thereby delivering the implant 100 to the facet joint FJ. A rotational force can then be applied to the driver shaft 1200 to drive the implant 100 into an inserted position in the bore B of the facet joint FJ.

In accordance with the illustrated embodiment, the driver shaft 1200 includes a substantially cylindrically shaped shaft body 1202 defining a proximal end 1202a and an opposed distal end 1202b. The shaft body 1202 can define a cannulated implant carrying portion 1204 that extends from the distal end 1202b in a direction toward the proximal end 1202a, a shank portion 1208 near the proximal end 1202a, and an intermediate portion 1206 that extends between the implant carrying and shank portions 1204, 1208, respectively. The implant carrying portion 1204 can define a cannulation 1210 that extends into the shaft body 1202 from the distal end 1202b in a direction toward the proximal end 1202a and extends along substantially the entirety of the length of the implant carrying portion 1204. The cannulation 1210 can be define an implant receptacle 1212 that extends into the shaft body 1202 from the distal end 1202b, the implant receptacle 1212 sized and configured to receive the engaging element of the head portion 104 of the implant 100. In the illustrated embodiment, the implant receptacle 1212 can define a hex shaped profile configured to receive the hex shaped engaging element of the head portion 104 of the implant 100.

The implant carrying portion 1204 can further define an implant carrying element 1214, the implant carrying element 1214 configured to releasably retain the implant 100 during delivery to the bore B in the facet joint FJ. For example, in the illustrated embodiment, the carrying element 1214 is defined as a resilient cantilevered tab 1216 defined near the distal end 1202b of the shaft body 1202. The tab 1216 can extend in a distal direction between a proximal tab end 1216a and an opposed distal tab end 1216b. The tab 1216 can be defined by a substantially "J" shaped groove 1218 defined through the shaft body 1202. The tab 1216 can have a contact tip 1220 and a thinned section 1222 defined by a slot 1224 defined in the inner surface of the tab 1216. The tab 1216 can be bent inward toward the center of the cannulation 1210, such that at least a portion of the contact tip 1220 projects into the cannulation 1210.

In use, the implant 100 can be releasably coupled to the driver shaft 1200 via the carrying element 1214. For example, the distal end 1202b of the shaft body 1202 is inserted over the head portion 104 of the implant 100. As the drive head is received in the implant receptacle 1212, at least a portion of the outer surface of the head portion 104 comes into contact with the contact tip 1220. The contact tip 1220 is biased outwardly away from the center of the cannulation 1210, applying a retention force substantially normal to the outer surface of the head portion 104. The retention force is sufficient to retain the implant 100 within the implant receptacle 1212. It should be appreciated that the driver shaft 1200 is not limited to the illustrated carrying element 1214, and that the driver shaft 1200 can be alternatively constructed using any other suitable implant carrying element configured to releasably couple the implant 100 to the driver shaft 1200, as desired. It should further be appreciated that the driver shaft 1200 can be alternatively constructed such that the cannulation 1210 extends through the entirety of the length of the shaft body 1202, for example if it were desirable to insert and operate the driver shaft 1200 over a guide wire such a the guide pin 500.

The implant carrying and intermediate portions 1204, 1206 of the shaft body 1202 can define an outer diameter that is sized to be approximately that of the cannulation 904 of the guide tube 900, but slightly narrower such that the implant carrying and intermediate portions 1204, 1206 of the driver shaft 1200 can be received in, and slidably translatable and rotatable in, the cannulation 904. The shaft body 1202 can define a raised annular collar 1226 at the intersection of the proximal end of the intermediate portion 1206 and the distal end of the shank portion 1208, the collar 1226 defining opposed proximal and distal surfaces 1226a, 1226b, respectively. The distal surface 1226b of the collar 1226 can define at least one, such as a plurality of locking elements configured to engage with the locking elements 916 of the guide tube 900. The distal surface 1226b of the illustrated driver shaft 1200 defines a plurality of locking teeth 1228 spaced around the distal surface 1226b.

The collar 1226 can be located on the shaft body 1202 at a particular distance from the distal end 1202b, such that as the driver shaft 1200 rotates, thereby driving the implant 100 into position in the bore B of the facet joint FJ, the distal surface 1226b of the collar 1226 will abut the proximal end 902a of the guide tube 900, causing the locking teeth 1228 to engage with the locking teeth 916 of the guide tube 900, thereby stopping the driver shaft 1200 from further advancing the implant 100, for example when the implant 100 has reached the desired insertion depth in the bore B, preventing the threads within the bore B and the threads 106 of the implant 100 from stripping, thereby reducing the likelihood of damaging the implant 100 via the driving process, and reducing the likelihood of breaking the engaging element of the head portion 104 of the implant 100. It should be appreciated that the driver shaft 1200 is not limited to the locking elements of the illustrated locking teeth 1228, and that the shaft body 1202 can be alternatively constructed with any other type of suitable locking elements as desired. It should further be appreciated that the driver shaft 1200 is not limited to the illustrated location of the collar 1226, and that the collar 1226 can alternatively be located at any other position along the length of the shaft body 1202, for instance to determine the insertion depth within the bore B of a respective facet fusion implant.

The shank portion 1208 of the shaft body 1202 can define at least one, such as a plurality of drive engaging elements 1230, the drive engaging elements 1230 configured to engage with complementary drive engaging elements of a driving instrument and/or device configured to apply torque to the driver shaft 1200, such as a handle, a motorized drill, or the like.

In use, the implant 100 can be releasably coupled to the carrying element 1214, and the driver shaft 1200 inserted into the cannulation 904 of the guide tube 900. The driver shaft 1200 can be translated through the cannulation 904 to deploy the implant 100 to the facet joint FJ, and in particular to the bore B. The driver shaft 1200 can be coupled to a driving instrument and/or device, such as a manually operated handle, before or after the driver shaft 1200 is inserted into the guide tube 900 and slidably advanced to the facet joint FJ. When the distal end 102b of the implant 100 enters the bore B, the driving instrument can be operated to apply torque to the driver shaft 1200 such that the threads 106 of the implant 100 engage with the threads tapped into the inner surface of the bore B, and the implant 100 is driven into the bore B.

The implant 100 can be rotatably advanced into the bore B in the facet joint FJ until the locking teeth 1228 of the driving shaft 1200 engage the locking teeth 916 of the proximal end 902a of the guide tube 900, at which point the implant 100 has been driven into a fully inserted position within the bore B. The driver shaft 1200 can then be operated to release the implant 100 from the carrying element 1214, for example by applying a force in a direction opposite from the insertion direction of the implant 100 sufficient to dislodge the head portion 104 of the implant from the implant receptacle 1212. The driver shaft 1200 can then be removed from the guide tube 900, and the guide tube 900 can be removed from the facet joint FJ, leaving the implant 100 in its inserted position within the facet joint FJ, as illustrated in FIG. 20.

It should be appreciated that while the above-described steps of the illustrated surgical implant insertion method refer to the insertion of a single implant 100 into the facet joint FJ on the right hand side of a patient's spine, that the method can further include repeating the above-described steps to insert a second implant 100 into the facet joint between the vertebrae V1, V2 on the opposed side of the patient's spine. It should further be appreciated that more than one implant 100-400 can be inserted into a single facet joint FJ, the implants 100-400 sized the same or differently. It should further still be appreciated that one or more implants 100-400 can be inserted into a single facet joint FJ along with one or more implants 1300-1900 described in more detail below. It should further still be appreciated that the implant insertion surgical method is not limited to the precise number and/or order of surgical method steps described in accordance with the illustrated embodiment, and that the surgical method can alternatively be carried out. Some steps of the surgical method may not be required, depending on patient anatomy, for instance the step of reaming the articular processes P1, P2, or tapping threads into the inner surface of the bore B. It should further still be appreciated that the surgical implant procedure can alternatively be performed omitting certain of the above-described implant insertion instruments.

Referring generally now to FIGS. 21A-27, facet fusion implants constructed in accordance with alternative embodiments are illustrated. In contrast to the implants 100-400, the facet fusion implants 1300-1900 are configured to be inserted into a facet joint FJ by application of at least one, such as a plurality of impaction forces to the implants 1300-1900. The facet fusion implant 1300 illustrated in FIGS. 21A-D includes an implant body 1302 having a proximal end 1302a, an opposed distal end 1302b, and an intermediate section 1302c that extends between the proximal and distal ends 1302a, 1302b. In accordance with the illustrated embodiment, the implant body 1302 is elongate between the proximal and distal ends 1302a, 1302b, respectively, along a longitudinal, or central axis L, and has a substantially bullet shaped body. That is, the illustrated body 1302 defines a substantially circular cross section in a plane perpendicular to the longitudinal axis L and a rounded tip 1303 at the distal end 1302b, for example a partially spherical tip 1303 (i.e., a tip 1303 defining the shape of a portion of a sphere). The body 1302 of the implant 1300 is sized to be received in a facet joint, and in particular in the gap between the inferior and superior facet articulation surfaces of a pair of adjacent vertebrae. The intermediate section 1302c of the body 1302 of the illustrated implant 1300 has a uniform cross-sectional profile. However, it should be appreciated that the implant 1300 can be alternatively constructed with an intermediate section 1302c having a non-uniform cross-sectional profile. For example, the intermediate section 1302c of the body 1302 could be tapered between the proximal and distal ends 1302a, 1302b.

Figure 36A:
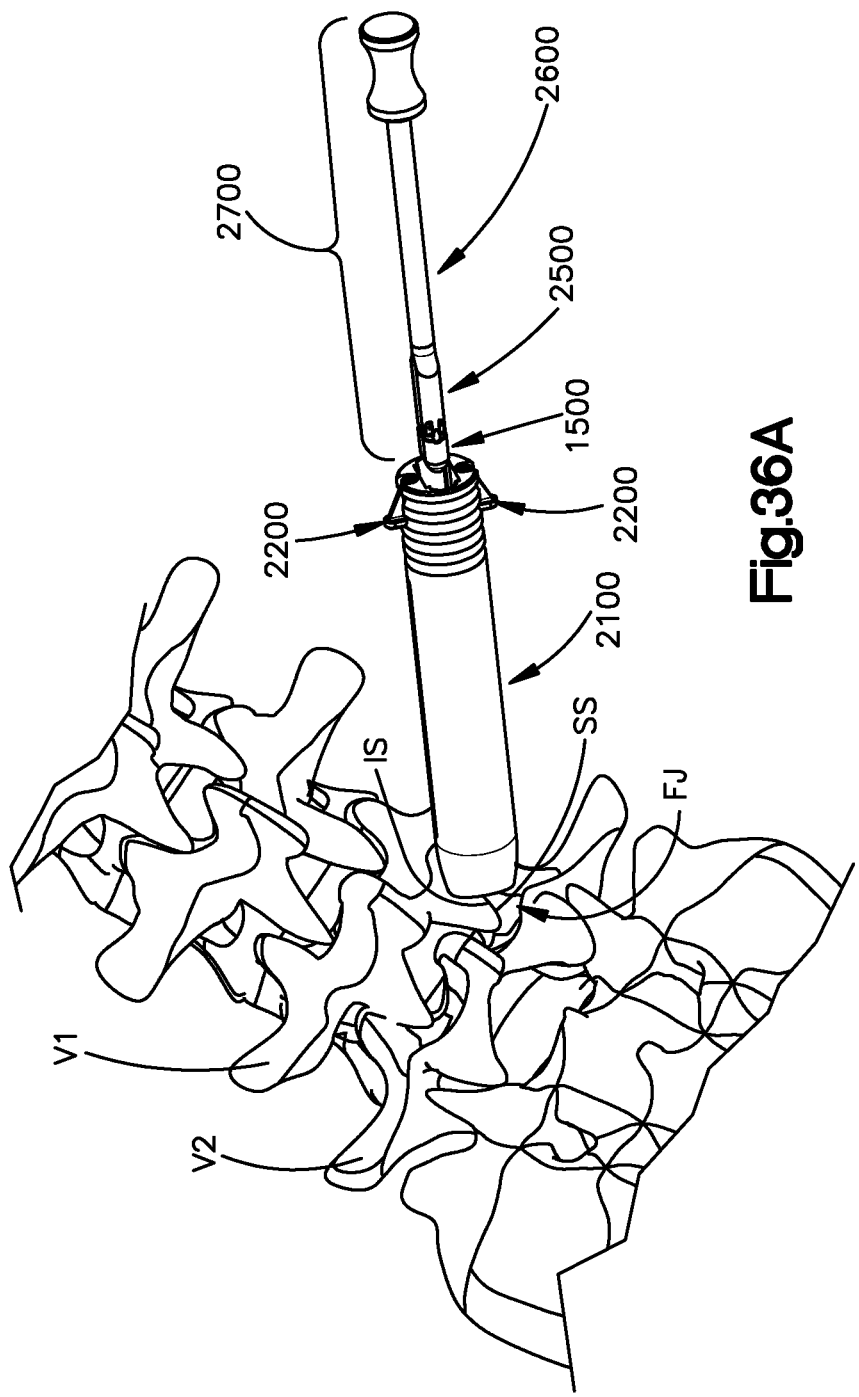
FIG. 36A is a perspective view of an implant inserter assembly including the implant illustrated in FIGS. 23A-D, a tamping inserter tip, and a tamping inserter, prior to insertion of the implant inserter assembly into the guide tube illustrated in FIGS. 31A-F.
Figure 36B:
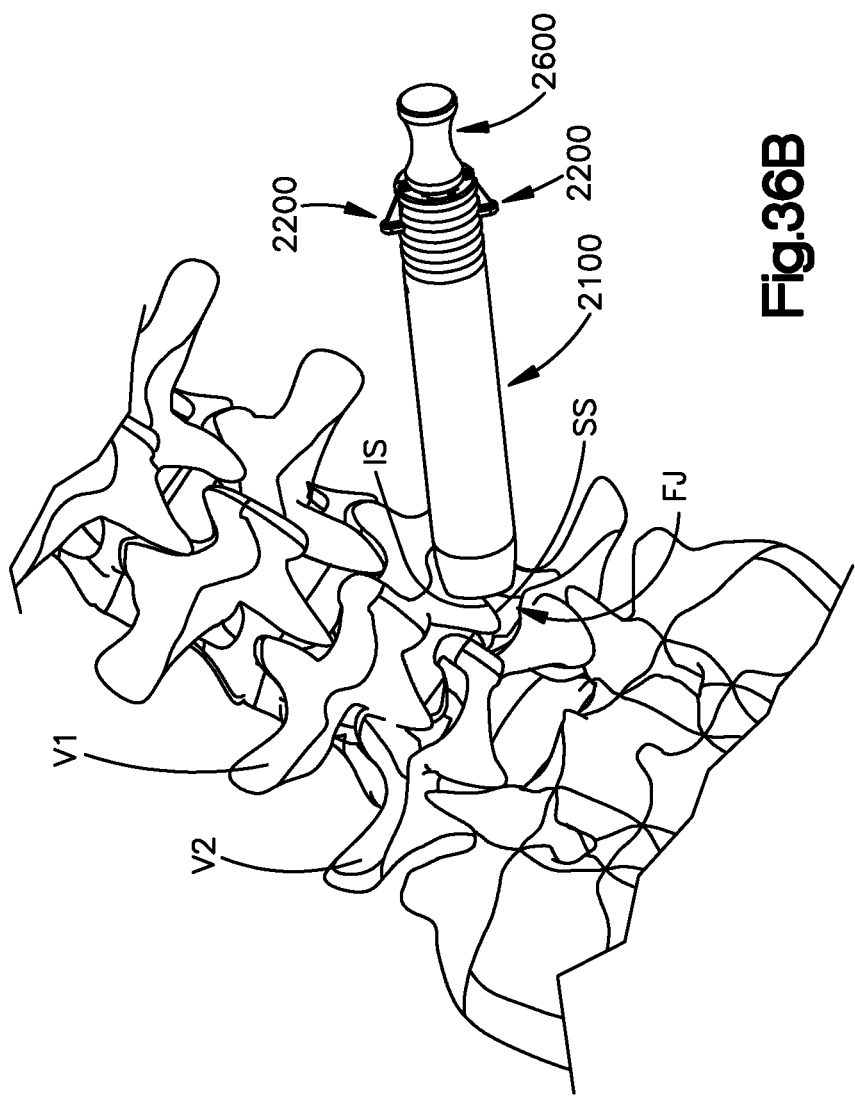
FIG. 36B is a perspective view of the implant inserter assembly illustrated in FIG. 36A, after the implant inserter assembly has been inserted into the guide tube illustrated in FIGS. 31A-F.
Figure 37C:
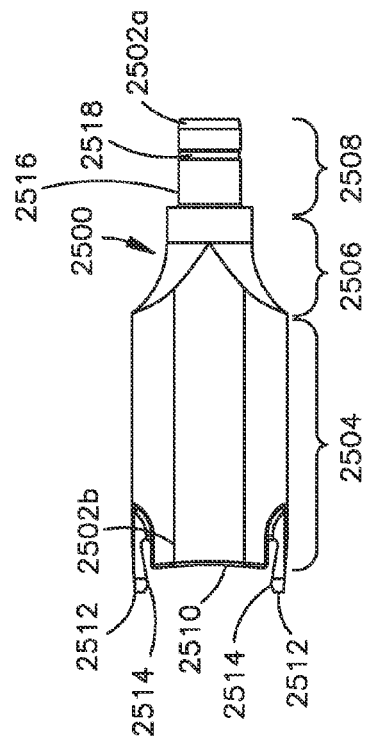
FIG. 37C is a side elevation view of the tamping inserter tip illustrated in FIG. 37A.
Figure 37D:
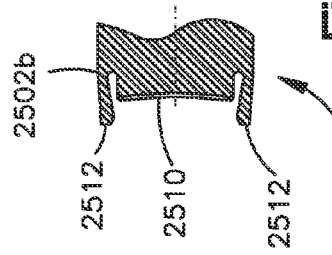
FIG. 37D is a side section view of the tamping inserter tip illustrated in FIG. 37A.
Figure 37A:
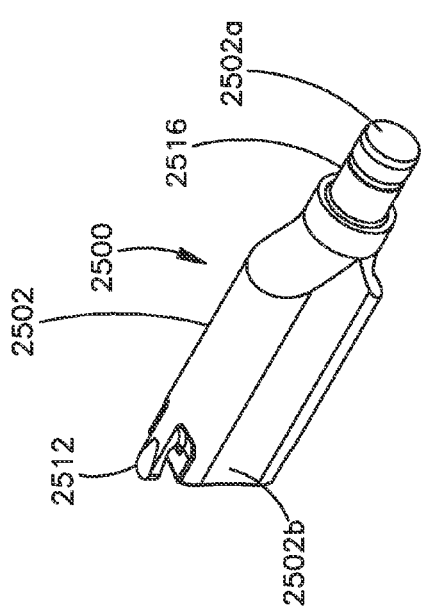
FIG. 37A is a perspective view of the tamping inserter tip illustrated in FIG. 36A.
Figure 37B:
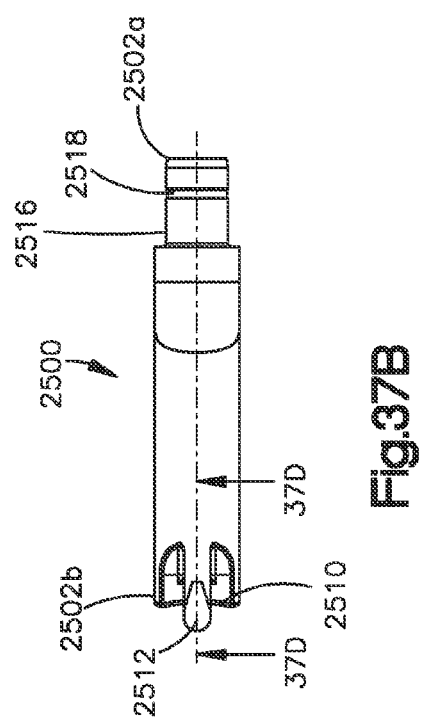
FIG. 37B is a top elevation view of the tamping inserter tip illustrated in FIG. 37A.

The body 1302 of the implant 1300 can include a head portion 1304 disposed at the proximal end 1302a. The head portion 1304 can be integral with the body 1302 or can be affixed thereto. The head portion 1304 can be constructed such that it defines a cross-sectional dimension that does not exceed a cross-sectional dimension of the intermediate portion 1302c of the body 1302, the cross-sectional dimensions measured in respective planes that are substantially perpendicular to the central axis L. For example, in accordance with the illustrated embodiment the head portion 1304 is constructed such that its cross-sectional dimension does not exceed the cross-sectional dimension of the intermediate portion 1302c of the body 1302, regardless of where the cross-sectional dimension of the head portion 1304 is measured. In other words, the head portion 1304 does not define a cross-sectional dimension that exceeds the outermost cross-sectional dimension of the intermediate portion 1302c of the body 1302. Constructing the head portion 1304 such that its cross-sectional dimension does not exceed the cross-sectional dimension of intermediate portion 1302c of the body 1302 can be advantageous to a surgeon inserting the implant 100. For example, when the implant 1300 is engaged with an insertion instrument, for instance the tamping inserter tip 2500 of the tamping inserter 2600 (see FIGS. 37A-38C), the implant 1300 and the insertion instrument define an uninterrupted outer profile (see FIG. 36A), allowing the implant 1300 and the tamping inserter tip 2500 to slide smoothly within the cannulation 2104 of the guide tube 2100 (see FIGS. 31A-F) through which the implant 1300 is delivered to the facet joint FJ (see FIGS. 36A-B).

The head portion 1304 can define, or carry an instrument engaging element configured to releasably engage with a complimentary engaging element of an insertion instrument, such that an impaction force applied to the insertion instrument is transmitted to the engaging element of the head portion 1304, thereby causing the implant 1300 to be advanced into a facet joint. For example, in accordance with the illustrated embodiment, the head portion 1304 defines an instrument engaging element in the form of a pair of recesses 1306 on opposed sides of the body 1302, the recesses 1306 configured to receive complementary grasping elements of an insertion instrument, as described in more detail below. As illustrated, the recesses can be elongate in a direction substantially parallel to that of the longitudinal axis L. The sides 1306c of the recesses 1306 can be tapered at their respective proximal ends 1306a, for example to guide the grasping elements of an insertion instrument into the recesses 1306 when the implant 1300 is coupled to the insertion instrument. The distal ends 1306b of the recesses 1306 can extend beyond the distal end of the head portion 1304 and into the intermediate section 1302c of the body 1302. It should be appreciated that the engaging element of the facet fusion implant 1300 is not limited to the illustrated pair of recesses 1306. For example, the head portion 1304 and/or intermediate portion 1302c can be alternatively constructed with any other internal and/or external engaging element as desired.

The implant 1300 is preferably constructed of allograft tissue, such as allograft bone. For example, the illustrated implant 1300 can be constructed of a combination of cortical and cancellous allograft bone. In particular, the head can be constructed of cortical bone, which is more suitable than cancellous bone for engagement with the insertion instrument and for absorbing any impaction or other forces the head portion 1304 of the implant 1300 may absorb during insertion of the implant 1300, while the remainder of the body 1302 of the implant can be constructed of cancellous bone, whose properties are more conducive to promoting fusion than those of cortical bone. The allograft bone can be demineralized in order to enhance the osteoinductive potential of the implant 1300, thereby enhancing its fusion promoting characteristics. It should be appreciated that the implant 1300 is not limited to being constructed of allograft bone, and that the implant 1300 can alternatively be constructed using any other biocompatible, implantable material as desired, including metals such as titanium, titanium alloy such as TAN, or stainless steel, polymers such as polyetheretherketone (PEEK), reinforced plastics, and the like.

Referring now to FIGS. 22A-D, a facet fusion implant 1400 constructed in accordance with another alternative embodiment is illustrated. The implant 1400 can be constructed similarly to the implant 1300, but with the body 1402 of the implant 1400 defining a different geometry. For the sake of simplicity, reference numbers used in FIGS. 21A-D to refer to the implant 1300 that correspond to like elements of the implant 1400 are repeated in FIGS. 22A-D, incremented by 100. In accordance with the illustrated embodiment, the body 1402 of the implant 1400 can have a bi-cylindrical shape, that is the body 1402 can be configured to be similar to that of two implants 1300 fused together such that at least a peripheral portion of each of their respective bodies overlap along the longitudinal axis L, resulting in an implant body 1402 that defines a pair of rounded tips 1403 and has a generally "8" shaped cross section in a plane perpendicular to the longitudinal axis L. The implant 1400 provides a greater amount of implant surface area that can be placed in contact with the articular surfaces of the facet joint FJ than that of the implant 1300, thereby increasing the amount of implant surface area in the facet joint FJ across which fusion can occur when compared to the implant 1300.

Referring now to FIGS. 23A-D, a facet fusion implant 1500 constructed in accordance with still another alternative embodiment is illustrated. The implant 1500 can be constructed similarly to the implant 1300, but with the body of the implant 1500 defining a different geometry. For the sake of simplicity, reference numbers used in FIGS. 21A-D to refer to the implant 1300 that correspond to like elements of the implant 1500 are repeated in FIGS. 23A-D, incremented by 200. In accordance with the illustrated embodiment, the body 1502 of the implant 1500 can be configured to be similar to an implant 1300 that is halved along the longitudinal axis L, with a generally rectangular body portion having a substantially similar longitudinal cross section disposed between the respective halves, resulting in an implant body 1502 with a generally oval shaped lateral cross section. The implant 1500 provides a greater amount of implant surface area that can be placed in contact with the articular surfaces of the facet joint FJ than that of the implant 1300, thereby increasing the amount of implant surface area in the facet joint FJ across which fusion can occur when compared to the implant 1300.

Figure 24:
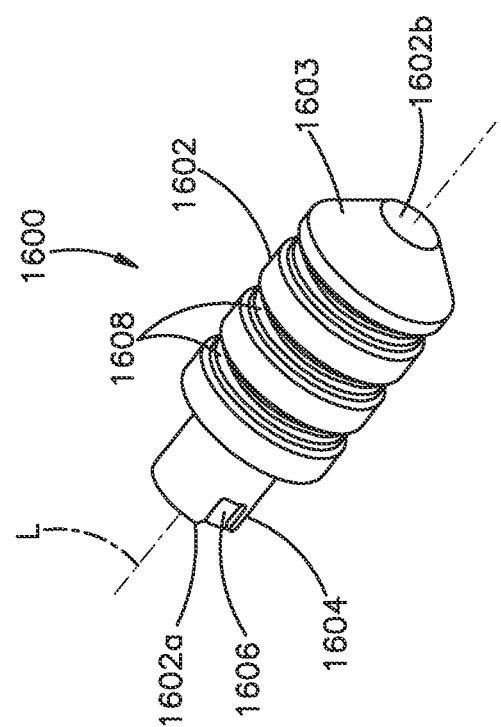
FIG. 24 is a perspective view of a facet fusion implant constructed in accordance with yet another alternative embodiment.

Referring now to FIG. 24, a facet fusion implant 1600 constructed in accordance with still another alternative embodiment is illustrated. The implant 1600 can be constructed similarly to the implant 1300, but with the body 1602 of the implant 1600 defining a different geometry. For the sake of simplicity, reference numbers used in FIGS. 21A-D to refer to the implant 1300 that correspond to like elements of the implant 1600 are repeated in FIG. 24, incremented by 300. In accordance with the illustrated embodiment, the distal end 1602b of the body 1602 defines a frustoconical tip 1603. The body 1602 of the implant can define at least one, such as a plurality of circumferential grooves 1608, the grooves 1608 configured to minimize migration of the implant 1600 when the implant 1600 is inserted into a facet joint FJ.

Figure 25:
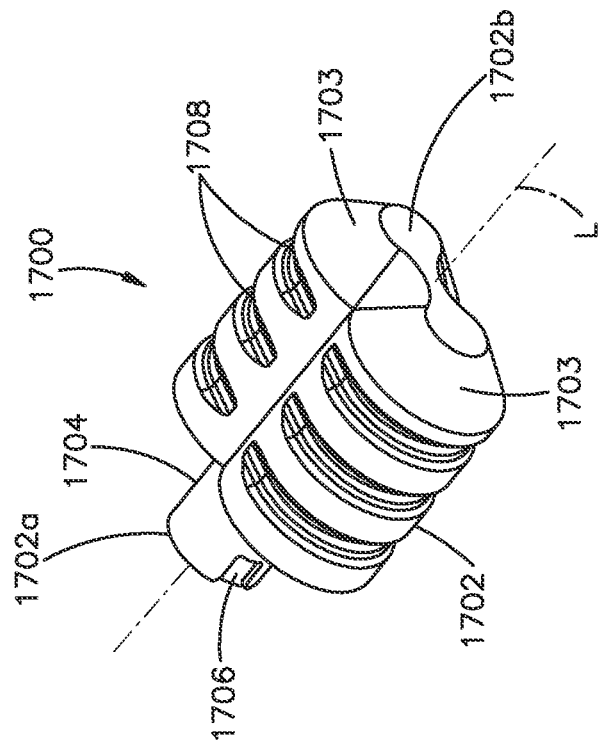
FIG. 25 is a perspective view of a facet fusion implant constructed in accordance with yet another alternative embodiment.

Referring now to FIG. 25, a facet fusion implant 1700 constructed in accordance with still another alternative embodiment is illustrated. The implant 1700 can be constructed similarly to the implant 1600, but with the body 1702 of the implant 1700 defining a different geometry. For the sake of simplicity, reference numbers used in FIG. 24 to refer to the implant 1600 that correspond to like elements of the implant 1700 are repeated in FIG. 25, incremented by 100. In accordance with the illustrated embodiment, the body 1702 of the implant 1700 can be configured to be similar to that of two implants 1600 fused together such that at least a peripheral portion of each of their respective bodies overlap along a direction substantially parallel to that of the longitudinal axis L, resulting in an implant body 1702 that defines a pair of substantially frustoconical tips 1703 and has a generally "8" shaped cross section in a plane perpendicular to the longitudinal axis L. The implant 1700 provides a greater amount of implant surface area that can be placed in contact with the articular surfaces of the facet joint FJ than that of the implant 1600, thereby increasing the amount of implant surface area in the facet joint FJ across which fusion can occur when compared to the implant 1600.

Figure 26:
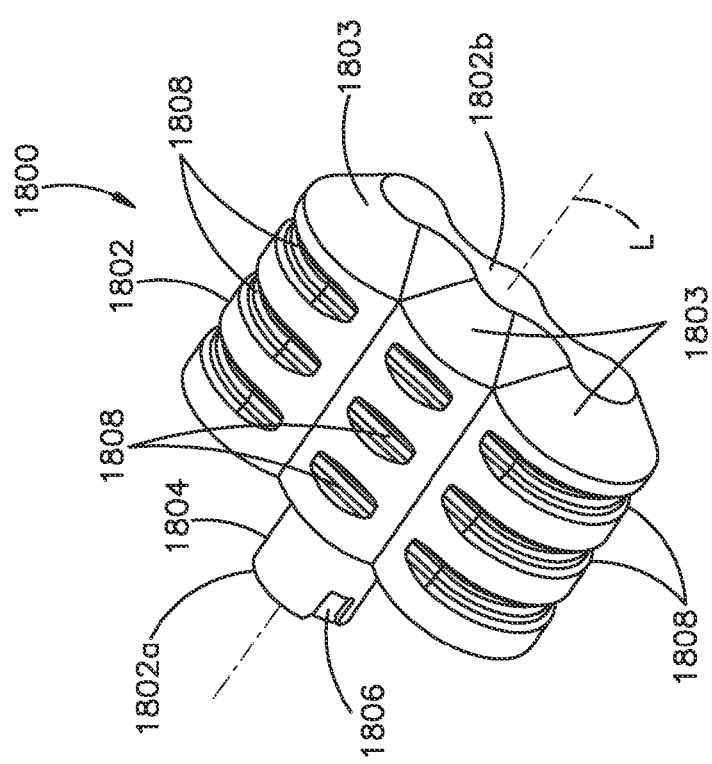
FIG. 26 is a perspective view of a facet fusion implant constructed in accordance with yet another alternative embodiment.

Referring now to FIG. 26, a facet fusion implant 1800 constructed in accordance with another alternative embodiment is illustrated. The implant 1800 can be constructed similarly to the implant 1600, but with the body of the implant 1800 defining a different geometry. For the sake of simplicity, reference numbers used in FIG. 24 to refer to the implant 1600 that correspond to like elements of the implant 1900 are repeated in FIG. 26, incremented by 200. In accordance with the illustrated embodiment, the body 1802 of the implant 1800 can have a tri-cylindrical shape, that is the body 1802 can be configured to be similar to that of three implants 1600 fused together such that at least a peripheral portion of each of the bodies of the outermost implants 1600 overlap with corresponding opposed peripheral portions of the center implant 1600 along a direction that is substantially parallel to that of the central axis L, resulting in an implant body 1802 that defines three substantially frustoconical tips 1803. The implant 1800 provides a greater amount of implant surface area that can be placed in contact with the articular surfaces of the facet joint FJ than that of the implant 1600, thereby increasing the amount of implant surface area in the facet joint FJ across which fusion can occur when compared to the implant 1600.

Figure 27:
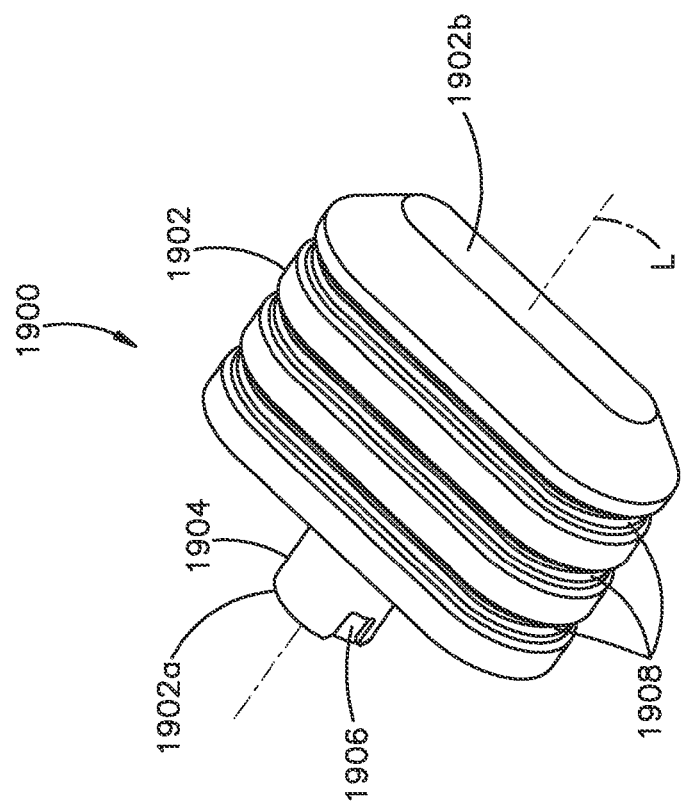
FIG. 27 is a perspective view of a facet fusion implant constructed in accordance with yet another alternative embodiment.

Referring now to FIG. 27, a facet fusion implant 1900 constructed in accordance with still another alternative embodiment is illustrated. The implant 1900 can be constructed similarly to the implant 1600, but with the body 1902 of the implant 1900 defining a different geometry. For the sake of simplicity, reference numbers used in FIG. 24 to refer to the implant 1600 that correspond to like elements of the implant 1900 are repeated in FIG. 27, incremented by 300. In accordance with the illustrated embodiment, the body 1902 of the implant 1900 can be configured to be similar to an implant 1600 that is halved along the central axis L, with a generally rectangular body portion having a substantially similar longitudinal cross section disposed between the respective halves, resulting in an implant body 1902 with a generally oval shaped lateral cross section. The implant 1900 provides a greater amount of implant surface area that can be placed in contact with the articular surfaces of the facet joint FJ than that of the implant 1600, thereby increasing the amount of implant surface area in the facet joint FJ across which fusion can occur when compared to the implant 1600.

Referring generally to FIGS. 28-39, an example surgical method for inserting a facet fusion implant, such as the above-described implants 1300-1900, is illustrated. For the sake of simplicity, the surgical method is illustrated and described herein with reference to the insertion of a single one of the above-described facet fusion implant 1500, but it should be appreciated that any number of the implants 1300-1900 can be similarly inserted utilizing the surgical method described herein. The surgical method can be performed as an open procedure, a minimally invasive procedure, for instance using tubular retractors or percutaneous techniques and/or instrumentation, or any combination thereof. It should be appreciated that the implants 1300-1900 and the method of surgically inserting the implants 1300-1900 are not limited to the lumbar region of the spine as illustrated, and that the facet fusion implants 1300-1900 and associated surgical insertion method and instrumentation can be utilized to insert the implants 1300-1900 into any other suitable region of the spine as desired.

At the outset of the minimally invasive facet fusion implant insertion procedure, a degenerated or otherwise unhealthy facet joint, such as the facet joint FJ defined by the first and second vertebrae V1, V2 is identified within the patient. The facet joint FJ can be identified by fluoroscopy, x-ray imaging, magnetic resonance imaging (MRI), or the like. Once the affected facet joint FJ is identified and located within the patient, a small incision is made to permit the insertion of implant insertion instrumentation into the facet joint FJ. A guide wire, such as a Kirschner wire (or "K-wire") can be placed through the incision and inserted into position within the facet joint FJ. The guide wire can be impacted into place in the facet joint FJ, for example between the inferior and superior articulation surface IS, SS, respectively, of the first and second vertebrae V1, V2. In its inserted position, the guide wire can define an insertion trajectory to the surgical site along which the implant 1500 and implant insertion instruments used in subsequent steps of the surgical insertion method can be delivered to the facet joint FJ, as described in more detail below. Preferably, the guide wire is inserted into substantially the center of the facet joint FJ.

The guide wire, and the other implant insertion instruments described below for use in the facet fusion implant surgical insertion method are preferably constructed of biocompatible metals such as titanium, titanium alloy such as TAN, and/or stainless steel. Of course the individual insertion instruments can be made of the same or different metals, in any combination. Furthermore, it should be appreciated that the implant insertion instruments are not limited to construction with metal, and can alternatively be constructed of any other suitable biocompatible material as desired.

Referring now to FIGS. 28-29C, a facet finder 2000 can be inserted over the guide wire and slidably advanced to the facet joint FJ. The facet finder 2000 can be utilized to further aid the surgeon in identifying characteristics of the facet joint FJ, for instance by locating a plane of the facet joint FJ as defined between the inferior and superior articulation surfaces IS, SS, respectively.

In accordance with the illustrated embodiment, the facet finder 2000 includes a finder body 2002 having a substantially oval shaped lateral cross section, matched to that of the implant 1500, the finder body 2002 defining a proximal end 2002a, an opposed distal end 2002b, and opposed upper and lower surfaces 2002c, 2002d. It should be appreciated that the finder body 2002 can be alternatively constructed to match the lateral cross section of any of the implants 1300, 1400, or 1600-1900 as desired. Matching the cross section of the implant 1300-1900 to that of the facet finder can be useful for implant sizing purposes, as described above with respect to the joint finder 700.

The finder body 2002 defines a cannulation 2004 therethrough along a longitudinal, or central axis L of the finder body 2002, the diameter of the cannulation 2004 sized such that the guide wire is slidably received in the cannulation 2004 when the facet finder 2000 is inserted over the guide wire. It should be appreciated that the cannulation 2004 need not be located in the center of the finder body 2002 as illustrated, and that the facet finder 2000 can alternatively be constructed with the cannulation 2004 offset with respect to the central axis L. For example, it may be desirable to offset the cannulation 2004 with respect to the central axis L (i.e., the center of the finder body 2002) so as to cause more or less of the surface area of the implant 1500 to contact either the superior or inferior articulation surfaces SS, IS of the facet joint FJ. The finder body 2002 of the illustrated embodiment defines a slot 2006, elongate in a direction substantially parallel to that of the longitudinal axis L, that extends into the bottom surface 2002d of the finder body 2002, the slot 2006 open to the cannulation. The slot 2006 can operate as a window to view the guide wire.

The distal end 2002b of the finder body 2002 can be constructed for insertion into the plane of the facet joint FJ. For instance, the distal end 2002b of the finder body 2002 of the illustrated facet finder 2000 can include a pair of legs 2008 that extend from the distal end 2002b along a direction that is substantially parallel to the longitudinal axis L. The legs 2008 can be located on opposed sides of the distal end 2002b of the finder body 2002, and can have a height H that is substantially equal to the width of the gap defined between the inferior and superior articulation surfaces IS, SS of the facet joint FJ. The upper and lower surfaces of the legs 2008 can be tapered at the distal ends thereof to form tips 2010, the tips 2010 configured to ease insertion of the legs 2008 into the gap in the facet joint FJ. The proximal end 2002a of the finder body 2002 can define at least one, such as a plurality of gripping elements, the gripping elements configured to facilitate the gripping and maneuvering of the facet finder 2000 as it is inserted over the guide wire and into the facet joint FJ. For example, the proximal end 2002a of the finder body 2002 of the illustrated facet finder 2000 defines a thumb grip 2012 on each of the upper and lower surfaces 2002c, 2002d. It should be appreciated that the facet finder 2000 is not limited to the gripping elements of the illustrated thumb grips 2012, and that the finder body 2002 can be alternatively constructed with any other type of suitable gripping elements as desired.

In operation, the facet finder 2000 can be inserted over the guide wire and slidably advanced to the facet joint FJ. As the legs 2008 approach the facet joint FJ, the facet finder 2000 can be rotated about the guide wire until the legs 2008 are aligned with the plane of the facet joint FJ (i.e., aligned with the gap between the inferior and superior articulation surfaces IS, SS). With the legs 2008 properly aligned, the facet finder 2000 can be inserted into the facet joint FJ until the facet finder 2000 is seated on the surfaces of the articular processes of the facet joint FJ. If necessary, the facet finder 2000 can be impacted in order to advance it into the facet joint FJ, for example with a mallet or the like. It should be appreciated that use of the guide wire can be omitted if desired. In other words, the facet finder 2000 can be inserted into the facet joint FJ without the use of a guide wire.

Referring now to FIGS. 30A-32C, once the facet finder 2000 is inserted into the facet joint FJ and seated against the surfaces of the articular processes, a guide tube 2100 can be inserted over the facet finder 2000 and guide wire and slidably advanced to the facet joint FJ. When inserted into the facet joint FJ, the guide tube 2100 can be utilized as a portal through which implant insertion instruments can be inserted in order to bore the facet joint FJ, and to insert the implant 1500 into the facet joint FJ, as described in more detail below.

Figure 31A:
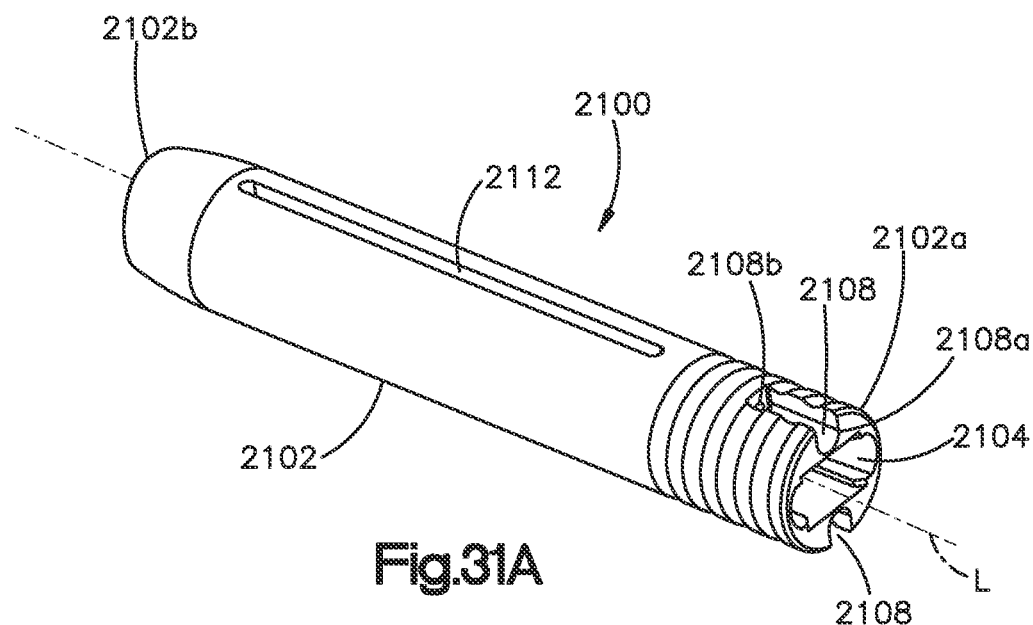
FIG. 31A is a perspective view of the guide tube illustrated in FIG. 30A.
Figure 31B:
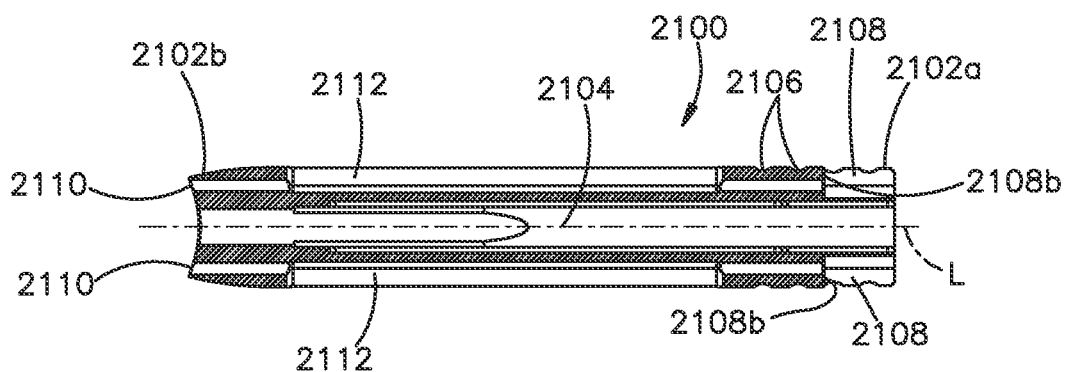
FIG. 31B is a side section view of the guide tube illustrated in FIG. 31A.
Figure 31C:
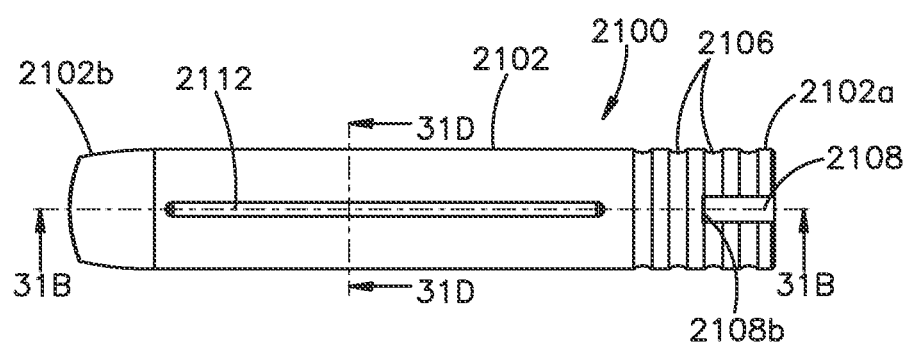
FIG. 31C is a top elevation view of the guide tube illustrated in FIG. 31A.
Figure 31D:
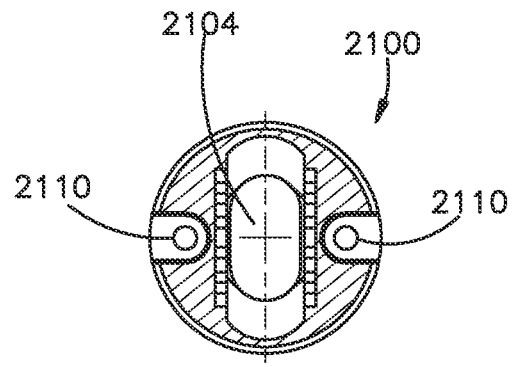
FIG. 31D is a front section view of the guide tube illustrated in FIG. 31A.
Figure 31E:
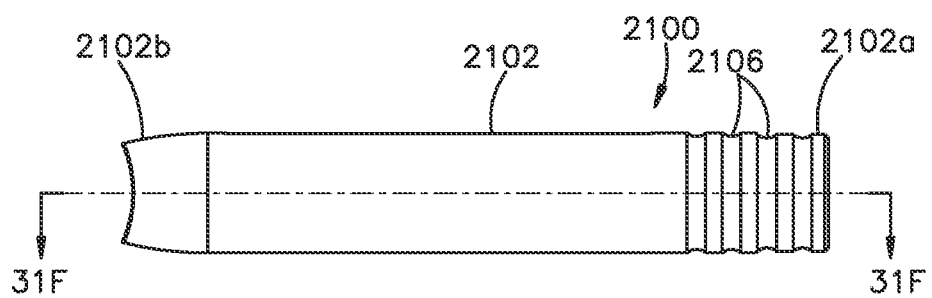
FIG. 31E is a side elevation view of the guide tube illustrated in FIG. 31A.
Figure 31F:
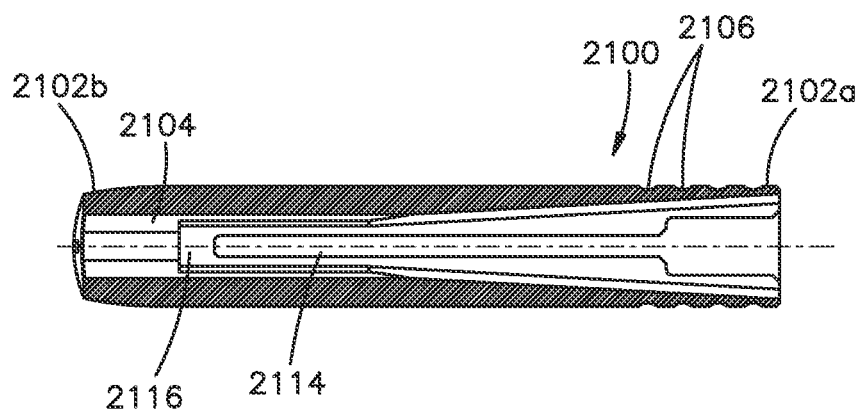
FIG. 31F is a top section view of the guide tube illustrated in FIG. 31A.

In accordance with the illustrated embodiment, the guide tube 2100 includes a substantially cylindrically shaped tube body 2102 defining a proximal end 2102a and an opposed distal end 2102b. The tube body 2102 defines a cannulation 2104 therethrough along the longitudinal axis L, the cross-sectional geometry of the cannulation 2104 sized and configured such that the implant 1500 can be deployed to the facet joint through the cannulation 2104, and such that the facet finder 2000 is slidably received in the cannulation 2104 when the guide tube 2100 is inserted over the facet finder 2000. As illustrated in FIG. 31F, the cannulation 2104 can be laterally tapered between the distal and proximal ends 2102b, 2102a, such that the cross-sectional dimension of the cannulation 2104 at the proximal end 2102a is greater than that at the distal end 2102b. At least one, such as a plurality of guide channels can be defined on laterally opposed sides of the tapered portion of the cannulation. For instance, the tube body 2102 of the illustrated guide tube 2100 defines a first pair of straight guide channels 2114 that extend distally from the proximal end 2102a of the tube body 2102, and a second pair of tapered guide channels 2116 that extend distally from the proximal end 2102a of the tube body 2102. The first and second guide channels 2114, 2116 can be configured to receive complementary guide bosses 2307, 2305, respectively, defined on a drill guide 2300 (see FIG. 34). Alternatively, the guide body 2102 can define more or fewer guide channels. The tapered portion of the cannulation 2104 and the first and second guide channels 2114, 2116, enable a milling instrument to be translated back and forth within the cannulation 2104, as described in more detail below. It should be appreciated that the guide tube 2100 is not limited to the illustrated cannulation 2104 configured to receive the implant 1500 or the first and second guide channels 2114, 2116, and that the cannulation 2104 and/or the guide channels can be alternatively constructed with any other geometry suitable to receive any other implants, such as the implants 1300-1900.

The distal end 2102b of the tube body 2102 can be constructed to seat against the surfaces of the articular processes of the facet joint FJ. For instance, the distal end 2102b of the tube body 2102 of the illustrated guide tube 2100 can define a curved profile configured to seat against the surfaces of the articular processes of the facet joint FJ.

The proximal end 2102a of the tube body 2102 can define at least one, such as a plurality of gripping elements, the gripping elements configured to facilitate the gripping and maneuvering of the guide tube 2100 as it is inserted over the facet finder 2000 and into the facet joint FJ. For example, the proximal end 2102a of the tube body 2102 of the illustrated guide tube 2100 defines a plurality of annular gripping grooves 2106 spaced inwardly from the proximal end 2102a of the tube body 2102. It should be appreciated that the guide tube 2100 is not limited to the gripping elements of the illustrated grooves 2106, and that the tube body 2102 can be alternatively constructed with any other type of suitable gripping elements as desired.

The proximal end 2102a of the tube body 2102 can further define a pair of longitudinally elongate grooves 2108 on opposed sides of the tube body 2102 that extend into the outer surface, the grooves 2108 having distal ends 2108b and opposed proximal ends 2108 open at the proximal end 2102a of the tube body 2102, the grooves 2108 configured to receive the respective wings 2208 of a pair of fixation pins 2200. The tube body 2102 can further define a pair of bores 2110 in opposed sides of the body 2102 that extend through the body 2102 from the distal end 2102b along a direction that is substantially parallel to that of the longitudinal axis L and open to the grooves 2108, the bores 2110 sized to slidably receive the pin bodies 2202 of the fixation pins 2200. The tube body 2102 of the illustrated embodiment further defines a pair of slots 2112 on opposed sides of the tube body 2102 that extend into the outer surface of the tube body 2102, the slots 2112 elongate along a direction that is substantially parallel to that of the longitudinal axis L and radially aligned with and open to the bores 2110. The slots 2112 can operate as windows to view the respective fixation pin 2200 inserted in each bore 2110.

In accordance with the illustrated embodiment, the fixation pin 2200 includes a substantially cylindrically shaped pin body 2202 defining a proximal end 2202a and an opposed distal end 2202b. The distal end 2202b of the pin body 2202 can be constructed with a tapered and/or narrowed cross-sectional dimension, so as to define a trocar-like tip 2204, the tip 2204 configured to be inserted into the underlying bony surfaces of the articulation processes of the facet joint FJ. The proximal end 2202a of the pin body 2202 can define an impaction element 2206, the impaction element 2206 configured to be impacted by a mallet or another impaction instrument. The impaction element 2206 can be integral to the pin body 2202 or separate and affixed thereto. The impaction element can define a lateral wing 2208 that extends radially from the impaction element, the wing 2208 configured to be received in a respective groove 2108 of the guide tube 2100. The wing 2208 can define a distal foot 2210 configured to abut the distal end 2108b of a respective groove 2108, as described in more detail below.

In operation, the guide tube 2100 can be inserted over the facet finder 2000 and slidably advanced to the facet joint FJ until the distal end 2102b is seated against the surfaces of the articular processes of the facet joint FJ. Once seated, the guide tube 2100 can be anchored in its seated position with a pair of fixation pins 2200. A fixation pin can be inserted tip first into each of the respective bores 2110 of the tube body 2102, and slidably advanced to the surfaces of the articular processes of the facet joint FJ. The tips 2204 of the fixation pins 2200 can be advanced into the articular processes by applying one or more impaction forces to the proximal ends of the impaction elements. The wings 2208 of the fixation pins 2200 can be received in the grooves 2108 as the fixation pins 2200 are driven into the articular processes. As the fixation pins 2200 advance into the articular processes, the wings 2208 will advance in the respective grooves 2108 until the distal foot 2210 of each wing 2208 abuts the distal end 2108b of its respective groove. In this way, the distal ends 2108b of the grooves 2108 act as stops to prevent the fixation pins 2200 from advancing further into the articulation processes once an appropriate depth has been reached. It should be appreciated that the fixation pins 2200 can be inserted into the bores 2110 before or after the guide tube 2100 is seated at the facet joint FJ.

With the guide tube 2100 seated and anchored at the facet joint FJ, the facet finder 2000 and the guide wire can be removed from the facet joint FJ and slid out of the guide tube 2100, while leaving the guide tube 2100 in its seated and anchored position. The cannulation 2104 of the guide tube 2100 can be used as a surgical access portal for the remaining steps of the implant insertion method, as described in more detail below.

Figure 33:
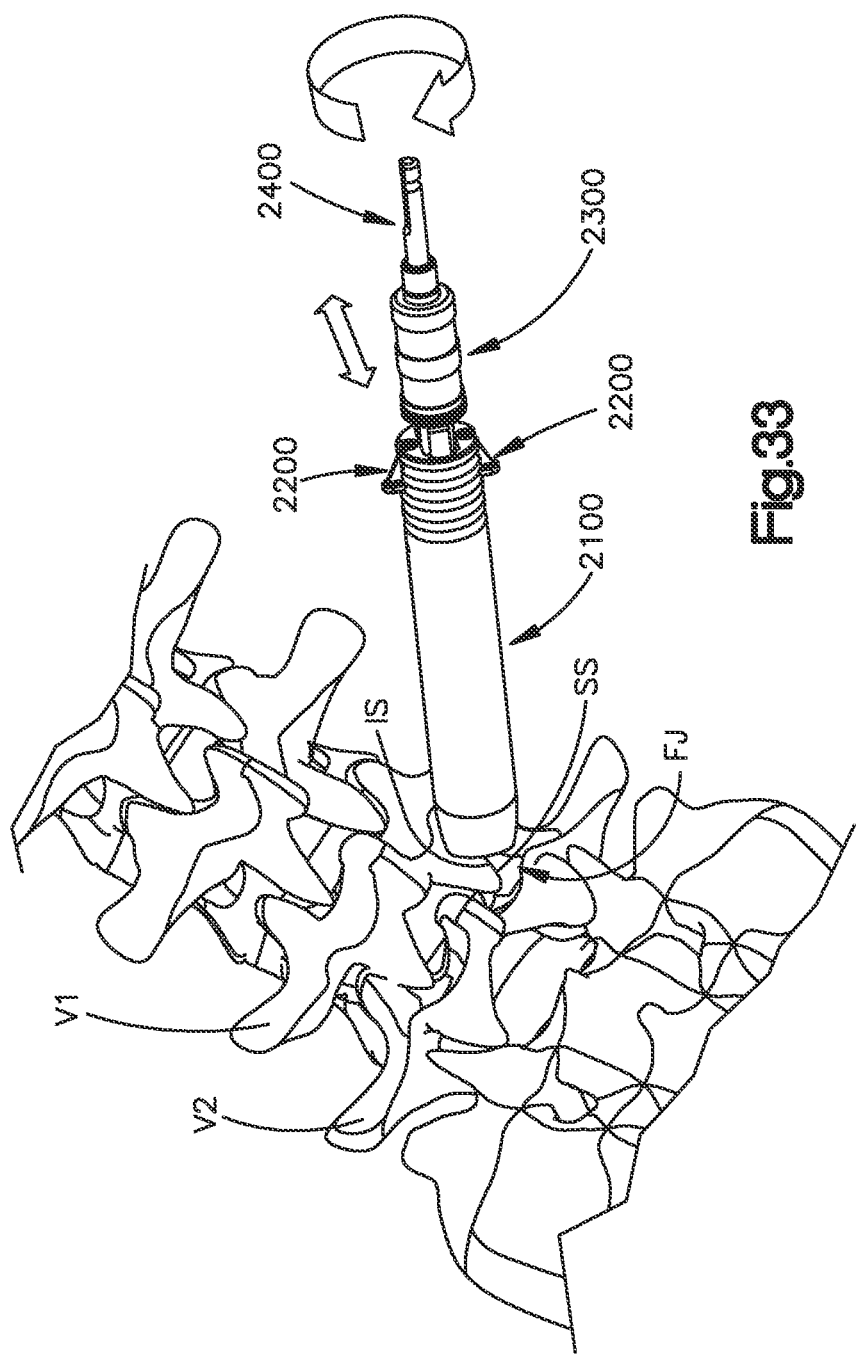
FIG. 33 is a perspective view of a drill guide and milling bit inserted into the guide tube illustrated in FIGS. 31A-F.
Figure 34:
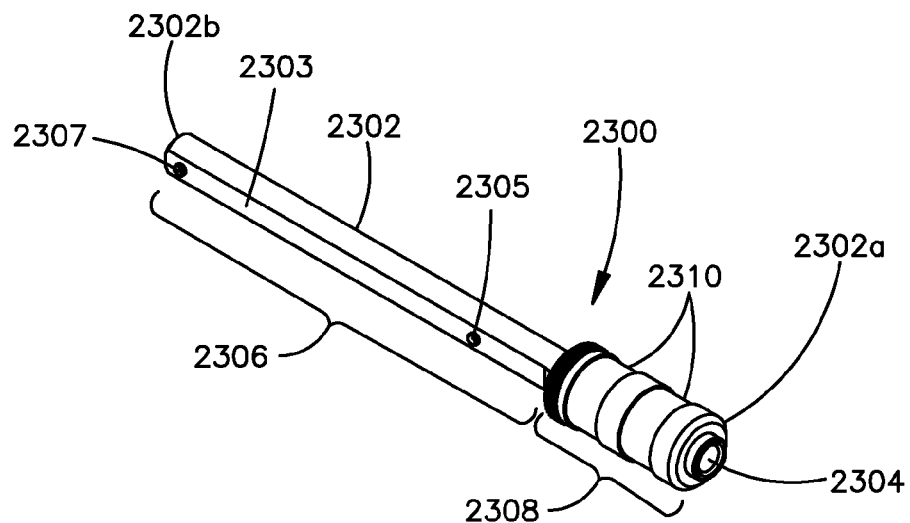
FIG. 34 is a perspective view of the drill guide illustrated in FIG. 33.
Figure 35:
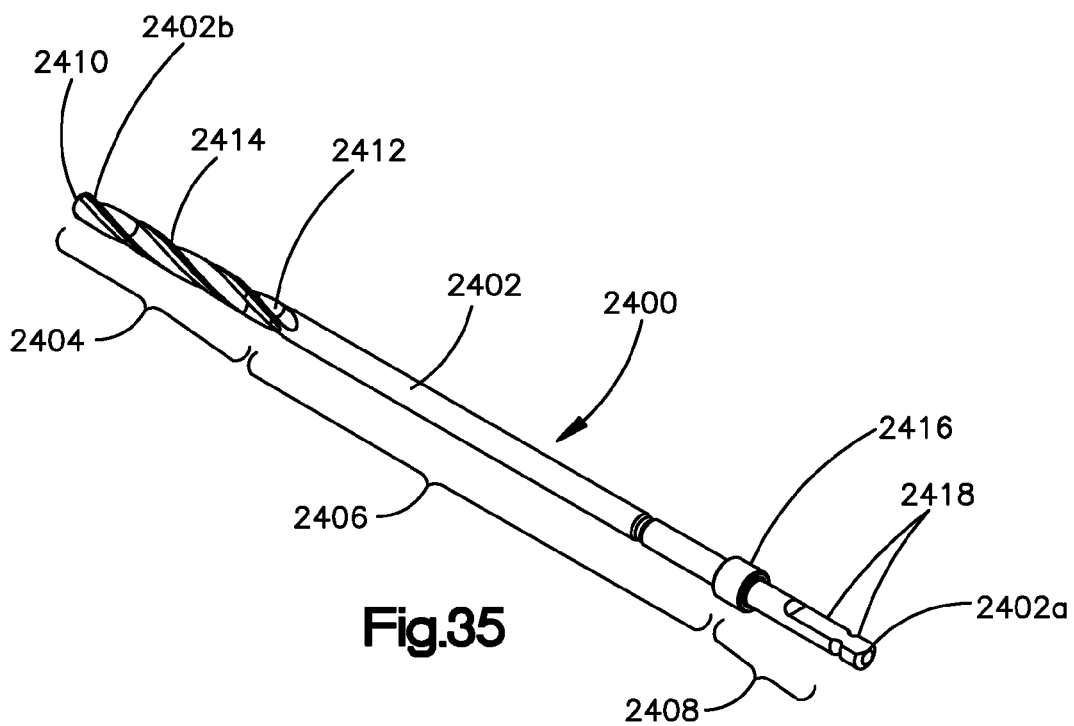
FIG. 35 is a perspective view of the milling bit illustrated in FIG. 33.

Referring now to FIGS. 33-35, the facet joint FJ can be further prepared for insertion of the implant 1500. A drill guide 2300 carrying a milling bit 2400 can be inserted into the guide tube 2100 and utilized to create a bore B into the facet joint FJ, the bore B sized to receive the implant 1500. The bore B can operate as an insertion path between the bony surfaces of the inferior and superior articulation surface IS, SS, of the first and second vertebrae V1, V2, along which the implant 1500 can be inserted into the facet joint FJ. The drill guide 2300 and milling bit 2400 can be constructed to be operable within the cannulation 2104 of the guide tube 2100. For example, the drill guide 2300 can be can be inserted into the cannulation 2104 of the guide tube 2100 and slidably advanced through the cannulation 2104 to the facet joint FJ, and can be moved back and forth in a lateral sweeping motion within the cannulation 2104. In accordance with the illustrated embodiment, the drill guide 2300 includes a substantially cylindrical shaped guide body 2302 defining a proximal end 2302a and an opposed distal end 2302b. The body defines a cannulation 2304 therethrough, the cannulation sized to receive the milling bit 2400. The guide body 2302 can include a guide shaft portion 2306 and a gripping portion 2308.

The guide shaft portion 2306 can be sized and configured to be received in, and longitudinally and laterally translatable in, the cannulation 2104 of the guide tube 2100. In accordance with the illustrated embodiment, the guide shaft portion 2306 of the guide body 2302 defines laterally opposed flat surfaces 2303 that each have first and second guide bosses 2307, 2305 extending laterally outward therefrom, the longitudinal locations of the guide bosses 2307, 2305 on one of the flat surfaces mirroring those of the bosses 2307, 2305 on the opposed flat surface, the guide bosses 2307, 2305 configured to be received in respective pairs of the first and second guide channels 2114, 2116 of the guide tube 2100, respectively. In particular, the first guide bosses 2307 can be sized to be slidably received in the first channels 2114 of the guide tube 2100, the guide bosses 2307 defining outer diameters that are substantially equal to the widths of the first channels 2114. The guide bosses 2307 can be longitudinally located along the guide shaft portion 2306 such that when the bosses 2307 abut the ends of the first channels 2114, the bore B has be cut into the facet joint FJ to a desired depth.

The second guide bosses 2305 can be sized to be slidably received in the tapered second channels 2116 of the guide tube 2100, the guide bosses 2305 defining outer diameters substantially that are undersized within the second channels 2116, enabling the drill guide 2300 to be laterally translated back and forth within the second channels 2116, such that the milling bit 2400 carried by the drill guide 2300 can operate to cut the oval shaped bore B into the facet joint FJ. It should be appreciated that the drill guide 2300 is not limited to the illustrated guide bosses 2307, 2305, and that the drill guide 2300 can alternatively be constructed with more or fewer guide bosses having any other geometry and/or location on the guide shaft portion 2306, as desired.

The gripping portion 2308 can be configured such that the distal end of the gripping portion 2308 abuts the proximal end 2102a of the guide tube 2100 when the drill guide 2300 is inserted in the guide tube 2100. The gripping portion 2308 of the guide body 2302 can define at least one, such as a plurality of gripping elements, the gripping elements configured to facilitate the gripping and maneuvering of the drill guide 2300 as it is inserted into the guide tube 2100 and during drilling of the bore B in the facet joint FJ. For example, the proximal end 2302a of the guide body 2302 of the illustrated drill guide 2300 defines a plurality of annular gripping grooves 2310 spaced inwardly from the proximal end 2302a of the guide body 2302. It should be appreciated that the drill guide 2300 is not limited to the gripping elements of the illustrated grooves 2310, and that the guide body 2302 can be alternatively constructed with any other type of suitable gripping elements as desired.

In accordance with the illustrated embodiment, the milling bit 2400 includes a substantially cylindrically shaped bit body 2402 defining a proximal end 2402a and an opposed distal end 2402b. The bit body 2402 can define a cutting portion 2404 near the distal end 2402b, a shank portion 2408 near the proximal end 2402a, and an intermediate portion 2406 that extends between the cutting and shank portions 2404, 2408, respectively.

The cutting portion 2404 can be configured to drill into the facet joint FJ, so as to create a bore B in the facet joint FJ between the inferior and superior surfaces IS, SS of the facet joint FJ. The cutting portion 2404 can define a cutting tip 2410 defined at the distal end 2402b of the bit body 2402, and at least one, such as a plurality of helical flutes 2412 extending from the distal end 2402b along the bit body 2402 in a direction toward the proximal end 2402a, the flutes 2412 defining respective opposed cutting edges 2414 along their respective lengths. Alternatively, the cutting portion 2404 of the milling bit 2400 can be constructed with an outer coating, such as diamond grit or the like, such that the milling bit 2400 can be operated at a high rotational speed.

The intermediate portion 2406 can define an outer diameter that is sized to be approximately that of the cannulation 2304 of the drill guide 2300, but slightly narrower such that the milling bit 2400 can be received in, and slidably translatable and rotatable in, the cannulation 2304. The bit body 2402 can define a raised annular collar 2416 at the intersection of the proximal end of the intermediate portion 2406 and the distal end of the shank portion 2408, the collar 2416 having a diameter larger than the cannulation 2304 of the drill guide 2300, such that the distal surface of the collar abuts the proximal end 2302a of the drill guide 2300 when the milling bit 2400 is fully inserted into the drill guide 2300.

The shank portion 2408 of the bit body 2402 can define at least one, such as a plurality of drive engaging elements 2418, the drive engaging elements 2418 configured to engage with complementary drive engaging elements of a driving instrument and/or device configured to apply torque to the milling bit 2400, such as a motorized drill, a handle, or the like.

In use, the milling bit 2400 can be coupled to a driving instrument and/or device before or after the milling bit 2400 is inserted into the drill guide 2300 and before or after the drill guide 2300 is inserted into the cannulation 2104 of the guide tube 2100. The driving instrument can be operated to apply torque to the milling bit 2400 such that the cutting portion 2404 advances into the facet joint FJ, defining the bore B in the facet joint by cutting and removing bone from the inferior and/or superior articulation surfaces IS, SS of the facet joint FJ. The milling bit 2400 can be rotatably advanced into the facet joint FJ until the distal surface of the collar 2416 abuts the proximal end 2302a of the drill guide tube 2300, at which point the bore B has been cut to the desired depth. In the illustrated embodiment, the drill guide 2300 can be moved back and forth laterally within the cannulation 2104 of the guide tube 2100 in a sweeping motion, causing the milling bit 2400 to define an oval shaped bore B sized to receive the implant 1500. Alternatively, the cannulation 2104 of the guide tube 2100 can be configured to receive the drill guide 2300 in a series of plunge type drill cuts spaced apart so as to define an oval shaped bore B sized to receive the implant 1500. Once the bore B has been cut in the facet joint FJ, the drill guide 2300 and milling bit 2400 can be removed from the guide tube 2100.

Referring now to FIGS. 36A-39, with the bore B in the facet joint FJ drilled, the implant 1500 can be deployed into the facet joint FJ and inserted into position. The implant 1500 can be deployed into the facet joint FJ using a tamping inserter tip 2500 coupled to a tamping inserter 2600. The implant 1500 can be releasably coupled to the tamping inserter tip 2500, and the implant 1500, tamping inserter tip 2500, and tamping inserter 2600, which together comprise an implant inserter assembly 2700, can be inserted into the cannulation 2104 of the guide tube 2100 and slidably advanced through the cannulation 2104, thereby delivering the implant 1500 to the facet joint FJ. The implant 1500 can then be inserted position in the bore B of the facet joint FJ by applying one or more impaction forces to the tamping inserter 2600.

In accordance with the illustrated embodiment, the tamping inserter tip 2500 includes a tip body 2502 that defines a proximal end 2502a and an opposed distal end 2502b. The tip body 2502 can define a grasping portion 2504 near the distal end 2502b, an engaging portion 2508 near the proximal end 2502a, and a tapered neck portion 2506 that extends between the grasping and engaging portions 2504, 2508, respectively. The cross-sectional profile of the grasping portion 2504 is substantially equal to that of intermediate section 1502c of the implant 1500, such that the cross-sectional profiles of the implant 1500 and the tip body 2502 are continuous when the implant 1500 is coupled to the tamping inserter tip 2500 (i.e., the implant 1500 and the tamping inserter tip 2500 define an uninterrupted outer profile. The distal end 2502b of the tip body 2502 can define a curved end surface 2510, the curved end surface configured to abut the curved surface of the proximal end 1502a of the body 1502 of the implant 1500 when the implant 1500 is coupled to the tamping inserter tip 2500.

The distal end 2502b of the tip body 2502 can further define at least one, such as a plurality of grasping elements, the grasping elements configured to releasably grasp the implant 1500. In the illustrated embodiment, the distal end 2502b of the tip body 2502 includes a pair of grasping elements in the form of a pair of resilient grasping arms 2512 extending from the distal end 2502b of the tip body 2502 in a direction away from the distal end 2502b. The grasping arms 2512 can be angled inwardly towards the center of the tip body 2502, such that the distance between the tips 2514 of the arms 2512 is shorter than the distance between the inner surfaces 1506d of the recesses 1506 of the implant 1500. When the implant 1500 is coupled to the tamping inserter tip 2500, the tips 2514 of the arms 2512 contact the inner surfaces 1506d of the recesses 1506, causing the arms 2512 to deflect outwardly, applying retention forces against the inner surfaces 1506d of the recesses 1506, the retention forces sufficient to retain the implant 1500 within the arms 2512. It should be appreciated that the grasping elements of the tamping inserter tip 2500 are not limited to the illustrated arms 2512, and that the tamping inserter tip 2500 can alternatively be configured with any other suitable grasping elements as desired.

The engaging portion 2508 of the tip body 2502 has a substantially cylindrical cross-sectional profile, and is configured as an engaging element in the form of a plug 2516 configured to be received by a complimentary engaging element of the tamping inserter 2600. The plug 2516 includes an annular groove 2518 extending into the outer surface of the plug 2516, the groove 2518 configured to operate as a detent when the tamping inserter tip 2500 is coupled to the tamping inserter 2600.

In accordance with the illustrated embodiment, the tamping inserter 2600 includes a substantially cylindrically shaped inserter body 2602 defining a proximal end 2602a and an opposed distal end 2602b. The distal end 2602b of the inserter body 2602 can define an engaging element in the form of a plug receptacle 2604 extending into the inserter body 2602 along a direction that is substantially parallel to that of the longitudinal axis L, the plug receptacle 2604 configured to receive the plug 2516 of the tamping inserter tip 2500. The inner surface of the plug receptacle 2604 defines an annular groove 2606 extending into the inner surface of the plug receptacle 2604. The groove 2606 can have a retention element disposed therein, such as the spring-like element 2608, the spring-like element 2608 configured to releasably retain the tamping inserter tip 2500 in a coupled position on the tamping inserter 2600. It should be appreciated that the tamping inserter 2600 is not limited to the illustrated plug receptacle 2604 engaging element, and that the tamping inserter 2600 can alternatively be constructed with any other suitable engaging element, as desired.

It should further be appreciated that the engaging element, for instance the plug receptacle 2604, enables the tamping inserter 2600 to be utilized with multiple tamping inserter tips, for example tamping inserter tips configured for implants other than the implant 1500. It should further still be appreciated that the tamping inserter tip 2500 can be integral with the tamping inserter 2600. The proximal end 2602a of the illustrated tamping inserter 2600 defines an impaction element 2610, the impaction element configured to be impacted by a mallet, or other source of impaction force.

In use, the tamping inserter tip 2500, that is the tamping inserter tip configured for use with the implant 1500, can be releasably coupled to the tamping inserter 2600 by inserting the plug 2516 into the plug receptacle 2604 until the spring 2608 comes to rest in the groove 2518. The implant 1500 can be releasably coupled to the tamping inserter tip 2500 by inserting the arms 2512 of the tamping inserter tip 2500 into the grooves 1506 of the implant 1500. The assembled implant 1500, tamping inserter tip 2500, and tamping inserter 2600 (i.e., the implant inserter assembly 2700) can then be used to deploy the implant 1500 to the bore B in the facet joint, for example by inserting the inserter assembly into the cannulation 2104 of the guide tube 2100 and advancing the implant 1500 through the guide tube 2100 to the facet joint FJ. The implant 1500 can be impacted into place in the bore B of the facet joint FJ by applying at least one, such as a plurality of impaction forces to the impaction element 2610 of the tamping inserter 2600. When the implant 1500 is fully inserted in the facet joint FJ, the tamping inserter 2600 can be operated to release the implant 1500 from the tamping inserter tip 2500, for example by applying a force in a direction opposite from the insertion direction of the implant 100 sufficient to dislodge the arms 2512 of the tamping inserter tip 2500 from the grooves 1506 of the implant 1500. The tamping inserter 2600 and the tamping inserter tip 2500 can then be removed from the guide tube 2100, and the guide tube 2100 can be removed from the facet joint FJ, leaving the implant 1500 in its inserted position within the facet joint FJ, as illustrated in FIG. 39.

It should be appreciated that while the above-described steps of the illustrated surgical implant insertion method refer to the insertion of a single implant 1500 into the facet joint FJ on the right hand side of a patient's spine, that the method can further include repeating the above-described steps to insert a second implant 1500 into the facet joint between the vertebrae V1, V2 on the opposed side of the patient's spine. It should further be appreciated that more than one implant 1300-1900 can be inserted into a single facet joint FJ, the implants 1300-1900 sized the same or differently. It should further still be appreciated that one or more implants 1300-1900 can be inserted into a single facet joint FJ along with one or more of the above-described implants 100-400. It should further still be appreciated that the implant insertion surgical method is not limited to the precise number and/or order of surgical method steps described in accordance with the illustrated embodiment, and that the surgical method can alternatively be carried out. It should further still be appreciated that the surgical implant procedure can alternatively be performed omitting certain of the above-described implant insertion instruments.

Figure 40B:
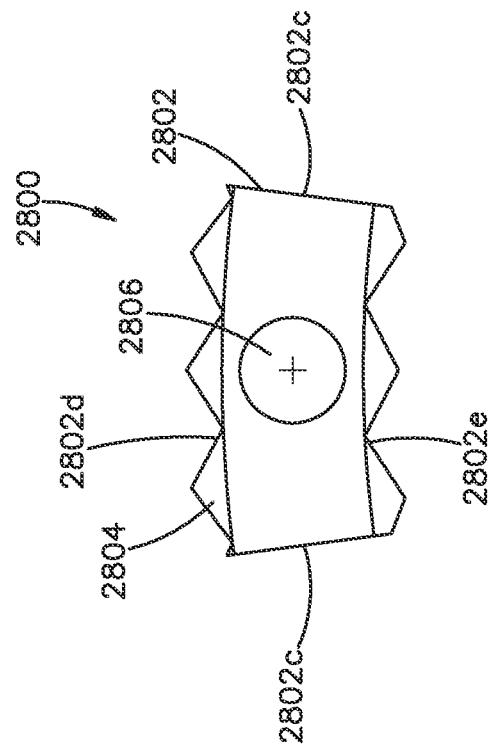
FIG. 40B is a front elevation view of the implant illustrated in FIG. 40A.
Figure 40A:
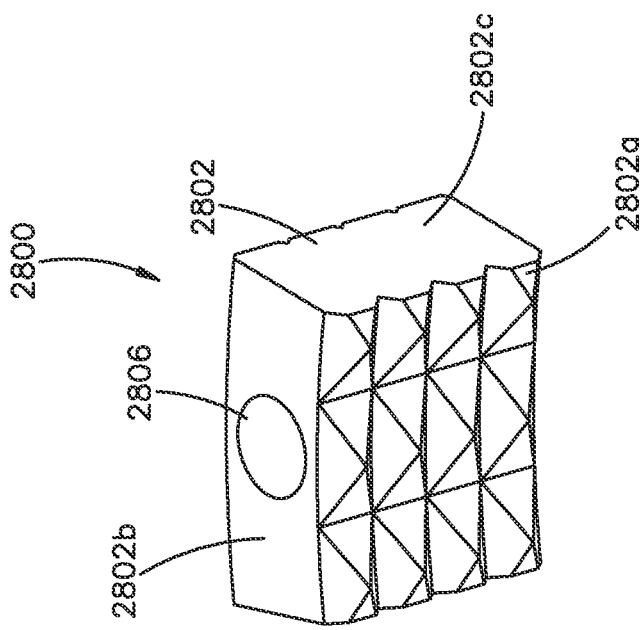
FIG. 40A is a perspective view of a facet fusion implant constructed in accordance with yet another alternative embodiment.
Figure 41:
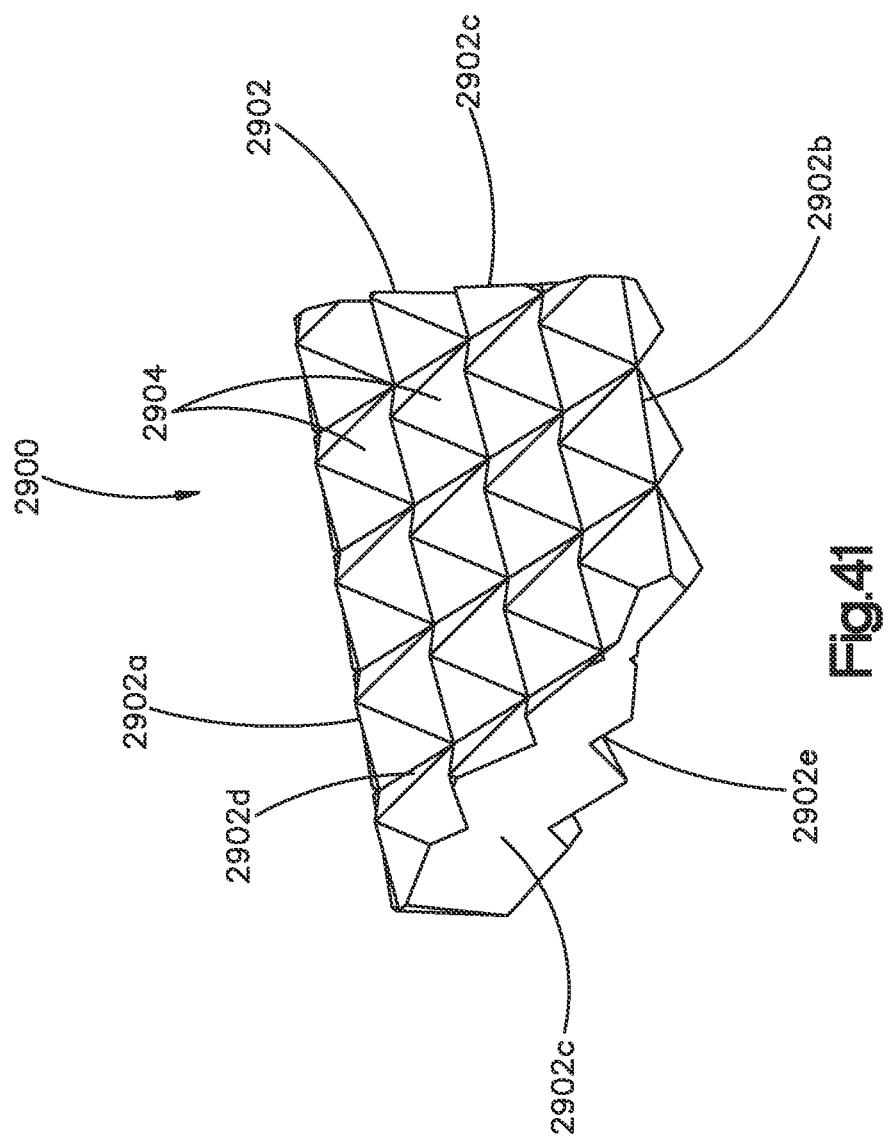
FIG. 41 is a perspective view of a facet fusion implant constructed in accordance with yet another alternative embodiment.

Referring generally now to FIGS. 40A-41, facet fusion implants constructed in accordance with still more alternative embodiments are illustrated. For example, the facet fusion implant 2700 illustrated in FIGS. 40A-B includes an implant body 2702 having a proximal end 2702a, an opposed distal end 2702b, opposed lateral sides 2702c, a curved upper surface 2702d, and an opposed curved lower surface 2702e. In accordance with the illustrated embodiment, the implant body 2702 is substantially rectangular in shape. At least a portion of the upper and/or lower surfaces 2702d, 2702e can define at least one, such as a plurality of gripping elements, such as teeth 2704, the gripping elements configured to minimize migration of the implant 2700 within the facet joint FJ. The body 2702 of the implant 2700 is sized to be received in a facet joint, and its geometry is configured to more closely mimic the natural anatomy of the gap between the opposed articulation surfaces of a facet joint into which the implant is to be inserted, for example the gap between the inferior and superior articulation surfaces IS, SS of the facet joint FJ depicted in FIG. 1. The body 2702 of the illustrated implant 2700 defines a cannulation 2706 therethrough, the cannulation 2706 configured to be slidably inserted over a guide wire, such as a K-wire. The shape of the body 2702 and the curvature of the upper and lower surfaces 2702d, 2702e are intended to maximize the amount of implant surface area that can be placed in contact with the articular surfaces of the facet joint FJ.

The implant 2700 is preferably constructed of allograft tissue, such as allograft bone. The allograft bone can be demineralized in order to enhance the osteoinductive potential of the implant 2700, thereby enhancing its fusion promoting characteristics. It should be appreciated that the implant 2700 is not limited to being constructed of allograft bone, and that the implant 2700 can alternatively be constructed using any other biocompatible, implantable material as desired, including metals such as titanium, titanium alloy such as TAN, or stainless steel, polymers such as polyetheretherketone (PEEK), reinforced plastics, and the like.

Referring now to FIG. 41, a facet fusion implant 2800 constructed in accordance with another alternative embodiment is illustrated. The implant 2800 can be constructed similarly to the implant 2700, but with the body 2802 of the implant 2800 defining a different geometry. For the sake of simplicity, reference numbers used in FIGS. 40A-B to refer to the implant 2700 that correspond to like elements of the implant 2800 are repeated in FIG. 41, incremented by 100. In accordance with the illustrated embodiment, the body 2802 of the implant 2800 can be substantially wedge shaped. In particular, the body 2802 can be tapered between the proximal and distal ends 2802a, 2802b. For example, the thickness of the body 2802, as defined between the upper and lower surfaces 2802d, 2802e, decreases between the proximal end 2802a and the distal end 2802b. Additionally, the width of the body 2802, as defined between the lateral sides 2802c, narrows between the proximal end 2802a and the distal end 2802b. The upper and lower surfaces 2802d, 2802e, can be constructed as substantially flat surfaces.

Although the facet fusion implant has been described herein with reference to preferred embodiments and/or preferred methods, it should be understood that the words which have been used herein are words of description and illustration, rather than words of limitation, and that the scope of the instant disclosure is not intended to be limited to those particulars, but rather is meant to extend to all structures, methods, and/or uses of the herein described facet fusion implant. Those skilled in the relevant art, having the benefit of the teachings of this specification, may effect numerous modifications to the facet fusion implant as described herein, and changes may be made without departing from the scope and spirit of the instant disclosure, for instance as recited in the appended claims.

What is claimed:

1. A facet fusion implant comprising:
    an implant body elongate along a central axis, the implant body including a head portion disposed at a proximal end of the implant body, and a shaft portion that extends from the head portion toward a distal end of the implant body in a distal direction along the central axis, the head portion defining a head cross-sectional dimension that is perpendicular to the central axis, the shaft portion defining a plurality of thread peaks and valleys, and a minimum cross-sectional dimension that is aligned with the respective valley and is perpendicular to the central axis, wherein the head cross-sectional dimension does not exceed the minimum cross-sectional dimension,
    the shaft portion further defining a thread proximal face that extends from a respective peak to the respective valley at a location on the shaft portion that defines the minimum-cross-sectional dimension is aligned with respective valley, and a thread distal face that is opposite the thread proximal face along the central axis such that the thread proximal face faces the proximal end, wherein the thread proximal face defines a first radius of curvature, and the thread distal face defines a second radius of curvature that is greater than the first radius of curvature; and
    an engaging element carried by the head portion, the engaging element configured to engage with a complementary insertion instrument configured to insert the facet fusion implant into the facet joint between the first and second vertebral articulation surfaces.

2. The facet fusion implant of claim 1, wherein the shaft portion defines a maximum cross-sectional dimension defined by a respective peak of the plurality of thread peaks, and the maximum cross-sectional dimension is in the range of about 5.0 mm to 7.0mm, and the minimum cross-sectional dimension is in the range of about 3.5 mm to about 5.5 mm.

3. The facet fusion implant of claim 2, wherein the engaging element is configured to receive a rotational force from the driving instrument and transmit the rotational force to the threaded shaft portion to drive the facet fusion implant into the facet joint.

4. The facet fusion implant of claim 2, wherein the shaft portion defines a maximum cross-sectional dimension at a respective peak, the maximum cross-sectional dimension being perpendicular to the central axis, wherein the maximum cross-sectional dimension is greater than the minimum cross-sectional dimension.

5. The facet fusion implant of claim 2, wherein the threads originate at the distal end of the shaft portion and extend in a direction toward the proximal end.

6. The facet fusion implant of claim 2, wherein the implant body is substantially cylindrical about the central axis.

7. The facet fusion implant of claim 2, wherein the implant is constructed of allograft bone.

8. The facet fusion implant of claim 7, wherein the allograft bone comprises at least partially demineralized allograft.

9. The facet fusion implant of claim 2, wherein the implant defines a cannulation therethrough along the central axis.

10. The facet fusion implant of claim 9, wherein the implant body defines at least one aperture that is open to the cannulation.

11. The facet fusion implant of claim 10, wherein the at least one aperture extends into the body along an axis that is substantially perpendicular to the central axis.

12. The facet fusion implant of claim 9, wherein the implant body defines a plurality of apertures that extend into the body along respective axes that are substantially perpendicular to the central axis, the apertures open to the cannulation and arranged in a helical pattern extending from the distal end in a direction toward the proximal end.

13. The facet fusion implant of claim 12, wherein the plurality of apertures are defined along a valley of the threads.

14. The facet fusion implant of claim 1, wherein the second cross-sectional dimension is greater than a distance that extends from the first vertebral articulation surface to the second vertebral articulation surface.

15. The facet fusion implant of claim 1, wherein the engaging element defines at least one recess, the recess configured to receive a complementary grasping element of an insertion instrument.

16. The facet fusion implant of claim 15, wherein the implant body is at least partially constructed of cortical bone.

17. The facet fusion implant of claim 16, wherein the shaft portion is constructed of cancellous bone and the head portion is constructed of cortical bone.

18. The facet fusion implant of claim 15, wherein the implant body has a substantially cylindrical shape.

19. The facet fusion implant of claim 18, wherein the implant body defines at least one circumferential groove extending around the implant body.

20. The facet fusion implant of claim 1, wherein each peak defines a surface that extends along the distal direction between adjacent thread proximal and distal faces.

21. A facet fusion implant configured to engage a facet joint defined by opposed first and second vertebral articulation surfaces, the first and second vertebral articulation surfaces being separated by a distance, the facet fusion implant comprising an implant body constructed of bone, the implant body being elongate along a central axis and including a head portion disposed at a proximal end of the implant body, and a shaft portion that extends from the head portion along a distal direction toward a distal end of the implant body, the head portion defining a head cross-sectional dimension along a direction perpendicular to the distal direction, the shaft portion of the implant body being threaded so as to include peaks and valleys, the shaft portion defining a major cross-sectional dimension at each peak along the direction perpendicular to the distal direction, and a minor cross-sectional dimension at each valley along the direction perpendicular to the distal direction, wherein 1) the head cross-sectional dimension does not exceed either of the major and minor cross-sectional dimensions 2)the minor cross-sectional dimension is less than the major cross-sectional dimension, the shaft portion further defining a thread proximal face that extends from a respective peak to a location of a respective valley that defines the minor cross-sectional dimension, and a thread distal face opposite the thread proximal face along the distal direction such that the thread proximal face faces the proximal end of the implant body, wherein the thread proximal face curves as it extends from the respective peak to the location of the respective valley toward the proximal end; and an engaging element carried by the head portion, the engaging element configured to engage with a complementary insertion instrument configured to insert the facet fusion implant between the first and second vertebral articulation surfaces such that the shaft portion of the implant body simultaneously engages the opposed first and second vertebral articulation surfaces so as to permit fusion with the first and second vertebral articulation surfaces.

22. The facet fusion implant of claim 21, wherein the bone is at least partially demineralized.

23. The facet fusion implant of claim 21, wherein the bone is of allograft bone.

24. The facet fusion implant of claim 23, wherein the major cross-sectional dimension is in the range of about 5.0 mm to 7.0 mm, and the minor cross-sectional dimension is in the range of about 3.5 mm to about 5.5 mm.

25. The facet fusion implant of claim 24, wherein thread defines a thread proximal face and a thread distal face that is opposite the thread proximal face along the central axis such that the thread proximal face faces the proximal end, wherein the thread proximal face defines a first radius of curvature and the thread distal face defines a second radius of curvature that is less than the first radius of curvature.

26. The facet fusion implant of claim 21, wherein the bone is constructed of autograft bone.

27. The facet fusion implant of claim 21, wherein each threaded peak defines a surface that extends along the distal direction between adjacent thread proximal and distal faces.

* * * * *